United States Patent
Braun, III et al.

(10) Patent No.: US 11,477,964 B2
(45) Date of Patent: Oct. 25, 2022

(54) SELECTION OF MATURE FRUIT COLOR IN PEPPER PLANTS

(71) Applicant: Seminis Vegetable Seeds, Inc., St. Louis, MO (US)

(72) Inventors: Carl Joseph Braun, III, Woodland, CA (US); Eva King-Fan Chan, Rosebery (AU); Graeme S. Garvey, Woodland, CA (US); Carl Martin Jones, Sacramento, CA (US); Brian J. Just, Fort Myers, FL (US); Joel M. Kniskern, Sacramento, CA (US); Jonathan R. Mein, Concord, NC (US); Thomas C. Osborn, Kirkwood, MO (US); Petrus M. J. A. van Poppel, Wageningen (NL)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 0 days.

(21) Appl. No.: 17/008,211

(22) Filed: Aug. 31, 2020

(65) Prior Publication Data
US 2021/0087615 A1    Mar. 25, 2021

Related U.S. Application Data

(60) Continuation of application No. 15/643,317, filed on Jul. 6, 2017, now Pat. No. 10,801,057, which is a division of application No. 14/304,722, filed on Jun. 13, 2014, now Pat. No. 9,723,797.

(60) Provisional application No. 61/863,765, filed on Aug. 8, 2013, provisional application No. 61/838,094, filed on Jun. 21, 2013.

(51) Int. Cl.
| | |
|---|---|
| C12Q 1/6895 | (2018.01) |
| C12Q 1/6827 | (2018.01) |
| A01H 6/82 | (2018.01) |
| A01H 1/04 | (2006.01) |
| A01H 5/08 | (2018.01) |

(52) U.S. Cl.
CPC .............. A01H 6/822 (2018.05); A01H 1/04 (2013.01); A01H 5/08 (2013.01); C12Q 1/6827 (2013.01); C12Q 1/6895 (2013.01); C12Q 2600/13 (2013.01); C12Q 2600/156 (2013.01)

(58) Field of Classification Search
None
See application file for complete search history.

(56) References Cited

U.S. PATENT DOCUMENTS

| | | | |
|---|---|---|---|
| 8,026,424 B2 | 9/2011 | Van Der Heiden | |
| 8,044,273 B2 | 10/2011 | Van Der Heiden | |
| 8,067,681 B2 | 11/2011 | Van Der Heiden | |
| 8,415,536 B2 | 4/2013 | Leij | |
| 8,420,905 B2 | 4/2013 | Leij | |
| 8,536,419 B2 | 9/2013 | Lindeman | |

FOREIGN PATENT DOCUMENTS

| | | |
|---|---|---|
| WO | 2004089067 A1 | 10/2004 |
| WO | 2011028120 | 3/2011 |

OTHER PUBLICATIONS

Naresh et al., 2012, Allelic variation at capsanthin capsorubin synthase gene for ripening fruit color in chilli (*Capsicum annuum* L.), Indian J. Genet. 72: 72-78.*
Li et al., 2013, A Further Analysis of the Relationship between Yellow Ripe-Fruit Color and the Capsanthin-Capsorubin Synthase Gene in Pepper (*Capsicum* sp.) Indicated a New Mutant Variant in *C. annuum* and a Tandem Repeat Structure in Promoter Region, PLoS One 8(4): e61996, pp. 1-10.*
"Baloian Farms added to specialty packs with BellaFina baby bell peppers," article 103896; available at <http://www.freshplaza.com/article/103896/Baloian-Farms-adds-to-specialty-Packs-with-BellaFina-baby-bell-peppers>, Dec. 6, 2012.
Borovsky et al., "Induced mutation in 13-Carotene Hydroxylase results in accumulation of 13-carotene and conversion of red to orange color in pepper fruit," Theoret Appl Genet 126:557-565, 2013.
Borovsky et al., "Chlorophyll breakdown during pepper fruit ripening in the chlorophyll retainer mutation is impaired at the homolog of the senescence-inducible stay-green gene," Theoret Appl Genet 117:235-240; 2008.
Bouvier et al. Journal of Biological Chemistry 46(15): 28861-28867 (1996).
Brand et al., "pc8.1,a major QTL for pigment content in pepper fruit, is associated with variation in plastid compartment size," Planta 235(3):579-588, Z0134. (201.2).
Britton, "Structure and properties of carotenoids in relation to function," FASEB J 9:1551-1558, 1995.
European Extended Search Report regarding European Application No. 14814153.4, dated Dec. 16, 2016.

(Continued)

*Primary Examiner* — Bratislav Stankovic
(74) *Attorney, Agent, or Firm* — Dentons US LLP; Matthew Madsen

(57) ABSTRACT

The invention provides methods and compositions for breeding pepper (*Capsicum* sp. such as *Capsicum annuum*) lines, including isogenic and nearly isogenic lines, displaying one or more mature fruit color(s) of interest. Predictive genetic markers and associated sequences and primers, associated with phenotypic diversity at the Ccs locus encoding Capsanthin-Capsorubin Synthase, and the Ze locus encoding Zeaxanthin Epoxidase are also provided, as well as methods for breeding pepper lines. Further provided are pepper plants, and plant parts including seeds, seed mixtures, fruit, and packaged fruit, which display mature fruit color(s) of interest.

16 Claims, 79 Drawing Sheets

Specification includes a Sequence Listing.

(56) References Cited

OTHER PUBLICATIONS

Extended European Search Report regarding Europe Application No. 20163450.8, dated May 29, 2020.
Farre et al., "Travel advice on the road to carotenoids in plants," Plant Science 179:28-48, 2010.
GenBank Accession No. DQ907615.1, "Capsicum annuum cultivar Nockwang capsanthin/capsorubin synthase, promoter region and partial sequence," dated Sep. 1, 2007.
GenBank Accession No. X77289, "C.annuum capsanthin/ capsorubin synthase gene," dated Aug. 23, 1994.
GenBank Accession No. X91491, "C.annuum mRNA for xanthophyll epoxidase," dated Sep. 9, 2004.
Genbank Accession No. X68017.1, "C.annuum psyl mRNA for phytoene synthase," dated Feb. 5, 1994.
Guzman et al., "Variability of carotenoid biosynthesis in orange colored *Capsicum* spp.," Plant Science 179:49-59, 2010.
Ha et al., "A comparison of the carotenoid accumulation in Capsicum varieties that show different ripening colours: deletion of the capsanthin-capsorubin synthase gene is not a prerequisite for the formation of a yellow pepper," J Experim Botany 58:3135-3144, 2007.
Hill et al., "Linkage disequilibrium of finite populations," Theoret Appl Genet 38:226-231, 1968.
Kim et al., "A splicing mutation in the gene encoding phytoene synthase causes orange coloration in habanero pepper fruits," Mol Cells 30:569-574, 2010.
Lang et al., "Orange fruit color in Capsicum due to deletion of Capsanthin-capsorubin synthesis gene," Breeding Science 54:33-39, 2004.
Lefebvre et al., "The capsanthin capsorubin synthase gene: a candidate gene for the y locus controlling the red fruit colour in pepper," Plant Mol Biol 36:785-789, 1998.

Matsufuji et al., Anti-oxidant content of different coloured sweet peppers, white, green, yellow, orange and red (*Capsicum annuum* L.), International Journal of Food Science and Technology, 42(12):1482-1488, 2007.
Popovsky et al., "Molecular genetics of they locus in pepper: its relation to capsanthin-capsorubin synthase and to fruit color," Theoret App/ Genet 101:86-89, 2000.
Purcell et al., "PLINK: A tool set for whole-genome association and population-based linkage analyses," Am J Hum Genet 81:559-575, 2007.
Ramchiary et al., "Application of genetics and genomics towards Capsicum translational research," Plant Biotechnology Reports 8(2):101-123, 2013.
Romer et al., "Genetic Engineering of a Zeaxanthin-rich Potato by Antisense Inactivation and Co-suppression of Carotenoid Epoxidation," Metabolic Engineering 4:263-272, 2002.
Thorup et al., "Candidate gene analysis of organ pigmentation loci in the Solanaceae," PNAS USA 97:11192-11197, 2000.
Wahyuni et al., "Metabolite biodiversity in pepper (Capsicum) fruits of thirty-two diverse accessions: Variation in health-related compounds and implications for breeding," Phytochemistry 72:1358-1370, 2011.
International Search Report and Written Opinion of the ISA for PCT/US2014/042392, dated Nov. 4, 2014.
Li et al. A Further Analysis of the Relationship between Yellow Ripe-Fruit Color and the Capsanthin-Capsorubin Synthase Gene in Pepper. PLOS, vol. 8 1996.†
P. Naresh et al., Allelic variation in capsanthin capsorubin synthase gene for ripening fruit color in chilli, Indian J. Genet., 72:(1) 72-178 2012.†
S. Popovsky et al. Molecular genetics of the y locus in pepper: its relation to capsanthin-capsorubin synthase and to fruit color; Theor Appl Genet; 101:86-89 2000.†
V. Lefebvre et al., The capsanthin-capsorubin synthase gene: a candidate gene for the y locus controlling the red fruit colour in pepper; Plant Molecular Biology; 36:785-789, 1998.†

\* cited by examiner
† cited by third party

| | | |
|---|---|---|
| SBY-99-1273 | TGTTGAATGGAAAATATTGGAAGAATTTCATTTCATTTCAAAAAATAAAGAGTGTAGAG | 60 |
| SMO-28-1234 | TGTTGAATGGAAAATATTGGAAGAATTTCATTTCATTTCAAAAAATAAAGAGTGTAGAG | 60 |
| SBY-99-1339 | TGTTGAATGGAAAATATTGGAAGAATTTCATTTCATTTCAAAAAATAAAGAGTGTAGAG | 60 |
| SBY-99-1296 | TGTTGAATGGAAAATATTGGAAGAATTTCATTTCATTTCAAAAAATAAAGAGTGTAGAG | 60 |
| SBY-99-1179 | TGTTGAATGGAAAATATTGGAAGAATTTCATTTCATTTCAAAAAATAAAGAGTGTAGAG | 60 |
| SBY-29-469 | TGTTGAATGGAAAATATTGGAAGAATTTCATTTCATTTCAAAAAATAAAGAGTGTAGAG | 60 |
| SBY-148-5201 | TGTTGAATGGAAAATATTGGAAGAATTTCATTTCATTTCAAAAAATAAAGAGTGTAGAG | 60 |
| SBR-27-146 | TGTTGAATGGAAAATATTGGAAGAATTTCATTTCATTTCAAAAAATAAAGAGTGTAGAG | 60 |
| Jimmy Nardello | TGTTGAATGGAAAATATTGGAAGAATTTCATTTCATTTCAAAAAATAAAGAGTGTAGAG | 60 |
| 10CA 3745-M | TGTTGAATGGAAAATATTGGAAGAATTTCATTTCATTTCAAAAAATAAAGAGTGTAGAG | 60 |
| SBR-99-1193 | TGTTGAATGGAAAATATTGGAAGAATTTCATTTCATTTCAAAAAATAAAGAGTGTAGAG | 60 |
| SBR-99-1299 | TGTTGAATGGAAAATATTGGAAGAATTTCATTTCATTTCAAAAAATAAAGAGTGTAGAG | 60 |
| SBR-99-1300 | TGTTGAATGGAAAATATTGGAAGAATTTCATTTCATTTCAAAAAATAAAGAGTGTAGAG | 60 |
| HAS-30-1017 | TGTTGAATGGAAAATATTGGAAGAATTTCATTTCATTTCAAAAAATAAAGAGTGTAGAG | 60 |

| | | |
|---|---|---|
| SBY-99-1273 | GGTATTTTTGTAAATCAATATATTTTTCTATAAAAAATATATAAGAAATATTATTTAATA | 120 |
| SMO-28-1234 | GGTATTTTTGTAAATCAATATATTTTTCTATAAAAAATATATAAGAAATATTATTTAATA | 120 |
| SBY-99-1339 | GGTATTTTTGTAAATCAATATATTTTTCTATAAAAAATATATAAGAAATATTATTTAATA | 120 |
| SBY-99-1296 | GGTATTTTTGTAAATCAATATATTTTTCTATAAAAAATATATAAGAAATATTATTTAATA | 120 |
| SBY-99-1179 | GGTATTTTTGTAAATCAATATATTTTTCTATAAAAAATATATAAGAAATATTATTTAATA | 120 |
| SBY-29-469 | GGTATTTTTGTAAATCAATATATTTTTCTATAAAAAATATATAAGAAATATTATTTAATA | 120 |
| SBY-148-5201 | GGTATTTTTGTAAATCAATATATTTTTCTATAAAAAATATATAAGAAATATTATTTAATA | 120 |
| SBR-27-146 | GGTATTTTTGTAAATCAATATATTTTTCTATAAAAAATATATAAGAAATATTATTTAATA | 120 |
| Jimmy Nardello | GGTATTTTTGTAAATCAATATATTTTTCTATAAAAAATATATAAGAAATATTATTTAATA | 120 |
| 10CA 3745-M | GGTATTTTTGTAAATCAATATATTTTTCTATAAAAAATATATAAGAAATATTATTTAATA | 120 |
| SBR-99-1193 | GGTATTTTTGTAAATCAATATATTTTTCTATAAAAAATATATAAGAAATATTATTTAATA | 120 |
| SBR-99-1299 | GGTATTTTTGTAAATCAATATATTTTTCTATAAAAAATATATAAGAAATATTATTTAATA | 120 |
| SBR-99-1300 | GGTATTTTTGTAAATCAATATATTTTTCTATAAAAAATATATAAGAAATATTATTTAATA | 120 |
| HAS-30-1017 | GGTATTTTTGTAAATCAATATATTTTTCTATAAAAAATATATAAGAAATATTATTTAATA | 120 |

FIG. 8

| | | |
|---|---|---|
| SBY-99-1273 | CATCAAATCAAATACTGTATAAGAAATAATGTTAACATAATTAATGCAAGTATAGCTAAT | 180 |
| SMO-28-1234 | CATCAAATCAAATACTGTATAAGAAATAATGTTAACATAATTAATGCAAGTATAGCTAAT | 180 |
| SBY-99-1339 | CATCAAATCAAATACTCTATAAGAAATAATGTTAACATAATTAATGCAAGTATAGCTAAT | 180 |
| SBY-99-1296 | CATCAAATCAAATACTGTATAAGAAATAATGTTAACATAATTAATGCAAGTATAGCTAAT | 180 |
| SBY-99-1179 | CATCAAATCAAATACTGTATAAGAAATAATGTTAACATAATTAATGCAAGTATAGCTAAT | 180 |
| SBY-29-469 | CATCAAATCAAATACTGTATAAGAAATAATGTTAACATAATTAATGCAAGTATAGCTAAT | 180 |
| SBY-148-5201 | CATCAAATCAAATACTGTATAAGAAATAATGTTAACATAATTAATGCAAGTATAGCTAAT | 180 |
| SBR-27-146 | CATCAAATCAAATACTGTATAAGAAATAATGTTAACATAATTAATGCAAGTATAGCTAAT | 180 |
| Jimmy Nardello | CATCAAATCAAATACTGTATAAGAAATAATGTTAACATAATTAATGCAAGTATAGCTAAT | 180 |
| 10CA 3745-M | CATCAAATCAAATACTGTATAAGAAATAATGTTAACATAATTAATGCAAGTATAGCTAAT | 180 |
| SBR-99-1193 | CATCAAATCAAATACTGTATAAGAAATAATGTTAACATAATTAATGCAAGTATAGCTAAT | 180 |
| SBR-99-1299 | CATCAAATCAAATACTGTATAAGAAATAATGTTAACATAATTAATGCAAGTATAGCTAAT | 180 |
| SBR-99-1300 | CATCAAATCAAATACTGTATAAGAAATAATGTTAACATAATTAATGCAAGTATAGCTAAT | 180 |
| HAS-30-1017 | CATCAAATCAAATACTGTATAAGAAATAATGTTAACATAATTAATGCAAGTATAGCTAAT | 180 |

| | | |
|---|---|---|
| SBY-99-1273 | ACCAACATTACTAATGCAAGTATTACTAATACAACCATATTCTATATTAATCTTATATACT | 240 |
| SMO-28-1234 | ACCAACATTACTAATGCAAGTATTACTAATACAACCATATTCTATATTAATCTTATATACT | 240 |
| SBY-99-1339 | ACCAACATTACTAATGCAAGTATTACTAATACAACCATATTCTATATTAATCTTATATACT | 240 |
| SBY-99-1296 | ACCAACATTACTAATGCAAGTATTACTAATACAACCATATTCTATATTAATCTTATATACT | 240 |
| SBY-99-1179 | ACCAACATTACTAATGCAAGTATTACTAATACAACCATATTCTATATTAATCTTATATACT | 240 |
| SBY-29-469 | ACCAACATTACTAATGCAAGTATTACTAATACAACCATATTCTATATTAATCTTATATACT | 240 |
| SBY-148-5201 | ACCAACATTACTAATGCAAGTATTACTAATACAACCATATTCTATATTAATCTTATATACT | 240 |
| SBR-27-146 | ACCAACATTACTAATGCAAGTATTACTAATACAACCATATTCTATATTAATCTTATATACT | 240 |
| Jimmy Nardello | ACCAACATTACTAATGCAAGTATTACTAATACAACCATATTCTATATTAATCTTATATACT | 240 |
| 10CA 3745-M | ACCAACATTACTAATGCAAGTATTACTAATACAACCATATTCTATATTAATCTTATATACT | 240 |
| SBR-99-1193 | ACCAACATTACTAATGCAAGTATTACTAATACAACCATATTCTATATTAATCTTATATACT | 240 |
| SBR-99-1299 | ACCAACATTACTAATGCAAGTATTACTAATACAACCATATTCTATATTAATCTTATATACT | 240 |
| SBR-99-1300 | ACCAACATTACTAATGCAAGTATTACTAATACAACCATATTCTATATTAATCTTATATACT | 240 |
| HAS-30-1017 | ACCAACATTACTAATGCAAGTATTACTAATACAACCATATTCTATATTAATCTTATATACT | 240 |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | AGTATTTATTGGGTAGGGAAATGTCATGACTTCACAGCATTAAGCATCAAGGGTATAACT | 420 |
| Jimmy Nardello | AGTATTTATTGGGTAGGGAAATGTCATGACTTCACAGCATTAAGCATCAAGGGTATAACT | 420 |
| 10CA 3745-M | AGTATTTATTGGGTAGGGAAATGTCATGACTTCACAGCATTAAGCATCAAGGGTATAACT | 420 |
| SBR-99-1193 | AGTATTTATTGGGTAGGGAAATGTCATGACTTCACAGCATTAAGCATCAAGGGTATAACT | 420 |
| SBR-99-1299 | AGTATTTATTGGGTAGGGAAATGTCATGACTTCACAGCATTAAGCATCAAGGGTATAACT | 420 |
| SBR-99-1300 | AGTATTTATTGGGTAGGGAAATGTCATGACTTCACAGCATTAAGCATCAAGGGTATAACT | 420 |
| HAS-30-1017 | AGTATTTATTGGGTAGGGAAATGTCATGACTTCACAGCATTAAGCATCAAGGGTATAACT | 420 |
| | ************************************************************ | |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | TAATGAAATAGTGGTCAATGAATTATATTGAGAATGACGAGGTCTCTGTTCCAACTTTGG | 480 |
| Jimmy Nardello | TAATGAAATAGTGGTCAATGAATTATATTGAGAATGACGAGGTCTCTGTTCCAACTTTGG | 480 |
| 10CA 3745-M | TAATGAAATAGTGGTCAATGAATTATATTGAGAATGACGAGGTCTCTGTTCCAACTTTGG | 480 |
| SBR-99-1193 | TAATGAAATAGTGGTCAATGAATTATATTGAGAATGACGAGGTCTCTGTTCCAACTTTGG | 480 |
| SBR-99-1299 | TAATGAAATAGTGGTCAATGAATTATATTGAGAATGACGAGGTCTCTGTTCCAACTTTGG | 480 |
| SBR-99-1300 | TAATGAAATAGTGGTCAATGAATTATATTGAGAATGACGAGGTCTCTGTTCCAACTTTGG | 480 |
| HAS-30-1017 | TAATGAAATAGTGGTCAATGAATTATATTGAGAATGACGAGGTCTCTGTTCCAACTTTGG | 480 |
| | ************************************************************ | |

| | |
|---|---|
| SBY-99-1273 | ---- |
| SMO-28-1234 | ---- |
| SBY-99-1339 | ---- |
| SBY-99-1296 | ---- |
| SBY-99-1179 | ---- |
| SBY-29-469 | ---- |
| SBY-148-5201 | ---- |
| SBR-27-146 | ATTGAAAAAATCTATTTATAACTAACTTTAAATCGGCCTTTACGTATCGACGTAATCAAAA 780 |
| Jimmy Nardello | ATTGAAAAAATCTATTTATAACTAACTTTAAATCGGCCTTTACGTATCGACGTAATCAAAA 780 |
| 10CA 3745-M | ATTGAAAAAATCTATTTATAACTAACTTTAAATCGGCCTTTACGTATCGACGTAATCAAAA 780 |
| SBR-99-1193 | ATTGAAAAAATCTATTTATAACTAACTTTAAATCGGCCTTTACGTATCGACGTAATCAAAA 780 |
| SBR-99-1299 | ATTGAAAAAATCTATTTATAACTAACTTTAAATCGGCCTTTACGTATCGACGTAATCAAAA 780 |
| SBR-99-1300 | ATTGAAAAAATCTATTTATAACTAACTTTAAATCGGCCTTTACGTATCGACGTAATCAAAA 780 |
| HAS-30-1017 | ATTGAAAAAATCTATTTATAACTAACTTTAAATCGGCCTTTACGTATCGACGTAATCAAAA 780 |
| | ******************************************************* |

| | |
|---|---|
| SBY-99-1273 | ---- |
| SMO-28-1234 | ---- |
| SBY-99-1339 | ---- |
| SBY-99-1296 | ---- |
| SBY-99-1179 | ---- |
| SBY-29-469 | ---- |
| SBY-148-5201 | ---- |
| SBR-27-146 | TTGTGTCAGCTTGCCACGTGGGGTCTAGTATGAGTTTGAAATTGGTCATAGGGCCCCAA 840 |
| Jimmy Nardello | TTGTGTCAGCTTGCCACGTGGGGTCTAGTATGAGTTTGAAATTGGTCATAGGGCCCCAA 840 |
| 10CA 3745-M | TTGTGTCAGCTTGCCACGTGGGGTCTAGTATGAGTTTGAAATTGGTCATAGGGCCCCAA 840 |
| SBR-99-1193 | TTGTGTCAGCTTGCCACGTGGGGTCTAGTATGAGTTTGAAATTGGTCATAGGGCCCCAA 840 |
| SBR-99-1299 | TTGTGTCAGCTTGCCACGTGGGGTCTAGTATGAGTTTGAAATTGGTCATAGGGCCCCAA 840 |
| SBR-99-1300 | TTGTGTCAGCTTGCCACGTGGGGTCTAGTATGAGTTTGAAATTGGTCATAGGGCCCCAA 840 |
| HAS-30-1017 | TTGTGTCAGCTTGCCACGTGGGGTCTAGTATGAGTTTGAAATTGGTCATAGGGCCCCAA 840 |
| | ******************************************************* |

```
SBY-99-1273
SMC-28-1234
SBY-99-1339
SBY-99-1296
SBY-99-1179
SBY-29-469
SBY-148-5201
SBR-27-146     CTGTAGAAATGATTTCTCATATTTAATCAGTCAAATTATTTAAACAAGAAGAAGTTGATTTT  1140
Jimmy Nardello CTGTAGAAATGATTTCTCATATTTAATCAGTCAAATTATTTAAACAAGAAGAAGTTGATTTT  1140
10CA_3745-M    CTGTAGAAATGATTTCTCATATTTAATCAGTCAAATTATTTAAACAAGAAGAAGTTGATTTT  1140
SBR-99-1193    CTGTAGAAATGATTTCTCATATTTAATCAGTCAAATTATTTAAACAAGAAGAAGTTGATTTT  1140
SBR-99-1299    CTGTAGAAATGATTTCTCATATTTAATCAGTCAAATTATTTAAACAAGAAGAAGTTGATTTT  1140
SBR-99-1300    CTGTAGAAATGATTTCTCATATTTAATCAGTCAAATTATTTAAACAAGAAGAAGTTGATTTT  1140
HAS-30-1017    CTGTAGAAATGATTTCTCATATTTAATCAGTCAAATTATTTAAACAAGAAGAAGTTGATTTT  1140
               ************************************************************

SBY-99-1273
SMC-28-1234
SBY-99-1339
SBY-99-1296
SBY-99-1179
SBY-29-469
SBY-148-5201
SBR-27-146     TTTTTAATTTTTTTTTTTTTACAAAAAAAAATTTCAAATGTCAAGTAAGATTTTTCAAATTGAA  1200
Jimmy Nardello TTTTTAATTTTTTTTTTTTTACAAAAAAAAATTTCAAATGTCAAGTAAGATTTTTCAAATTGAA  1200
10CA_3745-M    TTTTTAATTTTTTTTTTTTTACAAAAAAAAATTTCAAATGTCAAGTAAGATTTTTCAAATTGAA  1200
SBR-99-1193    TTTTTAATTTTTTTTTTTTTACAAAAAAAAATTTCAAATGTCAAGTAAGATTTTTCAAATTGAA  1200
SBR-99-1299    TTTTTAATTTTTTTTTTTTTACAAAAAAAAATTTCAAATGTCAAGTAAGATTTTTCAAATTGAA  1200
SBR-99-1300    TTTTTAATTTTTTTTTTTTTACAAAAAAAAATTTCAAATGTCAAGTAAGATTTTTCAAATTGAA  1200
HAS-30-1017    TTTTTAATTTTTTTTTTTTTACAAAAAAAAATTTCAAATGTCAAGTAAGATTTTTCAAATTGAA  1200
               ************************************************************
```

FIG. 8 (continued)

| | | |
|---|---|---|
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | ACTGAATAAGCTGCGACTTTAGAAAACAAAAAACTAAGATAAGTAAAAATACCAAAAAGAG | 1260 |
| Jimmy Nardello | ACTGAATAAGCTGCGACTTTAGAAAACAAAAAACTAAGATAAGTAAAAATACCAAAAAGAG | 1260 |
| 10CA 3745-M | ACTGAATAAGCTGCGACTTTAGAAAACAAAAAACTAAGATAAGTAAAAATACCAAAAAGAG | 1260 |
| SBR-99-1193 | ACTGAATAAGCTGCGACTTTAGAAAACAAAAAACTAAGATAAGTAAAAATACCAAAAAGAG | 1260 |
| SBR-99-1299 | ACTGAATAAGCTGCGACTTTAGAAAACAAAAAACTAAGATAAGTAAAAATACCAAAAAGAG | 1260 |
| SBR-99-1300 | ACTGAATAAGCTGCGACTTTAGAAAACAAAAAACTAAGATAAGTAAAAATACCAAAAAGAG | 1260 |
| HAS-30-1017 | ACTGAATAAGCTGCGACTTTAGAAAACAAAAAACTAAGATAAGTAAAAATACCAAAAAGAG | 1260 |
| | ************************************************************ | |
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | TGAATCACATCAATTGAATTCTTCCAACAGTTCGTTTTTTAGTTTCTGTTTTGGGAAGAG | 1320 |
| Jimmy Nardello | TGAATCACATCAATTGAATTCTTCCAACAGTTCGTTTTTTAGTTTCTGTTTTGGGAAGAG | 1320 |
| 10CA 3745-M | TGAATCACATCAATTGAATTCTTCCAACAGTTCGTTTTTTAGTTTCTGTTTTGGGAAGAG | 1320 |
| SBR-99-1193 | TGAATCACATCAATTGAATTCTTCCAACAGTTCGTTTTTTAGTTTCTGTTTTGGGAAGAG | 1320 |
| SBR-99-1299 | TGAATCACATCAATTGAATTCTTCCAACAGTTCGTTTTTTAGTTTCTGTTTTGGGAAGAG | 1320 |
| SBR-99-1300 | TGAATCACATCAATTGAATTCTTCCAACAGTTCGTTTTTTAGTTTCTGTTTTGGGAAGAG | 1320 |
| HAS-30-1017 | TGAATCACATCAATTGAATTCTTCCAACAGTTCGTTTTTTAGTTTCTGTTTTGGGAAGAG | 1320 |
| | ************************************************************ | |

FIG. 8 (continued)

```
SBY-99-1273      ------------------------------------------------------------
SMO-28-1234      ------------------------------------------------------------
SBY-99-1339      ------------------------------------------------------------
SBY-99-1296      ------------------------------------------------------------
SBY-99-1179      ------------------------------------------------------------
SBY-29-469       ------------------------------------------------------------
SBY-148-5201     ------------------------------------------------------------
SBR-27-146       GAGTACTACAAGGTAGGACCTCCAACAATCAACAATATCTAAGTTGCAAAAGTTTTGTG 1380
Jimmy Nardello   GAGTACTACAAGGTAGGACCTCCAACAATCAACAATATCTAAGTTGCAAAAGTTTTGTG 1380
10CA 3745-M      GAGTACTACAAGGTAGGACCTCCAACAATCAACAATATCTAAGTTGCAAAAGTTTTGTG 1380
SBR-99-1193      GAGTACTACAAGGTAGGACCTCCAACAATCAACAATATCTAAGTTGCAAAAGTTTTGTG 1380
SBR-99-1299      GAGTACTACAAGGTAGGACCTCCAACAATCAACAATATCTAAGTTGCAAAAGTTTTGTG 1380
SBR-99-1300      GAGTACTACAAGGTAGGACCTCCAACAATCAACAATATCTAAGTTGCAAAAGTTTTGTG 1380
HAS-30-1017      GAGTACTACAAGGTAGGACCTCCAACAATCAACAATATCTAAGTTGCAAAAGTTTTGTG 1380
                 ************************************************************

SBY-99-1273      ------------------------------------------------------------
SMO-28-1234      ------------------------------------------------------------
SBY-99-1339      ------------------------------------------------------------
SBY-99-1296      ------------------------------------------------------------
SBY-99-1179      ------------------------------------------------------------
SBY-29-469       ------------------------------------------------------------
SBY-148-5201     ------------------------------------------------------------
SBR-27-146       CGTTTTTTAGTTTCTGTTTCGTTTCTGTTTCGAGAAGAGGAATACTACAAGTTCGTTTTTAGTTTCTGTT 1440
Jimmy Nardello   CGTTTTTTAGTTTCTGTTTCGTTTCTGTTTCGAGAAGAGGAATACTACAAGTTCGTTTTTAGTTTCTGTT 1440
10CA 3745-M      CGTTTTTTAGTTTCTGTTTCGTTTCTGTTTCGAGAAGAGGAATACTACAAGTTCGTTTTTAGTTTCTGTT 1440
SBR-99-1193      CGTTTTTTAGTTTCTGTTTCGTTTCTGTTTCGAGAAGAGGAATACTACAAGTTCGTTTTTAGTTTCTGTT 1440
SBR-99-1299      CGTTTTTTAGTTTCTGTTTCGTTTCTGTTTCGAGAAGAGGAATACTACAAGTTCGTTTTTAGTTTCTGTT 1440
SBR-99-1300      CGTTTTTTAGTTTCTGTTTCGTTTCTGTTTCGAGAAGAGGAATACTACAAGTTCGTTTTTAGTTTCTGTT 1440
HAS-30-1017      CGTTTTTTAGTTTCTGTTTCGTTTCTGTTTCGAGAAGAGGAATACTACAAGTTCGTTTTTAGTTTCTGTT 1440
                 ************************************************************
```

```
SBY-99-1273       ----------------------------------------------------------------------   ----
SMO-28-1234       ----------------------------------------------------------------------   ----
SBY-99-1339       ----------------------------------------------------------------------   ----
SBY-99-1296       ----------------------------------------------------------------------   ----
SBY-99-1179       ----------------------------------------------------------------------   ----
SBY-29-469        ----------------------------------------------------------------------   ----
SBY-148-5201      ----------------------------------------------------------------------   ----
SBR-27-146        CCTTCGACGGAAAATTATACTATTTTTATAAGTGAAAATTATTTTTATGTATATATAAT   1860
Jimmy Nardello    CCTTCGACGGAAAATTATACTATTTTTATAAGTGAAAATTATTTTTATGTATATATAAT   1860
10CA 3745-M       CCTTCGACGGAAAATTATACTATTTTTATAAGTGAAAATTATTTTTATGTATATATAAT   1860
SBR-99-1193       CCTTCGACGGAAAATTATACTATTTTTATAAGTGAAAATTATTTTTATGTATATATAAT   1860
SBR-99-1299       CCTTCGACGGAAAATTATACTATTTTTATAAGTGAAAATTATTTTTATGTATATATAAT   1860
SBR-99-1300       CCTTCGACGGAAAATTATACTATTTTTATAAGTGAAAATTATTTTTATGTATATATAAT   1860
HAS-30-1017       CCTTCGACGGAAAATTATACTATTTTTATAAGTGAAAATTATTTTTATGTATATATAAT   1860
                  *********************************************

SBY-99-1273       ----------------------------------------------------------------------   ----
SMO-28-1234       ----------------------------------------------------------------------   ----
SBY-99-1339       ----------------------------------------------------------------------   ----
SBY-99-1296       ----------------------------------------------------------------------   ----
SBY-99-1179       ----------------------------------------------------------------------   ----
SBY-29-469        ----------------------------------------------------------------------   ----
SBY-148-5201      ----------------------------------------------------------------------   ----
SBR-27-146        TGATGTTGAACCCCCCTTCGGTTAGTTCATGTTCATGTATCTATATTTTTATTTGAACCCCGAT   1920
Jimmy Nardello    TGATGTTGAACCCCCCTTCGGTTAGTTCATGTTCATGTATCTATATTTTTATTTGAACCCCGAT   1920
10CA 3745-M       TGATGTTGAACCCCCCTTCGGTTAGTTCATGTTCATGTATCTATATTTTTATTTGAACCCCGAT   1920
SBR-99-1193       TGATGTTGAACCCCCCTTCGGTTAGTTCATGTTCATGTATCTATATTTTTATTTGAACCCCGAT   1920
SBR-99-1299       TGATGTTGAACCCCCCTTCGGTTAGTTCATGTTCATGTATCTATATTTTTATTTGAACCCCGAT   1920
SBR-99-1300       TGATGTTGAACCCCCCTTCGGTTAGTTCATGTTCATGTATCTATATTTTTATTTGAACCCCGAT   1920
HAS-30-1017       TGATGTTGAACCCCCCTTCGGTTAGTTCATGTTCATGTATCTATATTTTTATTTGAACCCCGAT   1920
                  *********************************************
```

| | | |
|---|---|---|
| SBY-99-1273 | ------------------------------ | |
| SMO-28-1234 | ------------------------------ | |
| SBY-99-1339 | ------------------------------ | |
| SBY-99-1296 | ------------------------------ | |
| SBY-99-1179 | ------------------------------ | |
| SBY-29-469 | ------------------------------ | |
| SBY-148-5201 | ------------------------------ | |
| SBR-27-146 | GTTCGTATTTTCGTTTCTATTTTGGGAAGTGGAATAGTATAAGGTAGGACCTCCAACAAT | 2220 |
| Jimmy Nardello | GTTCGTATTTTCGTTTCTATTTTGGGAAGTGGAATAGTATAAGGTAGGACCTCCAACAAT | 2220 |
| 10CA_3745-M | GTTCGTATTTTCGTTTCTATTTTGGGAAGTGGAATAGTATAAGGTAGGACCTCCAACAAT | 2220 |
| SBR-99-1193 | GTTCGTATTTTCGTTTCTATTTTGGGAAGTGGAATAGTATAAGGTAGGACCTCCAACACAT | 2220 |
| SBR-99-1299 | GTTCGTATTTTCGTTTCTATTTTGGGAAGTGGAATAGTATAAGGTAGGACCTCCAACAAT | 2220 |
| SBR-99-1300 | GTTCGTATTTTCGTTTCTATTTTGGGAAGTGGAATAGTATAAGGTAGGACCTCCAACAAT | 2220 |
| HAS-30-1017 | GTTCGTATTTTCGTTTCTATTTTGGGAAGTGGAATAGTATAAGGTAGGACCTCCAACAAT | 2220 |
| | ************************* | |
| SBY-99-1273 | ------------------------------ | |
| SMO-28-1234 | ------------------------------ | |
| SBY-99-1339 | ------------------------------ | |
| SBY-99-1296 | ------------------------------ | |
| SBY-99-1179 | ------------------------------ | |
| SBY-29-469 | ------------------------------ | |
| SBY-148-5201 | ------------------------------ | |
| SBR-27-146 | CACCAATACCTAAATTAAAGTTCCGATTCATTTTTAGTTTCTGTTTTGGAAAGAGAAAT | 2280 |
| Jimmy Nardello | CACCAATACCTAAATTAAAGTTCCGATTCATTTTTAGTTTCTGTTTTGGAAAGAGAAAT | 2280 |
| 10CA_3745-M | CACCAATACCTAAATTAAAGTTCCGATTCATTTTTAGTTTCTGTTTTGGAAAGAGAAAT | 2280 |
| SBR-99-1193 | CACCAATACCTAAATTAAAGTTCCGATTCATTTTTAGTTTCTGTTTTGGAAAGAGAAAT | 2280 |
| SBR-99-1299 | CACCAATACCTAAATTAAAGTTCCGATTCATTTTTAGTTTCTGTTTTGGAAAGAGAAAT | 2280 |
| SBR-99-1300 | CACCAATACCTAAATTAAAGTTCCGATTCATTTTTAGTTTCTGTTTTGGAAAGAGAAAT | 2280 |
| HAS-30-1017 | CACCAATACCTAAATTAAAGTTCCGATTCATTTTTAGTTTCTGTTTTGGAAAGAGAAAT | 2280 |
| | ************************* | |

FIG. 8 (continued)

| | | |
|---|---|---|
| SBY-99-1273 | ------------------------------------------------------ | |
| SMO-28-1234 | ------------------------------------------------------ | |
| SBY-99-1339 | ------------------------------------------------------ | |
| SBY-99-1296 | ------------------------------------------------------ | |
| SBY-99-1179 | ------------------------------------------------------ | |
| SBY-29-469 | ------------------------------------------------------ | |
| SBY-148-5201 | ------------------------------------------------------ | |
| SBR-27-146 | ACTACAAGGTAGGGCCTACAACAATCACCAGTACCTAAATTGTAAAAATTTCAGTTCGTT | 2340 |
| Jimmy Nardello | ACTACAAGGTAGGGCCTACAACAATCACCAGTACCTAAATTGTAAAAATTTCAGTTCGTT | 2340 |
| 10CA 3745-M | ACTACAAGGTAGGGCCTACAACAATCACCAGTACCTAAATTGTAAAAATTTCAGTTCGTT | 2340 |
| SBR-99-1193 | ACTACAAGGTAGGGCCTACAACAATCACCAGTACCTAAATTGTAAAAATTTCAGTTCGTT | 2340 |
| SBR-99-1299 | ACTACAAGGTAGGGCCTACAACAATCACCAGTACCTAAATTGTAAAAATTTCAGTTCGTT | 2340 |
| SBR-99-1300 | ACTACAAGGTAGGGCCTACAACAATCACCAGTACCTAAATTGTAAAAATTTCAGTTCGTT | 2340 |
| HAS-30-1017 | ACTACAAGGTAGGGCCTACAACAATCACCAGTACCTAAATTGTAAAAATTTCAGTTCGTT | 2340 |
| | ************************************************************ | |
| SBY-99-1273 | ------------------------------------------------------ | |
| SMO-28-1234 | ------------------------------------------------------ | |
| SBY-99-1339 | ------------------------------------------------------ | |
| SBY-99-1296 | ------------------------------------------------------ | |
| SBY-99-1179 | ------------------------------------------------------ | |
| SBY-29-469 | ------------------------------------------------------ | |
| SBY-148-5201 | ------------------------------------------------------ | |
| SBR-27-146 | TTTTAGTTTTCTATTTTGAGAAGAGGAATGCTACAAGGTAGGGCCTACAACAATCACCAGT | 2400 |
| Jimmy Nardello | TTTTAGTTTTCTATTTTGAGAAGAGGAATGCTACAAGGTAGGGCCTACAACAATCACCAGT | 2400 |
| 10CA 3745-M | TTTTAGTTTTCTATTTTGAGAAGAGGAATGCTACAAGGTAGGGCCTACAACAATCACCAGT | 2400 |
| SBR-99-1193 | TTTTAGTTTTCTATTTTGAGAAGAGGAATGCTACAAGGTAGGGCCTACAACAATCACCAGT | 2400 |
| SBR-99-1299 | TTTTAGTTTTCTATTTTGAGAAGAGGAATGCTACAAGGTAGGGCCTACAACAATCACCAGT | 2400 |
| SBR-99-1300 | TTTTAGTTTTCTATTTTGAGAAGAGGAATGCTACAAGGTAGGGCCTACAACAATCACCAGT | 2400 |
| HAS-30-1017 | TTTTAGTTTTCTATTTTGAGAAGAGGAATGCTACAAGGTAGGGCCTACAACAATCACCAGT | 2400 |
| | ************************************************************ | |

FIG. 8 (continued)

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | ACCTAAAATTGTAAAAATTTCAGTTCGTTTTTAGTTTCGTTTTTGGGAAGAGGAATACTA | 2460 |
| Jimmy Nardello | ACCTAAAATTGTAAAAATTTCAGTTCGTTTTTAGTTTCGTTTTTGGGAAGAGGAATACTA | 2460 |
| 10CA 3745-M | ACCTAAAATTGTAAAAATTTCAGTTCGTTTTTAGTTTCGTTTTTGGGAAGAGGAATACTA | 2460 |
| SBR-99-1193 | ACCTAAAATTGTAAAAATTTCAGTTCGTTTTTAGTTTCGTTTTTGGGAAGAGGAATACTA | 2460 |
| SBY-99-1299 | ACCTAAAATTGTAAAAATTTCAGTTCGTTTTTAGTTTCGTTTTTGGGAAGAGGAATACTA | 2460 |
| SBR-99-1300 | ACCTAAAATTGTAAAAATTTCAGTTCGTTTTTAGTTTCGTTTTTGGGAAGAGGAATACTA | 2460 |
| HAS-30-1017 | ACCTAAAATTGTAAAAATTTCAGTTCGTTTTTAGTTTCGTTTTTGGGAAGAGGAATACTA | 2460 |
| | ************************************************************ | |
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | CAAGGTAGGGCCTTCAACAATCAGCAATACCTAAATTACAAAAATTTCAATTCGTTTTTT | 2520 |
| Jimmy Nardello | CAAGGTAGGGCCTTCAACAATCAGCAATACCTAAATTACAAAAATTTCAATTCGTTTTTT | 2520 |
| 10CA 3745-M | CAAGGTAGGGCCTTCAACAATCAGCAATACCTAAATTACAAAAATTTCAATTCGTTTTTT | 2520 |
| SBR-99-1193 | CAAGGTAGGGCCTTCAACAATCAGCAATACCTAAATTACAAAAATTTCAATTCGTTTTTT | 2520 |
| SBY-99-1299 | CAAGGTAGGGCCTTCAACAATCAGCAATACCTAAATTACAAAAATTTCAATTCGTTTTTT | 2520 |
| SBR-99-1300 | CAAGGTAGGGCCTTCAACAATCAGCAATACCTAAATTACAAAAATTTCAATTCGTTTTTT | 2520 |
| HAS-30-1017 | CAAGGTAGGGCCTTCAACAATCAGCAATACCTAAATTACAAAAATTTCAATTCGTTTTTT | 2520 |
| | ************************************************************ | |

FIG. 8 (continued)

| | | |
|---|---|---|
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | AGTTTCTGTTTTGGGAAGAGGAATACTACAAGGCAGTGGGCGGAGCTACCTTATGATTAGG | 2580 |
| Jimmy Nardello | AGTTTCTGTTTTGGGAAGAGGAATACTACAAGGCAGTGGGCGGAGCTACCTTATGATTAGG | 2580 |
| 10CA 3745-M | AGTTTCTGTTTTGGGAAGAGGAATACTACAAGGCAGTGGGCGGAGCTACCTTATGATTAGG | 2580 |
| SBR-99-1193 | AGTTTCTGTTTTGGGAAGAGGAATACTACAAGGCAGTGGGCGGAGCTACCTTATGATTAGG | 2580 |
| SBR-99-1299 | AGTTTCTGTTTTGGGAAGAGGAATACTACAAGGCAGTGGGCGGAGCTACCTTATGATTAGG | 2580 |
| SBR-99-1300 | AGTTTCTGTTTTGGGAAGAGGAATACTACAAGGCAGTGGGCGGAGCTACCTTATGATTAGG | 2580 |
| HAS-30-1017 | AGTTTCTGTTTTGGGAAGAGGAATACTACAAGGCAGTGGGCGGAGCTACCTTATGATTAGG | 2580 |
| | ************************************************************ | |
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | GGTTCATCCGAACCTCCTTCGACGGAAAATTATACTATTTTTATATAGTAAAAATTATTT | 2640 |
| Jimmy Nardello | GGTTCATCCGAACCTCCTTCGACGGAAAATTATACTATTTTTATATAGTAAAAATTATTT | 2640 |
| 10CA 3745-M | GGTTCATCCGAACCTCCTTCGACGGAAAATTATACTATTTTTATATAGTAAAAATTATTT | 2640 |
| SBR-99-1193 | GGTTCATCCGAACCTCCTTCGACGGAAAATTATACTATTTTTATATAGTAAAAATTATTT | 2640 |
| SBR-99-1299 | GGTTCATCCGAACCTCCTTCGACGGAAAATTATACTATTTTTATATAGTAAAAATTATTT | 2640 |
| SBR-99-1300 | GGTTCATCCGAACCTCCTTCGACGGAAAATTATACTATTTTTATATAGTAAAAATTATTT | 2640 |
| HAS-30-1017 | GGTTCATCCGAACCTCCTTCGACGGAAAATTATACTATTTTTATATAGTAAAAATTATTT | 2640 |
| | ************************************************************ | |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | AACAATCACCAATACCTAAATTGCAAAAATTTCAGTTCGTTTTTTAATTTCTGTTTTTGGG | 2820 |
| Jimmy Nardello | AACAATCACCAATACCTAAATTGCAAAAATTTCAGTTCGTTTTTTAATTTCTGTTTTTGGG | 2820 |
| 10CA 3745-M | AACAATCACCAATACCTAAATTGCAAAAATTTCAGTTCGTTTTTTAATTTCTGTTTTTGGG | 2820 |
| SBR-99-1193 | AACAATCACCAATACCTAAATTGCAAAAATTTCAGTTCGTTTTTTAATTTCTGTTTTTGGG | 2820 |
| SBR-99-1299 | AACAATCACCAATACCTAAATTGCAAAAATTTCAGTTCGTTTTTTAATTTCTGTTTTTGGG | 2820 |
| SBR-99-1300 | AACAATCACCAATACCTAAATTGCAAAAATTTCAGTTCGTTTTTTAATTTCTGTTTTTGGG | 2820 |
| HAS-30-1017 | AACAATCACCAATACCTAAATTGCAAAAATTTCAGTTCGTTTTTTAATTTCTGTTTTTGGG | 2820 |
| | ************************************************************ | |
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | AAGAGGAATACTACAAGGCCCTCCAACAATCACCAATACCTAAATTGCAAAAATTTCAGTT | 2880 |
| Jimmy Nardello | AAGAGGAATACTACAAGGCCCTCCAACAATCACCAATACCTAAATTGCAAAAATTTCAGTT | 2880 |
| 10CA 3745-M | AAGAGGAATACTACAAGGCCCTCCAACAATCACCAATACCTAAATTGCAAAAATTTCAGTT | 2880 |
| SBR-99-1193 | AAGAGGAATACTACAAGGCCCTCCAACAATCACCAATACCTAAATTGCAAAAATTTCAGTT | 2880 |
| SBR-99-1299 | AAGAGGAATACTACAAGGCCCTCCAACAATCACCAATACCTAAATTGCAAAAATTTCAGTT | 2880 |
| SBR-99-1300 | AAGAGGAATACTACAAGGCCCTCCAACAATCACCAATACCTAAATTGCAAAAATTTCAGTT | 2880 |
| HAS-30-1017 | AAGAGGAATACTACAAGGCCCTCCAACAATCACCAATACCTAAATTGCAAAAATTTCAGTT | 2880 |
| | ************************************************************ | |

FIG. 8 (continued)

```
SBY-99-1273      ------------------------------------------------------------
SMO-28-1234      ------------------------------------------------------------
SBY-99-1339      ------------------------------------------------------------
SBY-99-1296      ------------------------------------------------------------
SBY-99-1179      ------------------------------------------------------------
SBY-29-469       ------------------------------------------------------------
SBY-148-5201     ------------------------------------------------------------
SBR-27-146       TGTTTTTTAGTTTCTGTTTGGGAAGAGGAATATACAAGGTAAGGCCTCCAACAATCAC 2940
Jimmy Nardello   TGTTTTTTAGTTTCTGTTTGGGAAGAGGAATATACAAGGTAAGGCCTCCAACAATCAC 2940
10CA 3745-M      TGTTTTTTAGTTTCTGTTTGGGAAGAGGAATATACAAGGTAAGGCCTCCAACAATCAC 2940
SBR-99-1193      TGTTTTTTAGTTTCTGTTTGGGAAGAGGAATATACAAGGTAAGGCCTCCAACAATCAC 2940
SBR-99-1299      TGTTTTTTAGTTTCTGTTTGGGAAGAGGAATATACAAGGTAAGGCCTCCAACAATCAC 2940
SBR-99-1300      TGTTTTTTAGTTTCTGTTTGGGAAGAGGAATATACAAGGTAAGGCCTCCAACAATCAC 2940
HAS-30-1017      TGTTTTTTAGTTTCTGTTTGGGAAGAGGAATATACAAGGTAAGGCCTCCAACAATCAC 2940
                 ************************************************************

SBY-99-1273      ------------------------------------------------------------
SMO-28-1234      ------------------------------------------------------------
SBY-99-1339      ------------------------------------------------------------
SBY-99-1296      ------------------------------------------------------------
SBY-99-1179      ------------------------------------------------------------
SBY-29-469       ------------------------------------------------------------
SBY-148-5201     ------------------------------------------------------------
SBR-27-146       CAATACCTAAATTGCAAAAATTCAGTTCAGTTCGTTTCTATTTTGGAAGTGGAAT 3000
Jimmy Nardello   CAATACCTAAATTGCAAAAATTCAGTTCAGTTCGTTTCTATTTTGGAAGTGGAAT 3000
10CA 3745-M      CAATACCTAAATTGCAAAAATTCAGTTCAGTTCGTTTCTATTTTGGAAGTGGAAT 3000
SBR-99-1193      CAATACCTAAATTGCAAAAATTCAGTTCAGTTCGTTTCTATTTTGGAAGTGGAAT 3000
SBR-99-1299      CAATACCTAAATTGCAAAAATTCAGTTCAGTTCGTTTCTATTTTGGAAGTGGAAT 3000
SBR-99-1300      CAATACCTAAATTGCAAAAATTCAGTTCAGTTCGTTTCTATTTTGGAAGTGGAAT 3000
HAS-30-1017      CAATACCTAAATTGCAAAAATTCAGTTCAGTTCGTTTCTATTTTGGAAGTGGAAT 3000
                 ************************************************************
```

FIG. 8 (continued)

| | |
|---|---|
| SBY-99-1273 | |
| SMO-28-1234 | |
| SBY-99-1339 | |
| SBY-99-1296 | |
| SBY-99-1179 | |
| SBY-29-469 | |
| SBY-148-5201 | |
| SBR-27-146 | AGTATAAGGTAGGACCTCCAACAATCACCAATAATTGCAAAAGTTCCGATTCATT 3060 |
| Jimmy Nardello | AGTATAAGGTAGGACCTCCAACAATCACCAATAATTGCAAAAGTTCCGATTCATT 3060 |
| 10CA 3745-M | AGTATAAGGTAGGACCTCCAACAATCACCAATAATTGCAAAAGTTCCGATTCATT 3060 |
| SBR-99-1193 | AGTATAAGGTAGGACCTCCAACAATCACCAATAATTGCAAAAGTTCCGATTCATT 3060 |
| SBR-99-1299 | AGTATAAGGTAGGACCTCCAACAATCACCAATAATTGCAAAAGTTCCGATTCATT 3060 |
| SBR-99-1300 | AGTATAAGGTAGGACCTCCAACAATCACCAATAATTGCAAAAGTTCCGATTCATT 3060 |
| HAS-30-1017 | AGTATAAGGTAGGACCTCCAACAATCACCAATAATTGCAAAAGTTCCGATTCATT 3060 |
| | ******************************************************** |
| SBY-99-1273 | |
| SMO-28-1234 | |
| SBY-99-1339 | |
| SBY-99-1296 | |
| SBY-99-1179 | |
| SBY-29-469 | |
| SBY-148-5201 | |
| SBR-27-146 | TTTTAGTTTCTGTTTTGGAAAGAGAAATACTACAAGGTAGGTCTCCAACAATCACCAGT 3120 |
| Jimmy Nardello | TTTTAGTTTCTGTTTTGGAAAGAGAAATACTACAAGGTAGGTCTCCAACAATCACCAGT 3120 |
| 10CA 3745-M | TTTTAGTTTCTGTTTTGGAAAGAGAAATACTACAAGGTAGGTCTCCAACAATCACCAGT 3120 |
| SBR-99-1193 | TTTTAGTTTCTGTTTTGGAAAGAGAAATACTACAAGGTAGGTCTCCAACAATCACCAGT 3120 |
| SBR-99-1299 | TTTTAGTTTCTGTTTTGGAAAGAGAAATACTACAAGGTAGGTCTCCAACAATCACCAGT 3120 |
| SBR-99-1300 | TTTTAGTTTCTGTTTTGGAAAGAGAAATACTACAAGGTAGGTCTCCAACAATCACCAGT 3120 |
| HAS-30-1017 | TTTTAGTTTCTGTTTTGGAAAGAGAAATACTACAAGGTAGGTCTCCAACAATCACCAGT 3120 |
| | ************************************************************ |

FIG. 8 (continued)

| | |
|---|---|
| SBY-99-1273 | ------------------------------------------------- |
| SMO-28-1234 | ------------------------------------------------- |
| SBY-99-1339 | ------------------------------------------------- |
| SBY-99-1296 | ------------------------------------------------- |
| SBY-99-1179 | ------------------------------------------------- |
| SBY-29-469 | ------------------------------------------------- |
| SBY-148-5201 | ------------------------------------------------- |
| SBR-27-146 | ACCTAAATTGTAAAAATTTCAGTTCGTTCGTTTTTTAGTTTCTATTTTGGAAGTGGAATAGTA 3180 |
| Jimmy Nardello | ACCTAAATTGTAAAAATTTCAGTTCGTTCGTTTTTTAGTTTCTATTTTGGAAGTGGAATAGTA 3180 |
| 10CA_3745-M | ACCTAAATTGTAAAAATTTCAGTTCGTTCGTTTTTTAGTTTCTATTTTGGAAGTGGAATAGTA 3180 |
| SBR-99-1193 | ACCTAAATTGTAAAAATTTCAGTTCGTTCGTTTTTTAGTTTCTATTTTGGAAGTGGAATAGTA 3180 |
| SBR-99-1299 | ACCTAAATTGTAAAAATTTCAGTTCGTTCGTTTTTTAGTTTCTATTTTGGAAGTGGAATAGTA 3180 |
| SBR-99-1300 | ACCTAAATTGTAAAAATTTCAGTTCGTTCGTTTTTTAGTTTCTATTTTGGAAGTGGAATAGTA 3180 |
| HAS-30-1017 | ACCTAAATTGTAAAAATTTCAGTTCGTTCGTTTTTTAGTTTCTATTTTGGAAGTGGAATAGTA 3180 |
| | ************************************************* |
| SBY-99-1273 | ------------------------------------------------- |
| SMO-28-1234 | ------------------------------------------------- |
| SBY-99-1339 | ------------------------------------------------- |
| SBY-99-1296 | ------------------------------------------------- |
| SBY-99-1179 | ------------------------------------------------- |
| SBY-29-469 | ------------------------------------------------- |
| SBY-148-5201 | ------------------------------------------------- |
| SBR-27-146 | TAAGGTAGGACCTCCAACAATCACCAATACCTAAATTGCAAAAGTTCCGATTCTTTTTTT 3240 |
| Jimmy Nardello | TAAGGTAGGACCTCCAACAATCACCAATACCTAAATTGCAAAAGTTCCGATTCTTTTTTT 3240 |
| 10CA_3745-M | TAAGGTAGGACCTCCAACAATCACCAATACCTAAATTGCAAAAGTTCCGATTCTTTTTTT 3240 |
| SBR-99-1193 | TAAGGTAGGACCTCCAACAATCACCAATACCTAAATTGCAAAAGTTCCGATTCTTTTTTT 3240 |
| SBR-99-1299 | TAAGGTAGGACCTCCAACAATCACCAATACCTAAATTGCAAAAGTTCCGATTCTTTTTTT 3240 |
| SBR-99-1300 | TAAGGTAGGACCTCCAACAATCACCAATACCTAAATTGCAAAAGTTCCGATTCTTTTTTT 3240 |
| HAS-30-1017 | TAAGGTAGGACCTCCAACAATCACCAATACCTAAATTGCAAAAGTTCCGATTCTTTTTTT 3240 |
| | ************************************************* |

| | |
|---|---|
| SBY-99-1273 | ---------------------------------------------- |
| SMO-28-1234 | ---------------------------------------------- |
| SBY-99-1339 | ---------------------------------------------- |
| SBY-99-1296 | ---------------------------------------------- |
| SBY-99-1179 | ---------------------------------------------- |
| SBY-29-469 | ---------------------------------------------- |
| SBY-148-5201 | ---------------------------------------------- |
| SBR-27-146 | CCTTTTCCATCTCCTTTACTTTCCATTCCTACTCCTAACATGTATAGTTTCAAACACAAC 3660 |
| Jimmy Nardello | CCTTTTCCATCTCCTTTACTTTCCATTCCTACTCCTAACATGTATAGTTTCAAACACAAC 3660 |
| 10CA_3745-M | CCTTTTCCATCTCCTTTACTTTCCATTCCTACTCCTAACATGTATAGTTTCAAACACAAC 3660 |
| SBR-99-1193 | CCTTTTCCATCTCCTTTACTTTCCATTCCTACTCCTAACATGTATAGTTTCAAACACAAC 3660 |
| SBR-99-1299 | CCTTTTCCATCTCCTTTACTTTCCATTCCTACTCCTAACATGTATAGTTTCAAACACAAC 3660 |
| SBR-99-1300 | CCTTTTCCATCTCCTTTACTTTCCATTCCTACTCCTAACATGTATAGTTTCAAACACAAC 3660 |
| HAS-30-1017 | CCTTTTCCATCTCCTTTACTTTCCATTCCTACTCCTAACATGTATAGTTTCAAACACAAC 3660 |
| CCS ORF | CCTTTTCCATCTCCTTTACTTTCCATTCCTACTCCTAACATGTATAGTTTCAAACACAAC 78 |
| | ************************************************************ |
| CCS | P F P S P L L S I P T P N M Y S E K H N |

FIG. 8 (continued)

```
SBY-99-1273     ----------------------------------------------------------
SMC-28-1234     ----------------------------------------------------------
SBY-99-1339     ----------------------------------------------------------
SBY-99-1296     ----------------------------------------------------------
SBY-99-1179     ----------------------------------------------------------
SBY-29-469      ----------------------------------------------------------
SBY-148-5201    ----------------------------------------------------------
SBR-27-146      TCCACTTTTCCAAATCCAACCAAACAAAACAAAAGATTCAAGAAAGTTCCATTATAGAAACAAA  3720
Jimmy Nardello  TCCACTTTTCCAAATCCAACCAAACAAAACAAAAGATTCAAGAAAGTTCCATTATAGAAACAAA  3720
10CA_3745-M     TCCACTTTTCCAAATCCAACCAAACAAAACAAAAGATTCAAGAAAGTTCCATTATAGAAACAAA  3720
SBR-99-1193     TCCACTTTTCCAAATCCAACCAAACAAAACAAAAGATTCAAGAAAGTTCCATTATAGAAACAAA  3720
SBR-99-1299     TCCACTTTTCCAAATCCAACCAAACAAAACAAAAGATTCAAGAAAGTTCCATTATAGAAACAAA  3720
SBR-99-1300     TCCACTTTTCCAAATCCAACCAAACAAAACAAAAGATTCAAGAAAGTTCCATTATAGAAACAAA  3720
HAS-30-1017     TCCACTTTTCCAAATCCAACCAAACAAAACAAAAGATTCAAGAAAGTTCCATTATAGAAACAAA  3720
CCS ORF         TCCACTTTTCCAAATCCAACCAAACAAAACAAAAGATTCAAGAAAGTTCCATTATAGAAACAAA  138
                ****************************************************************

CCS             S  T  F  P  N  P  T  K  Q  K  D  S  R  K  F  H  Y  R  N  K
```

| | | |
|---|---|---|
| SBY-99-1273 | — | |
| SMO-28-1234 | — | |
| SBY-99-1339 | — | |
| SBY-99-1296 | — | |
| SBY-99-1179 | — | |
| SBY-29-469 | — | |
| SBY-148-5201 | GATGTTAACATCTCATGGGTTGATCTGGACGCGGCCTGAATTCGACGTGATCATC | 3840 |
| SBR-27-146 | GATGTTAACATCTCATGGGTTGATCTGGACGCGGCCTGAATTCGACGTGATCATC | 3840 |
| Jimmy Nardello | GATGTTAACATCTCATGGGTTGATCTGGACGCGGCCTGAATTCGACGTGATCATC | 3840 |
| 10CA 3745-M | GATGTTAACATCTCATGGGTTGATCTGGACGCGGCCTGAATTCGACGTGATCATC | 3840 |
| SBR-99-1193 | GATGTTAACATCTCATGGGTTGATCTGGACGCGGCCTGAATTCGACGTGATCATC | 3840 |
| SBR-99-1299 | GATGTTAACATCTCATGGGTTGATCTGGACGCGGCCTGAATTCGACGTGATCATC | 3840 |
| SBR-99-1300 | GATGTTAACATCTCATGGGTTGATCTGGACGCGGCCTGAATTCGACGTGATCATC | 3840 |
| HAS-30-1017 | GATGTTAACATCTCATGGGTTGATCTGGACGCGGCCTGAATTCGACGTGATCATC | 3840 |
| CCS ORF | GATGTTAACATCTCATGGGTTGATCTGGACGCGGCCTGAATTCGACGTGATCATC | 258 |
| | ********************************************** | |
| CCS | D V N I S W V D L D G A E F D V I I | |

FIG. 8 (continued)

```
SBY-99-1273      ----------------------------------------------------------
SMO-28-1234      ----------------------------------------------------------
SBY-99-1339      ----------------------------------------------------------
SBY-99-1296      ----------------------------------------------------------
SBY-99-1179      ----------------------------------------------------------
SBY-29-469       ----------------------------------------------------------
SBY-148-5201     ----------------------------------------------------------
SBR-27-146       ATTGGAACTGGCCCTGCCGGGCTTCGGGCTAGCTGAACAACAAGTTTCTAAATATGGTATTAAG   3900
Jimmy Nardello   ATTGGAACTGGCCCTGCCGGGCTTCGGGCTAGCTGAACAACAAGTTTCTAAATATGGTATTAAG   3900
10CA 3745-M      ATTGGAACTGGCCCTGCCGGGCTTCGGGCTAGCTGAACAACAAGTTTCTAAATATGGTATTAAG   3900
SBR-99-1193      ATTGGAACTGGCCCTGCCGGGCTTCGGGCTAGCTGAACAACAAGTTTCTAAATATGGTATTAAG   3900
SBR-99-1299      ATTGGAACTGGCCCTGCCGGGCTTCGGGCTAGCTGAACAACAAGTTTCTAAATATGGTATTAAG   3900
SBR-99-1300      ATTGGAACTGGCCCTGCCGGGCTTCGGGCTAGCTGAACAACAAGTTTCTAAATATGGTATTAAG   3900
HAS-30-1017      ATTGGAACTGGCCCTGCCGGGCTTCGGGCTAGCTGAACAACAAGTTTCTAAATATGGTATTAAG   3900
CCS ORF          ATTGGAACTGGCCCTGCCGGGCTTCGGGCTAGCTGAACAACAAGTTTCTAAATATGGTATTAAG   318
                 ****************************************************************

CCS              I  G  T  G  P  A  G  L  R  L  A  E  Q  V  S  K  Y  G  I  K
```

FIG. 8 (continued)

```
SBY-99-1273   ------------------------------------------------------------
SMO-28-1234   ------------------------------------------------------------
SBY-99-1339   ------------------------------------------------------------
SBY-99-1296   ------------------------------------------------------------
SBY-99-1179   ------------------------------------------------------------
SBY-29-469    ------------------------------------------------------------
SBY-148-5201  ------------------------------------------------------------
SBR-27-146    GTATGTTGCGTTGACCCTTCACCACTTTCCATGTGGCCAAATAATTATGGTGTTTGGGTT  3960
Jimmy Nardello GTATGTTGCGTTGACCCTTCACCACTTTCCATGTGGCCAAATAATTATGGTGTTTGGGTT  3960
10CA 3745-M   GTATGTTGCGTTGACCCTTCACCACTTTCCATGTGGCCAAATAATTATGGTGTTTGGGTT  3960
SBR-99-1193   GTATGTTGCGTTGACCCTTCACCACTTTCCATGTGGCCAAATAATTATGGTGTTTGGGTT  3960
SBR-99-1299   GTATGTTGCGTTGACCCTTCACCACTTTCCATGTGGCCAAATAATTATGGTGTTTGGGTT  3960
SBR-99-1300   GTATGTTGCGTTGACCCTTCACCACTTTCCATGTGGCCAAATAATTATGGTGTTTGGGTT  3960
HAS-30-1017   GTATGTTGCGTTGACCCTTCACCACTTTCCATGTGGCCAAATAATTATGGTGTTTGGGTT  3960
CCS ORF       GTATGTTGCGTTGACCCTTCACCACTTTCCATGTGGCCAAATAATTATGGTGTTTGGGTT  378
              ************************************************************

CCS           V C C V D P S P L S M W P N N Y G V W V
```

FIG. 8 (continued)

```
SBY-99-1273       ----------------------------------------------------------------------
SMO-28-1234       ----------------------------------------------------------------------
SBY-99-1339       ----------------------------------------------------------------------
SBY-99-1296       ----------------------------------------------------------------------
SBY-99-1179       ----------------------------------------------------------------------
SBY-29-469        ----------------------------------------------------------------------
SBY-148-5201      ----------------------------------------------------------------------
SBR-27-146        GATGAGTTTGAAAAGTTGGGATTAGAAGATTGTCTAGATCATAAGTGGCCTGTGAGTTGT  4020
Jimmy Nardello    GATGAGTTTGAAAAGTTGGGATTAGAAGATTGTCTAGATCATAAGTGGCCTGTGAGTTGT  4020
10CA 3745-M       GATGAGTTTGAAAAGTTGGGATTAGAAGATTGTCTAGATCATAAGTGGCCTGTGAGTTGT  4020
SBR-99-1193       GATGAGTTTGAAAAGTTGGGATTAGAAGATTGTCTAGATCATAAGTGGCCTGTGAGTTGT  4020
SBR-99-1299       GATGAGTTTGAAAAGTTGGGATTAGAAGATTGTCTAGATCATAAGTGGCCTGTGAGTTGT  4020
SBR-99-1300       GATGAGTTTGAAAAGTTGGGATTAGAAGATTGTCTAGATCATAAGTGGCCTGTGAGTTGT  4020
HAS-30-1017       GATGAGTTTGAAAAGTTGGGATTAGAAGATTGTCTAGATCATAAGTGGCCTGTGAGTTGT  4020
CCS ORF           GATGAGTTTGAAAAGTTGGGATTAGAAGATTGTCTAGATCATAAGTGGCCTGTGAGTTGT  438
                  ************************************************************

CCS                D  E  F  E  K  L  G  L  E  D  C  L  D  H  K  W  P  V  S  C
```

FIG. 8 (continued)

```
SBY-99-1273                                                                                                           -
SMO-28-1234                                                                                                           -
SBY-99-1339                                                                                                           -
SBY-99-1296                                                                                                           -
SBY-99-1179                                                                                                           -
SBY-29-469                                                                                                            -
SBY-148-5201                                                                                                          -
SBR-27-146     GTTCATATATAAGTGATCACAAGACTAAGTATTTGGACAGACCATATGGTAGAGTAAGTAAGTAGA 4080
Jimmy Nardello GTTCATATATAAGTGATCACAAGACTAAGTATTTGGACAGACCATATGGTAGAGTAAGTAAGTAGA 4080
10CA_3745-M    GTTCATATATAAGTGATCACAAGACTAAGTATTTGGACAGACCATATGGTAGAGTAAGTAAGTAGA 4080
SBR-99-1193    GTTCATATATAAGTGATCACAAGACTAAGTATTTGGACAGACCATATGGTAGAGTAAGTAAGTAGA 4080
SBR-99-1299    GTTCATATAAGTGATCACAAGACTAAGTATTTGGACAGACCATATGGTAGAGTAAGTAAGTAGA  4080
SBR-99-1300    GTTCATATATAAGTGATCACAAGACTAAGTATTTGGACAGACCATATGGTAGAGTAAGTAAGTAGA 4080
HAS-30-1017    GTTCATATATAAGTGATCACAAGACTAAGTATTTGGACAGACCATATGGTAGAGTAAGTAAGTAGA 4080
CCS ORF        GTTCATATATAAGTGATCACAAGACTAAGTATTTGGACAGACCATATGGTAGAGTAAGTAAGTAGA 4080

CCS             V  H  I  S  D  H  K  T  K  Y  L  D  R  P  Y  G  R  V  S  R    498
```

|  |  |
|---|---|
| SBY-99-1273 | ------------------------------------------------------------ |
| SMO-28-1234 | ------------------------------------------------------------ |
| SBY-99-1339 | ------------------------------------------------------------ |
| SBY-99-1296 | ------------------------------------------------------------ |
| SBY-99-1179 | ------------------------------------------------------------ |
| SBY-29-469 | ------------------------------------------------------------ |
| SBY-148-5201 | ------------------------------------------------------------ |
| SBR-27-146 | AGGAAGATAAGCGGTAGCTTGATTGTTGATGCAAGTGGCTATGCTAGTGATTTTATAGAG 4260 |
| Jimmy Nardello | AGGAAGATAAGCGGTAGCTTGATTGTTGATGCAAGTGGCTATGCTAGTGATTTTATAGAG 4260 |
| 10CA_3745-M | AGGAAGATAAGCGGTAGCTTCATCGATGTTGATGCAAGTGGCTATGCCTATCGATTTTATAGAG 4260 |
| SBR-99-1193 | AGGAAGATAAGCGGTAGCTTGATTGTTGATGCAAGTGGCTATGCTAGTGATTTTATAGAG 4260 |
| SBR-99-1299 | AGGAAGATAAGCGGTAGCTTGATTGTTGATGCAAGTGGCTATGCTAGTGATTTTATAGAG 4260 |
| SBR-99-1300 | AGGAAGATAAGCGGTAGCTTGATTGTTGATGCAAGTGGCTATGCTAGTGATTTTATAGAG 4260 |
| HAS-30-1017 | AGGAAGATAAGTGGTAGCTTGATTGTTGATGCAAGTGGCTATGCTAGTGATTTTATAGAG 4260 |
| CCS ORF | AGGAAGATAAGTAGTGGTAGCTTGTTGATGCAAGTGGCTATGCTAGTGATTTTATAGAG 678 |
|  | ********** ***** ************************************ |
| CCS | R K I S G S L I V D A S G Y A S D F I E |

FIG. 8 (continued)

| | |
|---|---|
| SBY-99-1273 | ---------------------------------------------------- |
| SMO-28-1234 | ---------------------------------------------------- |
| SBY-99-1339 | ---------------------------------------------------- |
| SBY-99-1296 | ---------------------------------------------------- |
| SBY-99-1179 | ---------------------------------------------------- |
| SBY-29-469 | ---------------------------------------------------- |
| SBY-148-5201 | ---------------------------------------------------- |
| SBR-27-146 | TATGACAAGCCAAGAAACCATGGTTATCAAGTTGCTCATGGGATTTTAGCAGAAGTTGAT 4320 |
| Jimmy Nardello | TATGACAAGCCAAGAAACCATGGTTATCAAGTTGCTCATGGGATTTTAGCAGAAGTTGAT 4320 |
| 10CA_3745-M | TATGACAAGCCAAGAAACCATGGTTATCAAGTTGCTCATGGGATTTTAGCAGAAGTTGAT 4320 |
| SBR-99-1193 | TATGACAAGCCAAGAAACCATGGTTATCAAGTTGCTCATGGGATTTTAGCAGAAGTTGAT 4320 |
| SBR-99-1299 | TATGACAAGCCAAGAAACCATGGTTATCAAGTTGCTCATGGGATTTTAGCAGAAGTTGAT 4320 |
| SBR-99-1300 | TATGACAAGCCAAGAAACCATGGTTATCAAGTTGCTCATGGGATTTTAGCAGAAGTTGAT 4320 |
| HAS-30-1017 | TATGACAAGCCAAGAAACCATGGTTATCAAGTTGCTCATGGCATTTTAGCAGAAGTTGAT 4320 |
| CCS ORF | TATGACAAGCCAAGAAACCATGGTTATCAAGTTGCTCATGGCATTTTAGCAGAAGTTGAT 738 |
| | ************************************************************ |
| CCS | Y D K P R N H G Y Q V A H G I L A E V D |

FIG. 8 (continued)

| | |
|---|---|
| SBY-99-1273 | ---------------------------------------------------- |
| SMO-28-1234 | ---------------------------------------------------- |
| SBY-99-1339 | ---------------------------------------------------- |
| SBY-99-1296 | ---------------------------------------------------- |
| SBY-99-1179 | ---------------------------------------------------- |
| SBY-29-469 | ---------------------------------------------------- |
| SBY-148-5201 | ---------------------------------------------------- |
| SBR-27-146 | AATCATCCATTTGATTTGGATAAAATGATGATGCTTATGGATTGGAGGGATTCTCATTTAGGT 4380 |
| Jimmy Nardello | AATCATCCATTTGATTTGGATAAAATGATGATGCTTATGGATTGGAGGGATTCTCATTTAGGT 4380 |
| 10CA 3745-M | AATCATCCATTTGATTTGGATAAAATGATGATGCTTATGGATTGGAGGGATTCTCATTTAGGT 4380 |
| SBR-99-1193 | AATCATCCATTTGATTTGGATAAAATGATGATGCTTATGGATTGGAGGGATTCTCATTTAGGT 4380 |
| SBR-99-1299 | AATCATCCATTTCCATAAAATGATGATGCTTATCCACCGATTGGAGGGATTCTCATTTAGCT 4380 |
| SBR-99-1300 | AATCATCCATTTGATTTGGATAAAATGATGATGCTTATGGATTGGAGGGATTCTCATTTAGGT 4380 |
| HAS-30-1017 | AATCATCCATTTGATTTGGATAAAATGATGATGCTTATGGATTGGAGGGATTCTCATTTAGGT 4380 |
| CCS ORF | AATCATCCATTTGATTTGGATAAAATGATGATGCTTATGGATTGGAGGGATTCTCATTTAGGT 798 |
| | ************************************************ |
| CCS | N H P F D L D K M M L M D W R D S H L G |

```
SBY-99-1273      -------------------------------------------------------------
SMO-28-1234      -------------------------------------------------------------
SBY-99-1339      -------------------------------------------------------------
SBY-99-1296      -------------------------------------------------------------
SBY-99-1179      -------------------------------------------------------------
SBY-29-469       -------------------------------------------------------------
SBY-148-5201     -------------------------------------------------------------
SBR-27-146       TTTGATAGGAATTTGGTATTCTTGGAAGAGACTTCTTTAGTGAGTCGGCCTATGTTATCG  4500
Jimmy Nardello   TTTGATAGGAATTTGGTATTCTTGGAAGAGACTTCTTTAGTGAGTCGGCCTATGTTATCG  4500
10CA 3745-M      TTTGATAGGAATTTGGTATTCTTGGAAGAGACTTCTTTAGTGAGTCGGCCTATGTTATCG  4500
SBR-99-1193      TTTGATAGGAATTTGGTATTCTTGGAAGAGACTTCTTTAGTGAGTCGGCCTATGTTATCG  4500
SBR-99-1299      TTTGATAGGAATTTGGTATTCTTGGAAGAGACTTCTTTAGTGAGTCGGCCTATGTTATCG  4500
SBR-99-1300      TTTGATAGGAATTTGGTATTCTTGGAAGAGACTTCTTTAGTGAGTCGGCCTATGTTATCG  4500
HAS-30-1017      TTTGATAGGAATTTGGTATTCTTGGAAGAGACTTCTTTAGTGAGTCGGCCTATGTTATCG  4500
CCS ORF          TTTGATAGGAATTTGGTATTCTTGGAAGAGACTTCTTTAGTGAGTCGGCCTATGTTATCG  918
                 ************************************************************

CCS               F  D  R  N  L  V  F  L  E  E  T  S  L  V  S  R  P  M  L  S
```

FIG. 8 (continued)

| | |
|---|---|
| SBY-99-1273 | |
| SMO-28-1234 | |
| SBY-99-1339 | |
| SBY-99-1296 | |
| SBY-99-1179 | |
| SBY-29-469 | |
| SBY-148-5201 | |
| SBR-27-146 | TATATGGAAGTGAAAAGAAGAATGGTAGCAAGATTAAGACATTTGGGGATCAAAGTGAGA 4560 |
| Jimmy Nardello | TATATGGAAGTGAAAAGAAGAATGGTAGCAAGATTAAGACATTTGGGGATCAAAGTGAGA 4560 |
| 10CA 3745-M | TATATGGAAGTGAAAAGAAGAATGGTAGCAAGATTAAGACATTTGGGGATCAAAGTGAGA 4560 |
| SBR-99-1193 | TATATGGAAGTGAAAAGAAGAATGGTAGCAAGATTAAGACATTTGGGGATCAAAGTGAGA 4560 |
| SBR-99-1299 | TATATGGAAGTGAAAAGAAGAATGGTAGCAAGATTAAGACATTTGGGGATCAAAGTGAGA 4560 |
| SBR-99-1300 | TATATGGAAGTGAAAAGAAGAATGGTAGCAAGATTAAGACATTTGGGGATCAAAGTGAGA 4560 |
| HAS-30-1017 | TATATGGAAGTGAAAAGAAGAATGGTAGCAAGATTAAGACATTTGGGGATCAAAGTGAGA 4560 |
| CCS ORF | ************************************************************ 978 |

CCS    Y  M  E  V  K  R  R  M  V  A  R  L  R  H  L  G  I  K  V  R

FIG. 8 (continued)

```
SBY-99-1273      ---------------------------------------------------------------
SMO-28-1234      ---------------------------------------------------------------
SBY-99-1339      ---------------------------------------------------------------
SBY-99-1296      ---------------------------------------------------------------
SBY-99-1179      ---------------------------------------------------------------
SBY-29-469       ---------------------------------------------------------------
SBY-148-5201     ---------------------------------------------------------------
SBR-27-146       AGTGTCCTTGAGGAAGAGAGAAGTGTGTGATCACTATGGGAGGACCACTTCCGCGGATTCCT 4620
Jimmy Nardello   AGTGTCCTTGAGGAAGAGAGAAGTGTGTGATCACTATGGGAGGACCACTTCCGCGGATTCCT 4620
10CA_3745-M      AGTGTCCTTGAGGAAGAGAGAAGTGTGTGATCACTATGGGAGGACCACTTCCGCGGATTCCT 4620
SBR-99-1193      AGTGTCCTTGAGGAAGAGAGAAGTGTGTGATCACTATGGGAGGACCACTTCCGCGGATTCCT 4620
SBY-99-1299      AGTGTCCTTGAGGAAGAGAGAAGTGTGTGATCACTATGGGAGGACCACTTCCGCGGATTCCT 4620
SBR-99-1300      AGTGTCCTTGAGGAAGAGAGAAGTGTGTGATCACTATGGGAGGACCACTTCCGCGGATTCCT 4620
HAS-30-1017      AGTGTCCTTGAGGAAGAGAGAAGTGTGTGATCACTATGGGAGGACCACTTCCGCGGATTCCT 4620
CCS ORF          AGTGTCCTTGAGGAAGAGAGAAGTGTGTGATCACTATGGGAGGACCACTTCCGCGGATTCCT 1038
                 *************************************************************

CCS              S V L E E K C V I T M G G P L P R I P
```

| | | |
|---|---|---|
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | GTGGCTCGTAGCATGGCATTGGCACCAGTACTGGCTGAGGCCTGAGCCTGAAAGCCTTGGC | 4740 |
| SBR-27-146 | GTGGCTCGTAGCATGGCATTGGCACCAGTACTGGCTGAGGCCTGAGCCTGAAAGCCTTGGC | 4740 |
| Jimmy Nardello | GTGGCTCGTAGCATGGCATTGGCACCAGTACTGGCTGAGGCCTGAGCCTGAAAGCCTTGGC | 4740 |
| 10CA_3745-M | GTGGCTCGTAGCATGGCATTGGCACCAGTACTGGCTGAGGCCTGAGCCTGAAAGCCTTGGC | 4740 |
| SBR-99-1193 | GTGGCTCGTAGCATGGCATTGGCACCAGTACTGGCTGAGGCCTGAGCCTGAAAGCCTTGGC | 4740 |
| SBR-99-1299 | GTGGCTCGTAGCATGGCATTGGCACCAGTACTGGCTGAGGCCTGAGCCTGAAAGCCTTGGC | 4740 |
| SBR-99-1300 | GTGGCTCGTAGCATGGCATTGGCACCAGTACTGGCTGAGGCCTGAGCCTGAAAGCCTTGGC | 4740 |
| HAS-30-1017 | GTGGCTCGTAGCATGGCATTGGCACCAGTACTGGCTGAGGCCTGAGCCTGAAAGCCTTGGC | 4740 |
| CCS ORF | GTGGCTCGTAGCATGGCATTGGCACCAGTACTGGCTGAGGCCTGAGCCTGAAAGCCTTGGC | 1158 |
| | ************************************************************ | |
| CCS | V A R S M A L A P V L A E A I V E S L G | |

| | | |
|---|---|---|
| SBY-99-1273 | TCGGATAGAAGACGTGTTAGAGAATGTTATTGTTTCGGAATGGAGACTTTGTTGTTGAAGCTT | 433 |
| SMO-28-1234 | TCGGATAGAAGACGTGTTAGAGAATGTTATTGTTTCGGAATGGAGACTTTGTTGTTGAAGCTT | 433 |
| SBY-99-1339 | TCGGATAGAAGACGTGTTAGAGAATGTTATTGTTTCGGAATGGAGACTTTGTTGTTGAAGCTT | 433 |
| SBY-99-1296 | TCGGATAGAAGACGTGTTAGAGAATGTTATTGTTTCGGAATGGAGACTTTGTTGTTGAAGCTT | 433 |
| SBY-99-1179 | TCGGATAGAAGACGTGTTAGAGAATGTTATTGTTTCGGAATGGAGACTTTGTTGTTGAAGCTT | 433 |
| SBY-29-469 | TCGGATAGAAGACGTGTTAGAGAATGTTATTGTTTCGGAATGGAGACTTTGTTGTTGAAGCTT | 433 |
| SBY-148-5201 | TCGGATAGAAGACGTGTTAGAGAATGTTATTGTTTCGGAATGGAGACTTTGTTGTTGAAGCTT | 433 |
| SBR-27-146 | TCGGATAGAAGACGTGTTAGAGAATGTTATTGTTTCGGAATGGAGACTTTGTTGTTGAAGCTT | 4860 |
| Jimmy Nardello | TCGGATAGAAGACGTGTTAGAGAATGTTATTGTTTCGGAATGGAGACTTTGTTGTTGAAGCTT | 4860 |
| 10CA 3745-M | TCGGATAGAAGACGTGTTAGAGAATGTTATTGTTTCGACACTTCTTCCGAATGGAGACTTTGTTGTTGAAGCTT | 4860 |
| SBR-99-1193 | TCGGATAGAAGACGTGTTAGAGAATGTTATTGTTTCGGAATGGAGACTTTGTTGTTGAAGCTT | 4860 |
| SBR-99-1299 | TCGGATAGAAGACGTGTTAGAGAATGTTATTGTTTCGGAATGGAGACTTTGTTGTTGAAGCTT | 4860 |
| SBR-99-1300 | TCGGATAGAAGACGTGTTAGAGAATCTTATTGTTTCGGAATGGAGACTTTGTTGTTGAAGCTT | 4860 |
| HAS-30-1017 | TCGGATAGAAGACGTGTTAGAGAATGTTATTGTTTCGGAATGGAGACTTTGTTGTTGAAGCTT | 4860 |
| CCS ORF | TCGGATAGAAGACGTGTTAGAGAATGTTATTGTTTCGGAATGGAGACTTTGTTGTTGAAGCTT | 1278 |
| CCS | S D R R R V R E C Y C F G M E T L L K L | |

FIG. 8 (continued)

| | | |
|---|---|---|
| SBY-99-1273 | GATTTGGAAGGTACTAGGAGAGATTGTTGATGTTGATGCTTTCTTTGATGTTGATCCCAAGTACTGG | 493 |
| SMO-28-1234 | GATTTGGAAGGTACTAGGAGAGATTGTTGATGTTGATGCTTTCTTTGATGTTGATCCCAAGTACTGG | 493 |
| SBY-99-1339 | GATTTGGAAGGTACTAGGAGAGATTGTTGATGTTGATGCTTTCTTTGATGTTGATCCCAAGTACTGG | 493 |
| SBY-99-1296 | GATTTGGAAGGTACTAGGAGAGATTGTTGATGTTGATGCTTTCTTTGATGTTGATCCCAAGTACTGG | 493 |
| SBY-99-1179 | GATTTGGAAGGTACTAGGAGAGATTGTTGATGTTGATGCTTTCTTTGATGTTGATCCCAAGTACTGG | 493 |
| SBY-29-469 | GATTTGGAAGGTACTAGGAGAGATTGTTGATGTTGATGCTTTCTTTGATGTTGATCCCAAGTACTGG | 493 |
| SBY-148-5201 | GATTTGGAAGGTACTAGGAGAGATTGTTGATGTTGATGCTTTCTTTGATGTTGATCCCAAGTACTGG | 493 |
| SBR-27-146 | GATTTGGAAGGTACTAGGAGAGATTGTTTGATGCTTTGATGCTTTCTTTGATGTTGATCCCAAGTACTGG | 4920 |
| Jimmy Nardello | GATTTGGAAGGTACTAGGAGAGATTGTTTGATGCTTTGATGCTTTCTTTGATGTTGATCCCAAGTACTGG | 4920 |
| 10CA 3745-M | GATTTGGAAGGTACTAGGAGAGATTGTTTGATGCTTTGATGCTTTCTTTGATGTTGATCCCAAGTACTGG | 4920 |
| SBR-99-1193 | GATTTGGAAGGTACTAGGAGAGATTGTTTGATGCTTTGATGCTTTCTTTGATGTTGATCCCAAGTACTGG | 4920 |
| SBR-99-1299 | GATTTGGAAGGTACTAGGAGAGATTGTTTGATGCTTTGATGCTTTCTTTGATGTTGATCCCAAGTACTGG | 4920 |
| SBR-99-1300 | GATTTGGAAGGTACTAGGAGAGATTGTTTGATGCTTTGATGCTTTCTTTGATGTTGATCCCAAGTACTGG | 4920 |
| HAS-30-1017 | GATTTGGAAGGTACTAGGAGAGATTGTTTGATGCTTTGATGCTTTCTTTGATGTTGATCCCAAGTACTGG | 4920 |
| CCS ORF | GATTTGGAAGGTACTAGGAGAGATTGTTTGATGCTTTGATGCTTTCTTTGATGTTGATCCCAAGTACTGG | 1338 |
| CCS | D L E G T R R L E D A F F D V D P K Y W | |

FIG. 8 (continued)

| | | |
|---|---|---|
| SBY-99-1273 | CACGGGTTCCTTTCTTCTTCAAGATTGTCTGTCAAAGAACTTGCTGTACTCAGTTTGTACCTT | 553 |
| SMO-28-1234 | CACGGGTTCCTTTCTTCTTCAAGATTGTCTGTCAAAGAACTTGCTGTACTCAGTTTGTACCTT | 553 |
| SBY-99-1339 | CACGGGTTCCTTTCTTCTTCAAGATTGTCTGTCAAAGAACTTGCTGTACTCAGTTTGTACCTT | 553 |
| SBY-99-1296 | CACGGGTTCCTTTCTTCCTTCAAGATTGTCTGTCAAAGAACTTGCTGTACTCAGTTTGTACCTT | 553 |
| SBY-99-1179 | CACGGGTTCCTTTCTTCTTCAAGATTGTCTGTCAAAGAACTTGCTGTACTCAGTTTGTACCTT | 553 |
| SBY-29-469 | CACGGGTTCCTTTCTTCTTCAAGATTGTCTGTCAAAGAACTTGCTGTACTCAGTTTGTACCTT | 553 |
| SBY-148-5201 | CACGGGTTCCTTTCTTCTTCAAGATTGTCTGTCAAAGAACTTGCTGTACTCAGTTTGTACCTT | 553 |
| SBR-27-146 | CACGGGTTCCTTTCTTCTTCAAGATTGTCTGTCAAAGAACTTGCTGTACTCAGTTTGTACCTT | 4980 |
| Jimmy Nardello | CACGGGTTCCTTTCTTCTTCAAGATTGTCTGTCAAAGAACTTGCTGTACTCAGTTTGTACCTT | 4980 |
| 10CA 3745-M | CACGGGTTCCTTTCTTCTTCAAGATTGTCTGTCAAAGAACTTGCTGTACTCAGTTTGTACCTT | 4980 |
| SBR-99-1193 | CACGGGTTCCTTTCTTCTTCAAGATTGTCTGTCAAAGAACTTGCTGTACTCAGTTTGTACCTT | 4980 |
| SBR-99-1299 | CACGGGTTCCTTTCTTCTTCAAGATTGTCTCTCAAAGAACTTGCTGTACTCAGTTTGTACCTT | 4980 |
| SBR-99-1300 | CACGGGTTCCTTTCTTCTTCAAGATTGTCTGTCAAAGAACTTGCTGTACTCAGTTTGTACCTT | 4980 |
| HAS-30-1017 | CACGGGTTCCTTTCTTCTTCAAGATTGTCTGTCAAAGAACTTGCTGTACTCAGTTTGTACCTT | 4980 |
| CCS ORF | CACGGGTTCCTTTCTTCTTCAAGATTGTCTGTCAAAGAACTTGCTGTACTCAGTTTGTACCTT | 1398 |
| CCS | H G F L S S R L S V K E L A V L S L Y L | |

FIG. 8 (continued)

```
SBY-99-1273        TTTGGACATGCCCTCTAATTTGGCTAGGTTGGATATTGTTACAAAGTGCACTGTCCCCTTG  613
SMO-28-1234        TTTGGACATGCCCTCTAATTTGGCTAGGTTGGATATTGTTACAAAGTGCACTGTCCCCTTG  613
SBY-99-1339        TTTGGACATGCCCTCTAATTTGGCTAGGTTGGATATTGTTACAAAGTGCACTGTCCCCTTG  613
SBY-99-1296        TTTGGACATGCCCTCTAATTTGGCTAGGTTGGATATTGTTACAAAGTGCACTGTCCCCTTG  613
SBY-99-1179        TTTGGACATGCCCTCTAATTTGGCTAGGTTGGATATTGTTACAAAGTGCACTGTCCCCTTG  613
SBY-29-469         TTTGGACATGCCCTCTAATTTGGCTAGGTTGGATATTGTTACAAAGTGCACTGTCCCCTTG  613
SBY-148-5201       TTTGGACATGCCCTCTAATTTGGCTAGGTTGGATATTGTTACAAAGTGCACTGTCCCCTTG  613
SBR-27-146         TTTGGACATGCCCTCTAATTTGGCTAGGTTGGATATTGTTACAAAGTGCACTGTCCCCTTG  5040
Jimmy Nardello     TTTGGACATGCCCTCTAATTTGGCTAGGTTGGATATTGTTACAAAGTGCACTGTCCCCTTG  5040
10CA 3745-M        TTTGGACATGCCCTCTAATTTGGCTAGGTTGGATATTGTTACAAAGTGCACTGTCCCCTTG  5040
SBR-99-1193        TTTGGACATGCCCTCTAATTTGGCTAGGTTGGATATTGTTACAAAGTGCACTGTCCCCTTG  5040
SBR-99-1299        TTTGGACATGCCCTCTAATTTGGCTAGGTTGGATATTGTTACAAAGTGCACTGTCCCCTTG  5040
SBR-99-1300        TTTGGACATGCCCTCTAATTTGGCTAGGTTGGATATTGTTACAAAGTGCACTGTCCCCTTG  5040
HAS-30-1017        TTTGGACATGCCCTCTAATTTGGCTAGGTTGGATATTGTTACAAAGTGCACTGTCCCCTTG  5040
CCS ORF            TTTGGACATGCCCTCTAATTTGGCTAGGTTGGATATTGTTACAAAGTGCACTGTCCCCTTG  1458
CCS                  F  G  H  A  S  N  L  A  R  L  D  I  V  T  K  C  T  V  P  L
```

FIG. 8 (continued)

| | | |
|---|---|---|
| SBY-99-1273 | GTTAAACTGCTGGGCAATCTAGCAATAGAGAGCCCTTTGAATTAATATGATAGTTTTGAAG | 673 |
| SMO-28-1234 | GTTAAACTGCTGGGCAATCTAGCAATAGAGAGCCCTTTGAATTAATATGATAGTTTTGAAG | 673 |
| SBY-99-1339 | GTTAAACTGCTGGGCAATCTAGCAATAGAGAGCCCTTTGAATTAATATGATAGTTTTGAAG | 673 |
| SBY-99-1296 | GTTAAACTGCTGGGCAATCTAGCAATAGAGAGCCCTTTGAATTAATATGATAGTTTTGAAG | 673 |
| SBY-99-1179 | GTTAAACTGCTGGGCAATCTAGCAATAGAGAGCCCTTTGAATTAATATGATAGTTTTGAAG | 673 |
| SBY-29-469 | GTTAAACTGCTGGGCAATCTAGCAATAGAGAGCCCTTTGAATTAATATGATAGTTTTGAAG | 673 |
| SBY-148-5201 | GTTAAACTGCTGGGCAATCTAGCAATAGAGAGCCCTTTGAATTAATATGATAGTTTTGAAG | 5100 |
| SBR-27-146 | GTTAAACTGCTGGGCAATCTAGCAATAGAGAGCCCTTTGAATTAATATGATAGTTTTGAAG | 5100 |
| Jimmy Nardello | GTTAAACTGCTGGGCAATCTAGCAATAGAGAGCCCTTTGAATTAATATGATAGTTTTGAAG | 5100 |
| 10CA 3745-M | GTTAAACTGCTGGGCAATCTAGCAATAGAGAGCCCTTTGAATTAATATGATAGTTTTGAAG | 5100 |
| SBR-99-1193 | GTTAAACTGCTGGGCAATCTAGCAATAGAGAGCCCTTTGAATTAATATGATAGTTTTGAAG | 5100 |
| SBR-99-1299 | GTTAAACTGCTGGGCAATCTAGCAATAGAGAGCCCTTTGAATTAATATGATAGTTTTGAAG | 5100 |
| SBR-99-1300 | GTTAAACTGCTGGGCAATCTAGCAATAGAGAGCCCTTTGAATTAATATGATAGTTTTGAAG | 5100 |
| HAS-30-1017 | GTTAAACTGCTGGGCAATCTAGCAATAGAGAGCCCTTTGA | 1497 |
| CCS ORF | | |
| CCS | V K L G N L A I E S L * | |

FIG. 8 (continued)

| | | |
|---|---|---|
| SBY-99-1273 | CACTGCTTTCATTTTAATTTCTTAGGTTATTTTCATCTTTTTATCAATTGCAAAAGTGAAAC | 733 |
| SMO-28-1234 | CACTGCTTTCATTTTAATTTCTTAGGTTATTTTCATCTTTTTATCAATTGCAAAAGTGAAAC | 733 |
| SBY-99-1339 | CACTGCTTTCATTTTAATTTCTTAGGTTATTTTCATCTTTTTATCAATTGCAAAAGTGAAAC | 733 |
| SBY-99-1296 | CACTGCTTTCATTTTAATTTCTTAGGTTATTTTCATCTTTTTATCAATTGCAAAAGTGAAAC | 733 |
| SBY-99-1179 | CACTGCTTTCATTTTAATTTCTTAGGTTATTTTCATCTTTTTATCAATTGCAAAAGTGAAAC | 733 |
| SBY-29-469 | CACTGCTTTCATTTTAATTTCTTAGGTTATTTTCATCTTTTTATCAATTGCAAAAGTGAAAC | 733 |
| SBY-148-5201 | CACTGCTTTCATTTTAATTTCTTAGGTTATTTTCATCTTTTTATCAATTGCAAAAGTGAAAC | 733 |
| SBR-27-146 | CACTGCTTTCATTTTAATTTCTTAGGTTATTTTCATCTTTTTATCAATTGCAAAAGTGAAAC | 5160 |
| Jimmy Mardello | CACTGCTTTCATTTTAATTTCTTAGGTTATTTTCATCTTTTTATCAATTGCAAAAGTGAAAC | 5160 |
| 10CA 3745-M | CACTGCTTTCATTTTAATTTCTTAGGTTATTTTCATCTTTTCATCAATTGCAAAAGTGAAAC | 5160 |
| SBR-99-1193 | CACTGTTTTCATTTTAATTTCTTAGGTTATTTTCATCTTTTCTCCAATTGCAAAAGTGAAAC | 5160 |
| SBR-99-1299 | CACTGTTTTCATTTTAATTTCTTAGGTTATTTTCATCTTTTCTCCAATTGCAAAAGTGAAAC | 5160 |
| SBR-99-1300 | CACTGTTTTCATTTTAATTTCTTAGGTTATTTTCATCTTTTCTCCAATTGCAAAAGTGAAAC | 5160 |
| HAS-30-1017 | CACTGTTTTCATTTTAATTTCTTAGGTTATTTTCATCTTTTCTCCAATTGCAAAAGTGAAAC | 5160 |
| | NCANN0091135170 * NCANN0091113170 | |

FIG. 8 (continued)

| | | |
|---|---|---|
| SBY-99-1273 | AAAAGCTATACACATTGTCATCGTTGTTCAAACTCAGACAAGTTTGCCTAGCTCTATGTA | 793 |
| SMO-28-1234 | AAAAGCTATACACATTGTCATCGTTGTTCAAACTCAGACAAGTTTGCCTAGCTCTATGTA | 793 |
| SBY-99-1339 | AAAAGCTATACACATTGTCATCGTTGTTCAAACTCAGACAAGTTTGCCTAGCTCTATGTA | 793 |
| SBY-99-1296 | AAAAGCTATACACATTGTCATCGTTGTTCAAACTCAGACAAGTTTGCCTAGCTCTATGTA | 793 |
| SBY-99-1179 | AAAAGCTATACACATTGTCATCGTTGTTCAAACTCAGACAAGTTTGCCTAGCTCTATGTA | 793 |
| SBY-29-469 | AAAAGCTATACACATTGTCATCGTTGTTCAAACTCAGACAAGTTTGCCTAGCTCTATGTA | 793 |
| SBY-148-5201 | AAAAGCTATACACATTGTCATCGTTGTTCAAACTCAGACAAGTTTGCCTAGCTCTATGTA | 793 |
| SBR-27-146 | AAAAGCTATACACATTGTCATCGTTGTTCAAACTCAGACAAGTTTGCCTAGCTCTATGTA | 5220 |
| Jimmy Mardello | AAAAGCTATACACATTGTCATCGTTGTTCAAACTCAGACAAGTTTGCCTAGCTCTATGTA | 5220 |
| 10CA 3745-M | AAAAGCTATACACATTGTCATCGTTGTTCAAACTCAGACAAGTTTGCCTAGCTCTATGTA | 5220 |
| SBR-99-1193 | AAAAGCTATACACATTGTCATCGTTGTTCAAACTCAGACAAGTTTGCCTAGCTCTATGTA | 5220 |
| SBR-99-1299 | AAAAGCTATACACATTGTCATCGTTGTTCAAACTCAGACAAGTTTGCCTAGCTCTATGTA | 5220 |
| SBR-99-1300 | AAAAGCTATACACATTGTCATCGTTGTTCAAACTCAGACAAGTTTGCCTAGCTCTATGTA | 5220 |
| HAS-30-1017 | AAAAGCTATACACATTGTCATCGTTGTTCAAACTCAGACAAGTTTGCCTAGCTCTATGTA | 5220 |

| | | |
|---|---|---|
| SBY-99-1273 | TTTATCCTTAACATATGTATTCATCAAATTCGAAATATACAATGTATGGTTGTCGATGCA | 853 |
| SMO-28-1234 | TTTATCCTTAACATATGTATTCATCAAATTCGAAATATACAATGTATGGTTGTCGATGCA | 853 |
| SBY-99-1339 | TTTATCCTTAACATATGTATTCATCAAATTCGAAATATACAATGTATGGTTGTCGATGCA | 853 |
| SBY-99-1296 | TTTATCCTTAACATATGTATTCATCAAATTCGAAATATACAATGTATGGTTGTCGATGCA | 853 |
| SBY-99-1179 | TTTATCCTTAACATATGTATTCATCAAATTCGAAATATACAATGTATGGTTGTCGATGCA | 853 |
| SBY-29-469 | TTTATCCTTAACATATGTATTCATCAAATTCGAAATATACAATGTATGGTTGTCGATGCA | 853 |
| SBY-148-5201 | TTTATCCTTAACATATGTATTCATCAAATTCGAAATATACAATGTATGGTTGTCGATGCA | 853 |
| SBR-27-146 | TTTATCCTTAACATATGTATTCATCAAATTCGAAATATACAATGTATGGTTGTCGATGCA | 5280 |
| Jimmy Mardello | TTTATCCTTAACATATGTATTCATCAAATTCGAAATATACAATGTATGGTTGTCGATGCA | 5280 |
| 10CA 3745-M | TTTATCCTTAACATATGTATTCATCAAATTCGAAATATACAATGTATGGTTGTCGATGCA | 5280 |
| SBR-99-1193 | TTTATCCTTAACATATGTATTCATCAAATTCGAAATATACAATG-----------CA | 5266 |
| SBR-99-1299 | TTTATCCTTAACATATGTATTCATCAAATTCGAAATATACAATG-----------CA | 5266 |
| SBR-99-1300 | TTTATCCTTAACATATGTATTCATCAAATTCGAAATATACAATG-----------CA | 5266 |
| HAS-30-1017 | TTTATCCTTAACATATGTATTCATCAAATTCGAAATATACAATG-----------CA | 5266 |

************ NCAN009113970

FIG. 8 (continued)

| | | |
|---|---|---|
| SBY-99-1273 | TTGGACAAAAGTATAGAGAGCCACAATCTGATACCAAGTCTGATATTTGGAAGCACTGGCTAA | 913 |
| SMO-28-1234 | TTGGACAAAAGTATAGAGAGCCACAATCTGATACCAAGTCTGATATTTGGAAGCACTGGCTAA | 913 |
| SBY-99-1339 | TTGGACAAAAGTATAGAGAGCCACAATCTGATACCAAGTCTGATATTTGGAAGCACTGGCTAA | 913 |
| SBY-99-1296 | TTGGACAAAAGTATAGAGAGCCACAATCTGATACCAAGTCTGTATTTGGAAGCACTGGCTAA | 913 |
| SBY-99-1179 | TTGGACAAAAGTATAGAGAGCCACAATCTGATACCAAGTCTGTATTTGGAAGCACTGGCTAA | 913 |
| SBY-29-469 | TTGGACAAAAGTATAGAGAGCCACAATCTGATACCAAGTCTGTATTTGGAAGCACTGGCTAA | 913 |
| SBY-148-5201 | TTGGACAAAAGTATAGAGAGCCACAATCTGATACCAAGTCTGTATTTGGAAGCACTGGCTAA | 913 |
| SBR-27-146 | TTGGACAAAAGTATAGAGAGCCACAATCTGATACCAAGTCTGTATTTGGAAGCACTGGCTAA | 5340 |
| Jimmy Nardello | TTGGACAAAAGTATAGAGAGCCACAATCTGATACCAAGTCTGTATTTGGAAGCACTGGCTAA | 5340 |
| 10CA 3745-M | TTGGACAAAAGTATAGAGAGCCACAATCCGATACCAAGTCTGTATTTGGAAGCACTGGCTAA | 5340 |
| SBR-99-1193 | TTGGACAAAAGTATAGAGAGCCACAATCCGATACCAAGTCTGTATTTGGAACCACTCTCTAA | 5326 |
| SBR-99-1299 | TTGGACAAAAGTATAGAGAGCCACAATCCGATACCAAGTCTGTATTTGGAAGCACTGTCTAA | 5326 |
| SBR-99-1300 | TTGGACAAAAGTATAGAGAGCCACAATCCGATACCAAGTCTGATATTTGGAAGCACTCTCTAA | 5326 |
| HAS-30-1017 | TTGGACAAAAGTATAGAGAGCCACAATCTGATACCAAGTCTGTATTTGGAAGCACAGGCTAA | 5326 |
| | * | |
| | NCANN009113370 | NCANN009113971 |
| | | NCANN009113371 |

FIG. 8 (continued)

| | | |
|---|---|---|
| SBY-99-1273 | TTGTTATGGTTACCAAACACTTTGAATTGGCTGGATAAT----AACAGGAACTTTATGTT | 969 |
| SMO-28-1234 | TTGTTATGGTTACCAAACACTTTGAATTGGCTGGATAAT----AACAGGAAATTTATGTT | 969 |
| SBY-99-1339 | TTGTTATGGTTACCAAACACTTTGAATTGGCTGGATAAT----AACAGGAAATTTATGTT | 969 |
| SBY-99-1296 | TTGTTATGGTTACCAAACACTTTGAATTGGCTGGATAAT----AACAGGAAATTTATGTT | 969 |
| SBY-99-1179 | TTGTTATGGTTACCAAACACTTTGAATTGGCTGGATAAT----AACAGGAAATTTATGTT | 969 |
| SBY-29-469 | TTGTTATGGTTACCAAACACTTTGAATTGGCTGGATAAT----AACAGGAAATTTATGTT | 969 |
| SBY-148-5201 | TTGTTATGGTTACCAAACACTTTGAATTGGCTGGATAAT----AACAGGAAATTTATGTT | 5396 |
| SBR-27-146 | TTGTTATGGTTACCAAACACTTTGAATTGGCTGGATAAT----AACAGGAAATTTATGTT | 5396 |
| Jimmy Nardello | TTGTTATGGTTACCAAACACTTTGAATTGGCTGGATAAT----AACAGGAAATTTATGTT | 5396 |
| 10CA 3745-M | TTGTTATGGTTACCAAACACTTTGAATTGGCTGGATAAT----AACAGGAAATTTATGTT | 5386 |
| SBR-99-1193 | TTGTTATGGTTACCAAACACTTTGAATTGGCTGGATAATAACAAACAGGAAATTTATGTT | 5386 |
| SBR-99-1299 | TTGTTATGGTTACCAAACACTTTGAATTGGCTGGATAATAACAAACAGGAAATTTATGTT | 5386 |
| SBR-99-1300 | TTGTTATGGTTACCAAACACTTTGAATTGGCTGGATAATAACAAACAGGAAATTTATGTT | 5386 |
| HAS-30-1017 | TTGTTATGGTTACCAAACACTTTGAATTGGCTGGATAATAACAAACAGGAAATTTATGTT | 5386 |
| | ****                                  *                     | |

NCANN009114170
NCANN009114370

FIG. 8 (continued)

| | | |
|---|---|---|
| SBY-99-1273 | ATTAATCATTAACAGCAAATTGGGAAAAGCAAGAATTATTAGGAAAGTTAATATATAGTGTCT | 1029 |
| SMO-28-1234 | ATTAATCATTAACAGCAAATTGGGAAAAGCAAGAATTATTAGGAAAGTTAATATATAGTGTCT | 1029 |
| SBY-99-1339 | ATTAATCATTAACAGCAAATTGGGAAAAGCAAGAATTATTAGGAAAGTTAATATATAGTGTCT | 1029 |
| SBY-99-1296 | ATTAATCATTAACAGCAAATTGGGAAAAGCAAGAATTATTAGGAAAGTTAATATATAGTGTCT | 1029 |
| SBY-99-1179 | ATTAATCATTAACAGCAAATTGGGAAAAGCAAGAATTATTAGGAAAGTTAATATATAGTGTCT | 1029 |
| SBY-29-469 | ATTAATCATTAACAGCAAATTGGGAAAAGCAAGAATTATTAGGAAAGTTAATATATAGTGTCT | 1029 |
| SBY-148-5201 | ATTAATCATTAACAGCAAATTGGGAAAAGCAAGAATTATTAGGAAAGTTAATATATAGTGTCT | 5456 |
| SBR-27-146 | ATTAATCATTAACAGCAAATTGGGAAAAGCAAGAATTATTAGGAAAGTTAATATATAGTGTCT | 5456 |
| Jimmy Nardello | ATTAATCATTAACAGCAAATTGGGAAAAGCAAGAATTATTAGGAAAGTTAATATATAGTGTCT | 5456 |
| 10CA_3745-M | ATTAATCATTAACAGCAAATTGGGAAAAGCAAGAATTATTAGGAAAGTTAATATATAGTGTCT | 5446 |
| SBR-99-1193 | TTTAATCATTAACAGCAAATTGGGAAAAGCAAGAATTATTAGGAAAGTTAATATATAGTGTCT | 5446 |
| SBR-99-1299 | TTTAATCATTAACAGCAAATTGGGAAAAGCAAGAATTATTAGGAAAGTTAATATATAGTGTCT | 5446 |
| SBR-99-1300 | TTTAATCATTAACAGCAAATTGGGAAAAGCAAGAATTATTAGGAAAGTTAATATATAGTGTCT | 5446 |
| HAS-30-1017 | TTTAATCATTAACAGCAAATTGGGAAAAGCAAGAATTATTAGGAAAGTTAATATATAGTGTCT | 5446 |
| NCANN00513431 | * | |

FIG. 8 (continued)

```
SBY-99-1273      TGGTTATTCTAATGGAGTGGGTTATGCAAATTAAGTTCCCTTATCAAAAGTTTGGTTTATG 1089
SMO-28-1234      TGGTTATTCTAATGGAGTGGGTTATGCAAATTAAGTTCCCTTATCAAAAGTTTGGTTTATG 1089
SBY-99-1339      TGGTTATTCTAATGGAGTGGGTTATGCAAATTAAGTTCCCTTATCAAAAGTTTGGTTTATG 1089
SBY-99-1296      TGGTTATTCTAATGGAGTGGGTTATGCAAATTAAGTTCCCTTATCAAAAGTTTGGTTTATG 1089
SBY-99-1179      TGGTTATTCTAATGGAGTGGGTTATGCAAATTAAGTTCCCTTATCAAAAGTTTGGTTTATG 1089
SBY-29-469       TGGTTATTCTAATGGAGTGGGTTATGCAAATTAAGTTCCCTTATCAAAAGTTTGGTTTATG 1089
SBY-148-5201     TGGTTATTCTAATGGAGTGGGTTATGCAAATTAAGTTCCCTTATCAAAAGTTTGGTTTATG 1089
SBR-27-146       TGGTTATTCTAATGGAGTGGGTTATGCAAATTAAGTTCCCTTATCAAAAGTTTGGTTTATG 5516
Jimmy Nardello   TGGTTATTCTAATGGAGTGGGTTATGCAAATTAAGTTCCCTTATCAAAAGTTTGGTTTATG 5516
10CA_3745-M      TGGTTATTCTAATGGAGTGGGTTATGCAAATTAAGTTCCCTTATCAAAAGTTTGGTTTATG 5516
SBR-99-1193      TGGTTATTCTAATGGAGTGGGTTATGCAAATTAAGTTCCCTTATCAAAAGTTTGGTTTATG 5506
SBR-99-1299      TGGTTATTCTAATGGAGTGGGTTATGCAAATTAAGTTCCCTTATCAAAAGTTTGGTTTATG 5506
SBR-99-1300      TGGTTATTCTAATGGAGTGGGTTATGCAAATTAAGTTCCCTTATCAAAAGTTTGGTTTATG 5506
HAS-30-1017      TGGTTATTCTAATGGAGTGGGTTATGCAAATTAAGTTCCCTGTCAAAAGTTTGGTTTATG 5506
                                                          *
NCANN009113571

| | | |
|---|---|---|
| SBY-99-1273 | AACTGCTCCACTCGTGTCCCTCTTAAATCCAACATGTACCACCAAAGAACT | 1149 |
| SMO-28-1234 | AACTGCTCCACTCGTGTCCCTCTTAAATCCAACATGTACCACCAAAGAACT | 1149 |
| SBY-99-1339 | AACTGCTCCACTCCTCGTGTCCCTCTTAAATCCAACATGTACCACCAAAGAACT | 1149 |
| SBY-99-1296 | AACTGCTCCACTCGTGTCCCTCTTAAATCCAACATGTACCACCAAAGAACT | 1149 |
| SBY-99-1179 | AACTGCTCCACTCGTGTCCCTCTTAAATCCAACATGTACCACCAAAGAACT | 1149 |
| SBY-29-469 | AACTGCTCCACTCGTGTCCCTCTTAAATCCAACATGTACCACCAAAGAACT | 1149 |
| SBY-148-5201 | AACTGCTCCACTCGTGTCCCTCTTAAATCCAACATGTACCACCAAAGAACT | 1149 |
| SBR-27-146 | AACTGCTCCACTCGTGTCCCTCTTAAATCCAACATGTACCACCAAAGAACT | 5576 |
| Jimmy Nardello | AACTGCTCCACTCGTGTCCCTCTTAAAAGCCTTAAATCCAACATGTACCACCAAAGAACT | 5576 |
| 10CA 3745-M | AACTGCTCCACTCGTGTCCCTCTTAAAAGCCTTAAATCCAACATGTACCACCAAAGAACT | 5576 |
| SBR-99-1193 | AACTGCTCACTCTTGTCCCTCTTAAAAGCCTTAAATCCAACATGTACCACCAAAGAATT | 5566 |
| SBR-99-1299 | AACTGCTCCACTCTTGTCCCTCTTAAAAGCCTTAAATCCAACATGTACCACCAAAGAATT | 5566 |
| SBR-99-1300 | AACTGCTCCACTCGTGTCCCTCTTAAAAGCCTTAAATCCAACATGTACCACCAAAGAATT | 5566 |
| HAS-30-1017 | AACTGCTCCACTCGTGTCCCTCTTAAAAGCCTTAAATCCAACATGTACCACCAAAGAATT | 5566 |

NCANN00911317
*

NCAMN00911337 2
*

| | | |
|---|---|---|
| SBY-99-1273 | GAGCTGCTCCATCAGATCCTTTGAGAATGTTAATATGTTATTTAAATGAAGGACTGAATG | 1209 |
| SMO-28-1234 | GAGCTGCTCCATCAGATCCTTTGAGAATGTTAATATGTTATTTAAATGAAGGACTGAATG | 1209 |
| SBY-99-1339 | GAGCTGCTCCATCAGATCCTTTGAGAATGTTAATATGTTATTTAAATGAAGGACTGAATG | 1209 |
| SBY-99-1296 | GAGCTGCTCCATCAGATCCTTTGAGAATGTTAATATGTTATTTAAATGAAGGACTGAATG | 1209 |
| SBY-99-1179 | GAGCTGCTCCATCAGATCCTTTGAGAATGTTAATATGTTATTTAAATGAAGGACTGAATG | 1209 |
| SBY-29-469 | GAGCTGCTCCATCAGATCCTTTGAGAATGTTAATATGTTATTTAAATGAAGGACTGAATG | 1209 |
| SBY-148-5201 | GAGCTGCTCCATCAGATCCTTTGAGAATGTTAATATGTTATTTAAATGAAGGACTGAATG | 1209 |
| SBR-27-146 | GAGCTGCTCCATCAGATCCTTTGAGAATGTTAATATGTTATTTAAATGAAGGACTGAATG | 5636 |
| Jimmy Nardello | GAGCTGCTCCATCAGATCCTTTGAGAATGTTAATATGTTATTTAAATGAAGGACTGAATG | 5636 |
| 10CA 3745-M | GAGCTGCTCCATCAGATCCTTTGAGAATGTTAATATGTTATTTAAATGAAGGACTGAATG | 5636 |
| SBR-99-1193 | GAGCTGCTCCATCAGATCCTTTGAGAATGTTAATATGTTATTTAAATGAAGGACTGAATG | 5626 |
| SBR-99-1299 | GAGCTGCTCCATCAGATCCTTTGAGAATGTTAATATGTTATTTAAATGAAGGACTGAATG | 5626 |
| SBR-99-1300 | GAGCTGCTCCATCAGATCCTTTGAGAATGTTAATATGTTATTTAAATGAAGGACTGAATG | 5626 |
| HAS-30-1017 | GAGCTGCTCCATCAGATCCTTTGAGAATGTTAATATGTTATTTAAATGAAGGACTGAATG | 5626 |

FIG. 8 (continued)

SELECTION OF MATURE FRUIT COLOR IN PEPPER PLANTS

REFERENCE TO RELATED APPLICATIONS

This application is a continuation of U.S. application Ser. No. 15/643,317, filed Jul. 6, 2017, which is a divisional of U.S. application Ser. No. 14/304,722, filed Jun. 13, 2014, now U.S. Pat. No. 9,723,797, which claims the benefit of U.S. provisional application No. 61/863,765, filed Aug. 8, 2013, and U.S. provisional application No. 61/838,094, filed Jun. 21, 2013, each of which is herein incorporated by reference in its entirety.

BACKGROUND OF THE INVENTION

1. Incorporation of Sequence Listing

The sequence listing that is contained in the file named "SEMB011US_ST25.txt", which is 171 kilobytes as measured in the Microsoft Windows operating system and was created on Jun. 13, 2014, is filed electronically herewith and incorporated herein by reference.

2. Field of the Invention

The present invention relates to the field of plant breeding and, more specifically, to the development of pepper plants displaying a desired mature fruit color.

3. Description of Related Art

The goal of vegetable breeding is to produce varieties displaying one or more desirable traits, such as a desired mature fruit color. Pepper plants (*Capsicum* sp.) may display, for instance, a mature fruit color of red, red-orange, orange, or yellow as a result of the function of pigment biosynthetic pathway(s) which produce pigments such as carotenes and xanthophylls.

SUMMARY OF THE INVENTION

In one aspect, the invention provides a package of pepper fruits comprising at least two different colors of pepper fruits selected from the group consisting of: red, yellow, orange, and red-orange, wherein the peppers are grown from near isogenic pepper varieties. In one embodiment, the package comprises from about 1 to about 5 pepper fruits per color. In further embodiments, the pepper varieties are hybrid varieties. The package may contain, for example, at least three or at least four different colors of pepper fruits. The package may also comprise a green pepper fruit. In certain embodiments, the peppers are grown from at least two hybrid varieties that share a parent line. The hybrid varieties may also all share a parent line. In still further embodiments, the pepper varieties are *Capsicum annuum, C. baccatum, C. chinense, C. frutescens*, or *C. pubescens* varieties. In another embodiment, the pepper varieties are sweet peppers.

In another aspect, the invention provides a method of producing pepper fruits comprising: growing at least two near isogenic pepper lines that collectively comprise functional and non-functional Ccs and Ze alleles, and harvesting pepper fruit therefrom, wherein the pepper fruit are of at least two different colors selected from the group consisting of: red, yellow, orange, red-orange, and green. The method can further comprise, in one embodiment, packaging the pepper fruit in a single package, wherein the pepper fruit are of at least two different colors selected from the group consisting of: red, yellow, orange, red-orange, and green.

In still another aspect, the invention provides a container comprising seeds of at least two near isogenic pepper varieties, wherein the pepper varieties produce fruit of different fruit colors, and wherein the fruit colors are selected from the group consisting of: red, yellow, orange, and red-orange. In one embodiment, the container is defined as comprising seeds of at least three near isogenic pepper varieties that produce fruit of different fruit colors. In another embodiment, the container comprises seeds of at least four near isogenic pepper varieties that produce fruit of different fruit colors.

In still yet another aspect, the invention provides a method of producing pepper seed comprising: (a) producing a set of near isogenic inbred pepper lines that collectively comprise functional and non-functional Ccs and Ze alleles; (b) crossing said pepper lines to produce seed of near isogenic hybrid plants that comprise combinations of said alleles that result in red, yellow and orange fruit. In one embodiment of the method, producing a set of near isogenic lines comprises producing a plant that has been inbred but segregates for a Ccs or Ze allele. Producing a set of near isogenic lines may comprise, for example, producing a plant that has been inbred but segregates for Ccs and Ze alleles. In the method, the plant that has been inbred may be selfed for three or more generations. In certain embodiments of the method, producing a set of near isogenic inbred pepper lines comprises marker assisted selection for a Ccs or Ze allele. In other embodiments, producing a set of near isogenic inbred pepper lines comprises marker assisted selection for Ccs and Ze alleles. Marker assisted selection may comprise, in specific embodiments, detecting a deletion in a Ccs gene or the absence thereof. Marker assisted selection may also or alternatively comprise detecting a single nucleotide polymorphism in a Ze gene or the absence thereof. The near isogenic inbred pepper lines may, in one example, be homozygous for said Ccs and Ze alleles. In still further embodiments, the pepper lines are selected from the pepper species consisting of *Capsicum annuum, C. baccatum, C. chinense, C. frutescens*, and *C. pubescens*. In other embodiments, the pepper lines are sweet peppers.

In still yet another aspect, the invention provides a method of selecting a pepper plant for fruit color genotype comprising: (a) detecting the presence or absence of a polymorphism in the Zeaxanthin epoxidase (Ze) gene conferring said fruit color; and (b) selecting the plant based on the presence or absence of said polymorphism. In the method, detecting the presence or absence of a polymorphism in the Zeaxanthin epoxidase (Ze) gene may comprise detecting a genetic marker in linkage disequilibrium with said polymorphism. In another embodiment, detecting the presence or absence of a polymorphism in the Zeaxanthin epoxidase (Ze) gene comprises detecting the presence or absence of a single nucleotide polymorphism that is causative for said fruit color. In other embodiments, the method comprises detection of at least one genetic marker selected from the group consisting of: NE0235373, NE0240266, NE0239621, NE0240354, and NE0241248. In another embodiment, the method further comprises (c) crossing the selected plant from step (b) with a second pepper plant. In still other embodiments, the plant is a *Capsicum annuum* plant, and may be a sweet pepper plant.

BRIEF DESCRIPTION OF DRAWINGS

FIG. 5: Alignment of the sequences of the Ze gene derived from pepper line CM334 (line labeled "contig36343", SEQ ID NO:99), representative yellow (SEQ ID NO:96) and orange (SEQ ID NO:97) pepper lines, and the predicted coding sequence (SEQ ID NO:98), with marker locations shown.

FIG. 8: Alignment of Ccs sequences from 14 pepper lines (SEQ ID NOs:40-53).

DETAILED DESCRIPTION OF THE INVENTION

The invention provides methods and compositions relating to pepper (*Capsicum* spp., such as *C. annuum*) plants, and pepper plant parts, including seeds and fruit, and derivatives of such pepper plants/lines to allow for identification of pepper plants and production of nearly isogenic varieties which produce mature fruit of a desired color or colors, such as red, red-orange, orange, and/or yellow fruit.

Thus, in one aspect, the novel identification of a genetic trait allowing for orange mature fruit color in peppers (*Capsicum* spp.) as residing at the "Ze" locus encoding Zeaxanthin Epoxidase ("ZE" or "ZEP") on pepper chromosome 2, is disclosed herein. In another aspect, a deletion in the Capsanthin-Capsorubin Synthase (CCS) gene (termed "Ccs") is identified as a causal mutation leading to non-red mature pepper fruit color, allowing for use of genetic markers linked to a known allele of the Ccs gene via marker assisted selection ("MAS") or marker assisted backcrossing ("MABC"), when breeding for diverse mature fruit color in pepper plants. Pepper plants comprising a genetic marker linked to a known allele of the CCS gene may thus be utilized to breed pepper plants which display a desired mature fruit color, including red, orange, red-orange, and yellow. Further, use of both Ze and Ccs-encoded traits, and associated genetic markers, allows for production of collections of pepper lines and plants which produce fruit displaying desired mature fruit color, including lines which produce mature fruit displaying one or more desired mature fruit colors such as red, red-orange, orange, and yellow, and any combination thereof.

Figure 1:
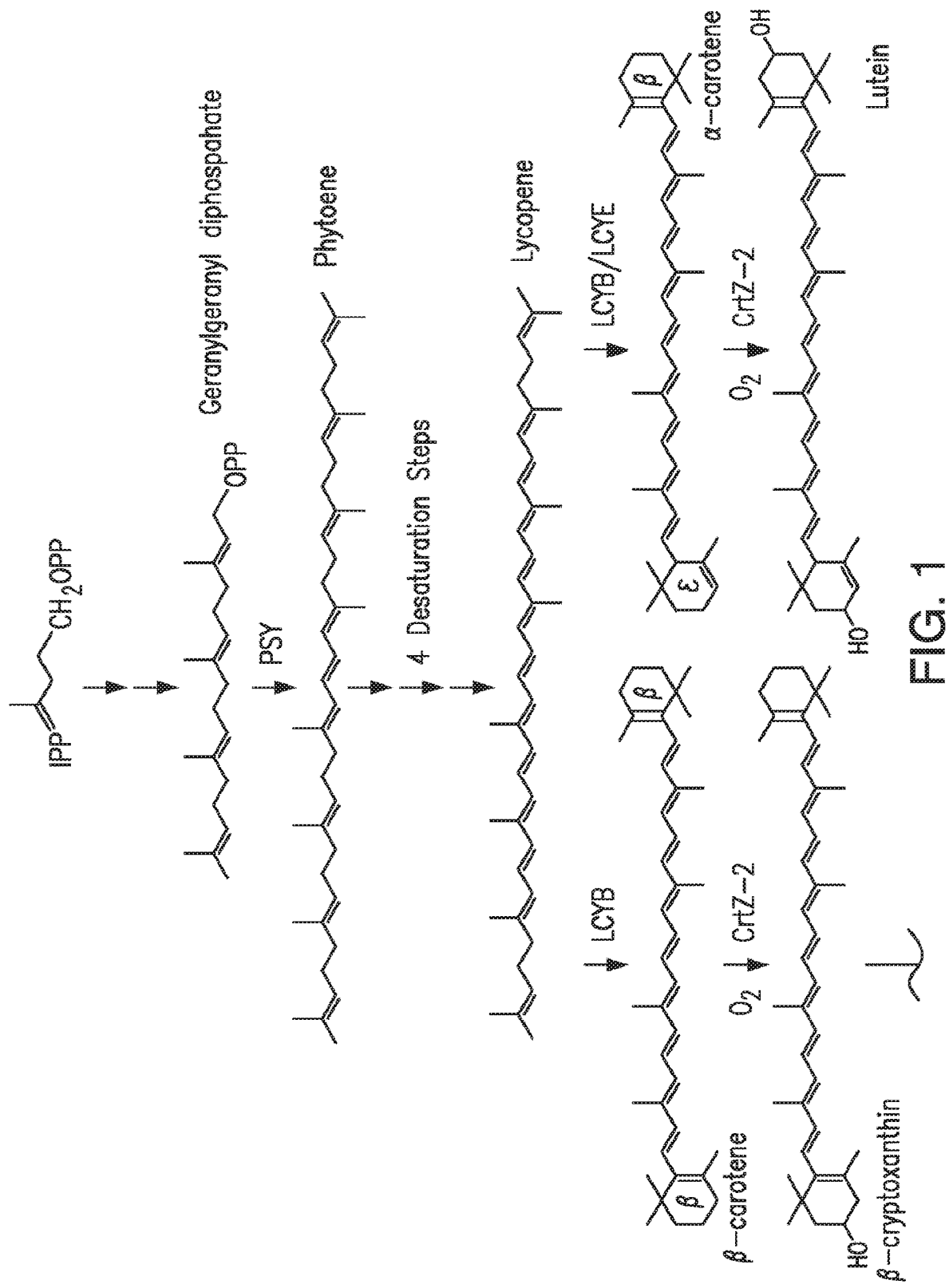
FIG. 1: Schematic presentation of the carotene and xanthophyll biosynthetic pathway in *Capsicum* sp. (from Guzman et al., *Plant Science* 179:49-59, 2010).
Figure 1:
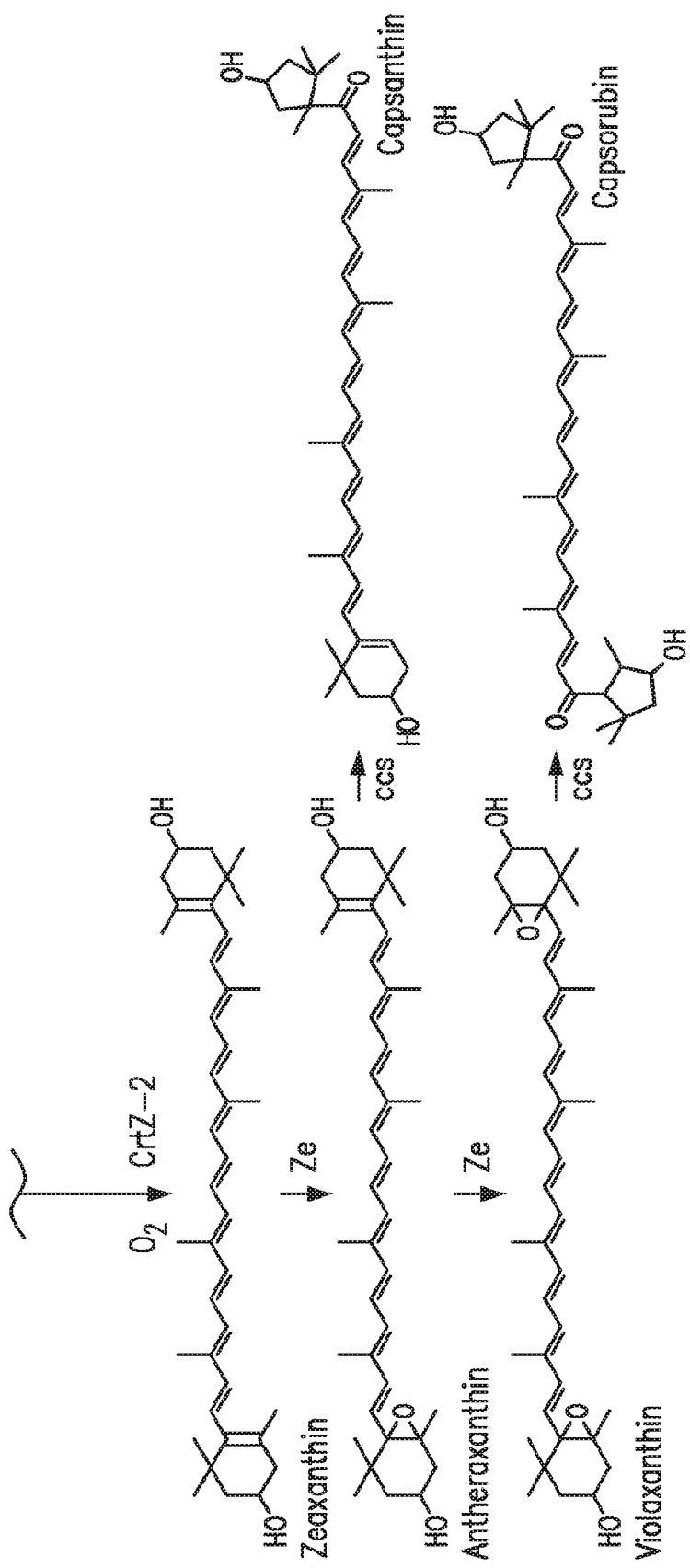

Plants with a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, these plants without a functional CCS protein have yellow or orange fruits. Carotenoids are largely responsible for the phenotypic colors of red, yellow, and orange pepper fruits. Due to the extensive conjugated double bond network and delocalized π-electrons, carotenoids absorb light in the visible range (400-500 nm) resulting in intense coloration of yellow, orange, and red (Britton, *FASEB J.* 9:1551-1558, 1995). The predominate carotenoids found in pepper fruits can be grouped according to their visual color class, which is based upon the number of conjugated double bonds. The major red carotenoids are capsanthin and capsorubin and absorb UV in the 470-475 nm range. The major orange carotenoids are zeaxanthin, β-carotene, and β-cryptoxanthin and absorb UV in the 450-455 nm range. The major yellow carotenoids are violaxanthin, antheraxanthin, and lutein and absorb UV in the 440-445 nm range. Thus, changes in the carotenoid profile have the potential to alter phenotypic fruit color.

Several enzymatic steps are required for the biosynthesis of carotenoids. Perturbations in the biosynthetic pathway can alter the carotenoid profile, ultimately resulting in phenotypic changes in fruit color. Capsanthin-Capsorubin Synthase and Zeaxanthin Epoxidase represent critical junctions in the pepper carotenoid biosynthetic pathway (FIG. 1). CCS is responsible for the formation of the red carotenoids capsanthin and capsorubin. ZEP catalyzes the epoxidation of the terminal 3-hydroxy-β-ionone ring structure of zeaxanthin, resulting in the formation of the di-epoxide violaxanthin via the mono-epoxide antheraxanthin. Both antheraxanthin and violaxanthin, in turn, serve as substrates for the CCS enzyme. Thus, the presence or absence of a fully functional CCS and/or ZEP enzyme impacts the biosynthesis of the red and yellow carotenoids, resulting in a change in carotenoid profile in mature fruit, and corresponding changes in fruit color.

Previously, the genetic basis of orange color in habanero peppers (*Capsicum chinense*) was reported to be due to a mutation in the gene encoding phytoene synthase ("Psy;" Thorup et al., *PNAS* 97:11192-11197, 2000). However, the orange line used in creating a polymorphic population for that mapping study was a habanero type pepper (*Capsicum chinense*), and the phytoene synthase gene was not known to contribute functional polymorphism affecting orange fruit color in elite *Capsicum annuum* peppers. Other research has implicated another carotenoid biosynthetic gene, encoding β-Carotene Hydroxylase, as involved in specifying fruit color (e.g. Borovsky et al. *TAG* 126:557-565, 2013). Thus, the identification of functional polymorphism (i.e. causal single nucleotide polymorphisms or "SNPs") in the gene encoding Zeaxanthin epoxidase correlating with a change in mature fruit color in *C. annuum* is surprising and unexpected. Pepper plants which produce, for instance, fruit with orange mature fruit color may thus be identified and bred using the presently disclosed genetic markers and trait source(s). Identification of causal polymorphisms in the Ccs gene provides further compositions and methods for pepper breeding, and may be used separately or in conjunction with disclosed Ze genetic markers and traits, to produce pepper plants displaying a mature fruit color of interest.

Commercial peppers are primarily of the species *Capsicum annuum* (e.g. bell peppers), *Capsicum frutescens* (Tabasco pepper), *Capsicum chinense* (Habanero pepper), and *Capsicum baccatum*. Pepper is an herbaceous species, generally grown as an annual crop, with fruits that vary in color, pungency, shape, and size. For instance, the fruit may be sweet or hot (pungent) and blocky or pointed, half-long, or of the Dulce Italiano or Corno di Toro types, among others. In view of the disclosed methods and compositions, pepper plants which produce fruit of different pungency levels and of various shapes, colors, and sizes are contemplated. Also contemplated are seeds, seed mixtures, cells, vegetative propagules, and fruit of the isogenic, nearly isogenic, or hybrid pepper lines which may thus be developed.

Utilizing genetic markers as disclosed herein, and/or markers genetically linked to these identified loci, and source lines, the methods described herein allow for production of nearly isogenic lines that differ in the mature fruit colors red, yellow, red-orange, and orange, and loci tightly linked to the color loci, but otherwise have essentially the same agronomic properties. These nearly isogenic lines can be used to produce nearly isogenic hybrids, which are of interest because each of the differently colored nearly isogenic hybrids have substantially the same horticultural properties, allowing growers to manage each variety in the same way. In contrast, current red, yellow and orange commercial varieties are typically distinct and may each have different pruning, nutritional, or pest control needs, adding complexity and expense to operations producing more than one color type. Additionally, the present invention allows for simplified breeding of pepper lines for producing multi-colored pepper packs, which have become increasingly popular. Additionally, breeding and hybrid lines may be produced and identified, for instance by transferring elite traits from typically more agronomically advanced red-fruited lines in order to improve orange and yellow-fruited germplasm. In addition the invention allows for the first time the production of substantially identical pepper fruits that differ in color. The invention thus also provides collections, including prepackaged collections, of near isogenic pepper fruit differing in color.

In one non-limiting example of a breeding method provided herein, the described color markers enable the consolidation of multiple breeding programs based on color into one multi-color breeding program. This can be achieved by crossing a red line that has both the intact Ccs and Ze alleles (CCSCCS ZEZE) with an orange line (ccsccs zeze) and maintaining both loci in a heterozygous state during breeding. In any given generation, a subset of plants heterozygous for both of these color loci can be subjected to MAS, and breeders may perform additional phenotypic selection on these plants as well. When the line is sufficiently genetically and phenotypically fixed after n generations, the line can be selfed and the progeny of the desired color genotype and phenotype can be selected using the markers for Ccs and Ze. This results in homozygous nearly isogenic lines that only differ in the mature fruit colors red, yellow, and orange, and loci tightly linked to the color loci. The invention thus provides, in one embodiment, a pepper plant comprising a desired mature fruit color trait, as well as a nearly isogenic pepper line comprising plants displaying a range of mature fruit colors. Diversity in the described color markers exists, for instance, in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE).

As used herein, "red," "red-orange," "orange," "yellow" and other contemplated fruit colors may be defined, for instance, by their visual color phenotype and absorption spectra of the underlying carotenoids. Yellow fruits appear yellow by visual assessment and the underlying carotenoids display a lambda max at approximately 442 nm; Orange fruits appear orange by visual assessment and the underlying carotenoids display a lambda max at approximately 454 nm; Red-Orange fruits appear red by visual assessment and the underlying carotenoids display a lambda max at approximately 454 nm; Red fruits appear red by visual assessment and the underlying carotenoids display a lambda max at approximately 474 nm. The visual contrast between Red-Orange and Red may usually be distinguishable upon side-by-side comparison but a grouping of only Red-Orange fruits would be visually assessed as being red in color.

As used herein, a "female parent" refers to a pepper plant that is the recipient of pollen from a male donor line, which pollen successfully pollinates an egg. A female parent can be any pepper plant that is the recipient of pollen.

As used herein, "male parent plant" refers to a parent plant that provides pollen to (i.e. is a pollinator for) a female line. They may be useful for breeding of progeny pepper plants, such as progeny plants which display a mature fruit color of interest.

As used herein, a "part of the pepper plant" is further defined as pollen, an ovule, a leaf, an embryo, a root, a root tip, an anther, a flower, a fruit, a stem, a cutting, a shoot, a seed, a protoplast, a cell, and a callus. A tissue culture of cells from a pepper plant may also be of use in propagating pepper plants of the present invention. As used herein, "tissue culture" refers to a composition comprising isolated cells of the same type(s) or of a different type, or of a collection of such cells, that may be organized into parts of a plant.

As used herein, a "hybrid pepper plant" includes a plant resulting directly or indirectly from crosses between populations, breeds or cultivars within the genus *Capsicum*. "Hybrid pepper plant" as used herein also refers to plants resulting directly or indirectly from crosses between different species, varieties or genotypes.

As used herein, a "marker" is a detectable polymorphism. Typically a marker is an indicator for the presence of at least one phenotype or genotype. Markers include, but are not limited to, single nucleotide polymorphisms (SNPs), small to large insertions and deletions, chromosomal rearrangements, cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker may be inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with a trait of interest. Stringent conditions for hybridization of a nucleic acid probe or primer to a marker sequence or a sequence flanking a marker sequence refers, for instance, to nucleic acid hybridization conditions of 1×SSC, and 65° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies including TaqMan™, and nucleic acid sequencing technologies, etc.

As used herein, "near-isogenic" refers to a set of lines that are genetically highly similar (e.g. at least about 95% identical over the entire genome), but that differ with respect to chromosomal region(s) introduced from a "donor" parent line, such as a locus conferring fruit color as described herein. Near-isogenic varieties will generally share agronomic properties such that a farmer may apply substantially identical cultivation methods to grow a set of near isogenic varieties, and yield fruits that are essentially the same in appearance other than with respect to, for instance, fruit color.

Many useful traits that can be introduced by breeding strategies may also be introduced by genetic transformation techniques. Genetic transformation may therefore be used to insert a selected transgene, cisgene or intragene into a plant of the invention or may, alternatively, be used for the preparation of transgenes, cisgenes or intragenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts. Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques.

One aspect of the current invention thus concerns methods for producing seed for pepper hybrids that grow to yield fruit displaying a desired mature fruit color, such as red, red-orange, orange, or yellow, and shades thereof. Plants of a female pepper parent displaying the desired color trait, may be used in certain embodiments for the development of new (e.g. hybrid) pepper varieties, for instance via marker assisted selection. Alternatively or in addition, a pepper line may be developed by introgressing one or more agronomic traits of interest into plant displaying a mature fruit color if interest.

The development of new varieties using one or more starting varieties is well known in the art. One or more presently disclosed genetic markers may be utilized in a marker assisted selection breeding method to create novel pepper lines or cultivars. Alternatively other mature fruit color-associated genetic markers may be identified by a skilled worker, and may be utilized in accordance with the invention. Thus novel varieties may be created by crossing lines displaying polymorphism at one or more fruit color-associated locus, followed by evaluation of fruit color characteristics of progeny plants, as well as genotyping, optionally evaluating other traits of agronomic interest. Thus, new varieties may be created by crossing with a second plant of a parental line chosen to exhibit one or more selected desirable characteristics or which exhibit the desired characteristic(s) when in hybrid combination. Once crosses have been made, selection may take place to identify new varieties.

The plants of the present invention are particularly well suited for the development of new lines based on the nature of the genetic background of the plants, particularly in view of available agronomically advanced traits of red-fruited parental lines, which allows for use in a method of producing seeds capable of growing into a pepper plant displaying a desired mature fruit color, as well as other agronomically useful traits such as, in specific embodiments, parthenocarpy, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of pepper plants developed in view of this invention.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Capsanthin-Capsorubin Synthase (CCS) Marker Development

Pepper plants comprising a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, plants lacking a functional CCS have yellow or orange fruits. The CCS gene was mapped to the y locus on chromosome 6 of pepper and the trait of red vs. yellow fruit color was found to map to the bottom of chromosome 6 using an F2:F3 mapping population from a cross between a yellow blocky-shaped line (designated SBY-29-469) and a red Italian fryer line (designated SZZ-8T10901), as shown in Table 1.

TABLE 1

Map position of the y locus for red vs. yellow mature fruit color ("RY color").

| Marker | Chromosome | SBY-29-469/SZZ-8T10901 F2:F3 | Map position (cM) |
| --- | --- | --- | --- |
| NE0239299 | 6 | 0 | 24.2 |
| NE0238978 | 6 | 8.5 | 30.2 |
| NE0238845 | 6 | 14.5 | 35.0 |
| NE0240908 | 6 | 33.7 | 62.6 |
| NE0235266 | 6 | 35.1 | 62.6 |
| NE0241110 | 6 | 44.5 | 70.6 |
| NE0237057 | 6 | 55.4 | 80.1 |
| NE0240567 | 6 | 64.4 | 89.3 |
| NE0238405 | 6 | 91.9 | 107.4 |
| RY_color* | 6 | 123.4 | 120.6 |
| NE0237488 | 6 | 126.4 | 121.8 |
| NE0237446 | 6 | 136.4 | 132.4 |

*Red (R) vs. yellow (Y) color scored as a binary trait in F3 families to permit inference of all three genotypic classes in the F2 generation.

Additionally, genome wide association mapping provided additional evidence that the position of a causal mutation for red vs. non-red mature fruit color on chromosome 6 is general across sweet pepper germplasm. Data obtained from 2,836 mapped SNPs from a total of 209 red, 122 yellow, and 17 orange lines of the sweet blocky, sweet mini, and sweet long fruit types was used in a case-control association mapping analysis implemented in a whole genome association analysis toolset (PLINK; Purcell et al., *Am. J. Hum. Genet.* 81:559-575, 2007). The SNP with the most significant association to the red- vs. non-red trait (NE0237110) occurred at position 120.7 cM on chromosome 6.

Figure 2A:
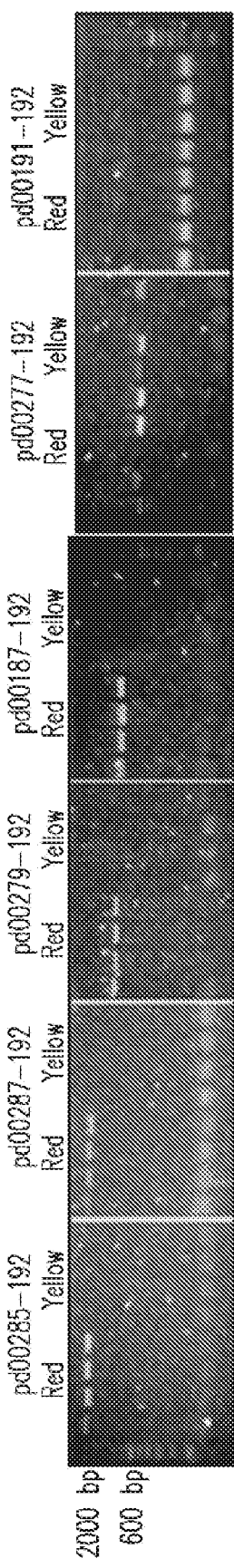
FIG. 2: PCR analyses reveal a deletion in the Ccs gene of non-red lines, as only primer combinations pd00277-pd00192 and pd00190-pd00192 yielded amplification products in both red and non-red (yellow) assayed lines. A) PCR amplicons obtained using different primer combinations in the Ccs gene. Primer combinations are listed on top of the panels. For each primer combination, four red and four yellow lines were used. B) Schematic representation of amplicons which were obtained; ATG and TGA respectively represent the start and stop codons of the Ccs gene. Next to each amplicon the expected amplicon size is indicated. Bars obtained with primers pd000285, pd000287, pd000279, and pd000187 represent amplicons obtained in red lines only; bars obtained with primers pd000277 and pd000190 represent amplicons obtained in all tested lines.
Figure 2B:
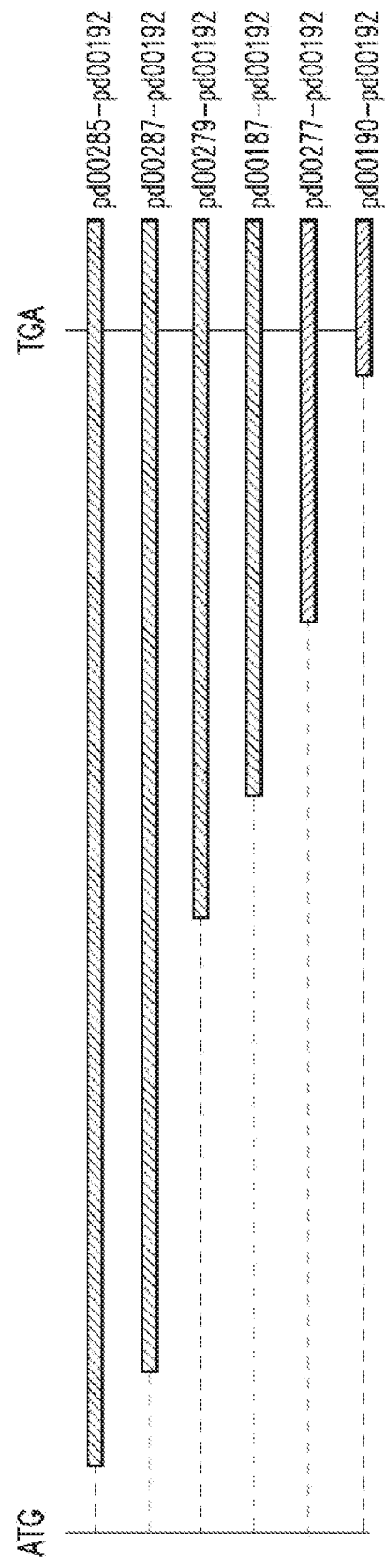

The Ccs gene sequence was previously deposited in Genbank (e.g. under accessions DQ907615.1 and X77289 (SEQ ID NO:1)). PCR analysis revealed that part of the CCS gene was deleted in certain studied pepper lines which produce non-red mature fruit. Primers were designed on parts of the CCS sequence and were used for PCR on red and non-red (yellow) lines (Table 2; SEQ ID NOs:2-9). Different forward primers were used, but in all PCR reactions primer pd00192 was used as reverse primer (Table 2; FIG. 2). Amplicons were always obtained from red lines, but in non-red lines amplicons were only obtained with primers that target the 3' region of the Ccs gene (FIG. 2). This inability to obtain amplicons is consistent with a deletion in the Ccs gene in non-red lines.

TABLE 2

Primers used to confirm deletion in Ccs gene of non-red lines (SEQ ID NOs: 2-9; see also FIG. 2).

| Primer | Sequence (5'-3') | Orientation | Expected fragment size (bp) | Amplicon obtained in Red | Amplicon obtained in Yellow |
|---|---|---|---|---|---|
| pd00285 | CAACTCCACTTTTCCAAATC | F | 1884 | Yes | No |
| pd00287 | GGTTGATACTGATCTGGACG | F | 1743 | Yes | No |
| pd00279 | GTGAGTCGGCCTATGTTATCG | F | 1066 | Yes | No |
| pd00187 | TGGTGGGACTTCAGGGATAG | F | 903 | Yes | No |
| pd00277 | TGTTGATCCCAAGTACTGGC | F | 639 | Yes | Yes |
| pd00190 | AGACTTGGTATCAGATTGTGGC | R | 418 | Yes | Yes |
| pd00191 | AGCCACAATCCGATACCAAG | F | 246 | Yes | Yes |
| pd00192 | GAGGGACAAGAGTGGAGCAG | R | N/A | N/A | N/A |

Figure 3:
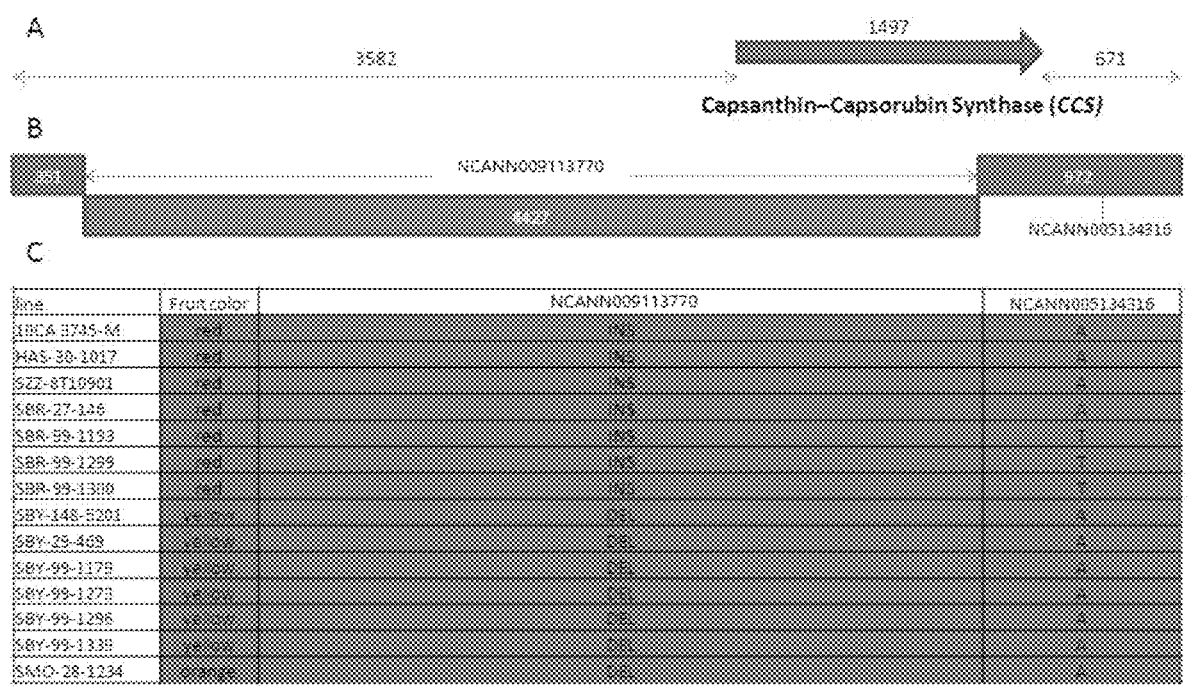
FIG. 3: A) Schematic representation of the Ccs gene and flanking sequences in a red pepper background. B) Size and position of the deletion found in both yellow and orange lines. C) Observed color of 14 tested pepper lines and the genotypes obtained with TaqMan™ markers NCANN009113770 (based on the deletion) and NCANN005134316 (based on an A/T SNP in the 3'UTR).

Genome walking experiments were performed to confirm the presence of a deletion in the Ccs gene of non-red lines. This analysis and additional sequencing showed that the Ccs gene contains an intact ORF in all red lines tested, while a 4472 bp deletion is present in all tested non-red lines (FIG. 3). The deletion covers most of the CCS ORF (1196 bp) and as a result only 351 bp of the sequence is conserved between red and non-red lines. Moreover, 3231 bp in the 5' UTR are absent in non-red lines compared to red lines. In the 3' UTR, a segment of 671 bp was conserved between red and non-red lines, albeit with several polymorphisms between these alleles. In total, 5750 bp of sequence was obtained from red pepper lines: 3582 bp of sequence was obtained from the 5' UTR, 671 bp from the 3' UTR, and the CCS ORF itself is 1497 bp in length. The observation that only red fruited lines have an intact Ccs gene leads to the conclusion that Capsanthin-Capsorubin Synthase is needed to convert the non-red carotenoids into the red carotenoids A TaqMan™ assay designated Q-NCANN009113770 was designed to assay the presence or absence of sequence at the 4472 bp deletion site in the Ccs gene. Primer and probe design for the NCANN009113770 assay are shown in Table 3 (SEQ ID NOs:10-14). Similarly performing assays can be designed by varying the position of the forward and reverse primers or by designing the primers against the complementary strand of DNA. The inferred fruit color phenotypes obtained with this marker on a line panel are shown in FIG. 3C. Another TaqMan™ assay designed for red vs. non-red marker assisted selection utilized marker NCANN005134316 (based on the A/T polymorphism in SEQ ID NO:19), and was designed to target an A/T SNP in the 3' UTR of Ccs. Primer and probe design for the NCANN009113770 assay are shown in Table 3 (SEQ ID NOs:15-18. This assay was predictive in approximately 95% of tested pepper germplasm. However, as shown in FIG. 3C, several lines with red fruits carry the A allele of NCANN005134316, associated with non-red fruits.

TABLE 3

Primers and probes used for TaqMan ™ assays NCANN009113770 and NCANN005134316 (SEQ ID NOs: 10-18).

| Name | Description | Sequence | Allele |
|---|---|---|---|
| NCANN009113770_F1 | forward primer 1 | TCGAAAGCCTTGGCTCAACA | |
| NCANN009113770_F2 | forward primer 2 | TTTTGTATCTCCCTTTCCCAGAA | |
| NCANN009113770_R | reverse primer | TCTCTAACACGTCTTCTATCCGAAGG | |
| NCANN009113770_V | VIC probe | AGAATGATAAGAGGGTCT | INS |
| NCANN009113770_M | FAM probe | CTTTTAGAGTTTGGAATG | DEL |
| NCANN005134316_F | forward primer | CCAAACACTTTGAATTGGCTGGATA | |
| NCANN005134316_R | reverse primer | ACTATATTAACTTTCCTAATAATTCTTGCTTTCCCA | |
| NCANN005134316_V | VIC probe | TGCTGTTAATGATTAATAACAT | A* |
| NCANN005134316_M | FAM probe | CTGTTAATGATTAAAAACAT | T* |

*probes are designed on the reverse complement sequence

Table 4 shows an overview of the studied mutations found in the Ccs gene and flanking sequences (SEQ ID NOs:20-38). In total 13 additional SNPs and small indel mutations were identified in the 3' UTR of the Ccs gene (Table 4). Three of these are indel mutations (of 3, 4 and 14 bp respectively). The other 10 mutations are SNPs. Two of these SNPs were only found in line HAS-30-1017, which is consistent with the fact that the Asian germplasm is genetically divergent from the sweet pepper germplasm. One line-specific SNP was found in line SBY-99-1273.

TABLE 4

Overview of mutations found in the CCS gene and flanking sequences.
The INS/DEL identified by marker NCANN009113970 is given in SEQ ID NO: 39.

| | Fruit color | Marker Root Name | | | | |
|---|---|---|---|---|---|---|
| | | NCANN005134316 [A/T] | NCANN009113770 [INS/DEL] | NCANN009113570 [T/C] | NCANN009113170 [C/A] | NCANN009113970 [TATGGTTGTCGATG/*] |
| SBR-99-1193 | Red | A | INS | T | C | * |
| SBR-99-1299 | Red | A | INS | T | C | * |
| SBR-99-1300 | Red | A | INS | T | C | * |
| HAS-30-1017 | Red | A | INS | T | C | TATGGTTGTCGATG |
| 10CA 3745-M | Red | T | INS | C | A | TATGGTTGTCGATG |
| SZZ-B510901 | Red | T | INS | C | A | TATGGTTGTCGATG |
| SBR-27-146 | Red | T | INS | C | A | TATGGTTGTCGATG |
| SB-148-5201 | Yellow | T | DEL | C | A | TATGGTTGTCGATG |
| SBY-28-468 | Yellow | T | DEL | C | A | TATGGTTGTCGATG |
| SBY-99-1179 | Yellow | T | DEL | C | A | TATGGTTGTCGATG |
| SBY-99-1273 | Yellow | T | DEL | C | A | TATGGTTGTCGATG |
| SBY-99-1296 | Yellow | T | DEL | C | A | TATGGTTGTCGATG |
| SBY-99-1339 | Yellow | T | DEL | C | A | TATGGTTGTCGATG |
| SMO-2B-1234 | Orange | T | DEL | C | A | TATGGTTGTCGATG |

TABLE 4-continued

Overview of mutations found in the CCS gene and flanking sequences.
The INS/DEL identified by marker NCANN009113970 is given in SEQ ID NO: 39.

| | Marker Root Name | | | | |
|---|---|---|---|---|---|
| | NCANN009113370 [T/C] | NCANN009113971 [T/A] | NCANN009113371 [G/t] | NCANN009114170 [AACA/*] | NCANN009114370 [A/C] |
| SBR-99-1193 | C | T | T | AACA | A |
| SBR-99-1299 | C | T | T | AACA | A |
| SBR-99-1300 | C | T | T | AACA | A |
| HAS-30-1017 | T | A | G | AACA | A |
| 10CA 3745-M | T | T | G | * | A |
| SZZ-B510901 | T | T | G | * | A |
| SBR-27-146 | T | T | G | * | A |
| SB-148-5201 | T | T | G | * | A |
| SBY-28-468 | T | T | G | * | A |
| SBY-99-1179 | T | T | G | * | A |
| SBY-99-1273 | T | T | G | * | C |
| SBY-99-1296 | T | T | G | * | A |
| SBY-99-1339 | T | T | G | * | A |
| SMO-2B-1234 | T | T | G | * | A |

| | Marker Root Name | | | | |
|---|---|---|---|---|---|
| | NCANN009113571 [A/g] | NCANN009113171 [G/t] | NCANN009113372 [C/t] | NCANN009113771 [G/t] | NCANN009114171 [aac/*] |
| SBR-99-1193 | A | T | T | T | AAC |
| SBR-99-1299 | A | T | T | T | AAC |
| SBR-99-1300 | A | T | T | T | AAC |
| HAS-30-1017 | G | T | T | T | AAC |
| 10CA 3745-M | A | G | C | G | * |
| SZZ-B510901 | A | G | C | G | * |
| SBR-27-146 | A | G | C | G | * |
| SB-148-5201 | A | G | C | G | * |
| SBY-28-468 | A | G | C | G | * |
| SBY-99-1179 | A | G | C | G | * |
| SBY-99-1273 | A | G | C | G | * |
| SBY-99-1296 | A | G | C | G | * |
| SBY-99-1339 | A | G | C | G | * |
| SMO-2B-1234 | A | G | C | G | * |

For accuracy tests, marker NCANN009113770 was validated on a panel of 615 leaf samples. The panel was derived from variety trials and predominantly contained lines that were developed for the Dutch greenhouse market. In all tested plants of visually-assessed fruit color, only two gave an unexpected genotype (Table 5), which are likely caused by a technical error, probably caused by a mistaken color description. Nonetheless, in this trial the marker is at least >99.6% accurate.

TABLE 5

Accuracy test results for marker NCANN009113770.

| Observed Phenotype | Genotype | | | |
|---|---|---|---|---|
| | INSINS | INSDEL | DELDEL | — |
| | Inferred phenotype | | | |
| | Red | Red | Not-red | — |
| Red | 294 | 22 | 1* | 12 |
| Yellow | 0 | 0 | 181 | 4 |
| Orange | 1* | 0 | 98 | 2 |

*conflict between inferred and observed phenotypes

In conclusion, marker NCANN009113770 is based on a large deletion mutation in the CCS gene; all available data suggests that this mutation prevents the formation of red pigment in non-red pepper fruits. The marker is thus highly predictive for mature fruit color.

FIG. 8 gives an alignment of Ccs sequences from 14 pepper lines (SEQ ID NOs:40-53) showing the location of polymorphisms. A consensus CCS ORF sequence is given at SEQ ID NO:54. SNPs are indicated by asterisks. The predicted protein sequence of CCS is given at SEQ ID NO:55.

Of additional note is the discovery that plants can survive without a functional CCS gene. It follows that other mutations in the gene also may result in non-red fruit. An altered CCS genotype may therefore be provided by any suitable means; for example, EMS, MMS, other mutagen-derived, in situ-derived, or naturally-occurring mutations can provide an altered CCS genotype suitable for the development of the fruit color phenotypes described here. Color modulation of the fruit color phenotypes described here may also be achieved by transient disruption of CCS function at the time of fruit set and/or fruit color maturation.

Example 2

Zeaxanthin Epoxidase (Ze) Marker Development

The Zeaxanthin Epoxidase (Ze or ZEP hereafter) gene (Genbank X91491; SEQ ID NO:56) regulates the conversion of zeaxanthin to the yellow pigments antheraxanthin and violaxanthin. The gene is mapped to the lower part of chromosome 2 in pepper (Thorup et al. 2000) and the yellow-orange color polymorphism (YO_color) locus maps to the same region of chromosome 2. Map positions were derived from a linkage analysis study of an F2:F3 population (from a cross between a yellow line and an orange line) to arrive at a rough map position of 100.8 cM for the yellow-orange color locus (Tables 6-7).

TABLE 6

Map position of YO_color locus using an F2:F3 bi-parental mapping population. Nucleotide sequences around listed markers are given in SEQ ID NOs: 57-62.

| Marker | Chromosome | SBY-29-469/SMO-28-1234 F2:F3 | Map position (cM) |
|---|---|---|---|
| NE0235373 | 2 | 0 | 88.9 |
| NE0240266 | 2 | 2.9 | 94.2 |
| NE0237869 | 2 | n/a | 95.0 |
| YO_color* | 2 | 16.6 | 100.8 |
| NE0239621 | 2 | 22.4 | 103.6 |
| NE0240354 | 2 | 34.8 | 111.7 |
| NE0241248 | 2 | 37.1 | 113.6 |

*Yellow (Y) vs. orange (O) color scored as a binary trait in F3 families to permit inference of all three genotypic classes in the F2 generation.

TABLE 7

Primers and probes used for TaqMan ™ assays with markers of Table 6 (SEQ ID NOs: 63-86).

| Marker | Position | Primer or probe name | Sequence | Allele |
|---|---|---|---|---|
| NE0235373 | 88.9 | NE0235373_F | CGTAAATTGTAGTCCTTGCCTCAGT | |
| | | NE0235373_R | GGACAAGGGAGGAAGTTGAATCTAA | |
| | | NE0235373_V | CTCTATTGACAAGAAACAA | T |
| | | NE0235373_M | CTATTGACAGGAAACAA | C |
| NE0240266 | 94.2 | NE0240266_F | CTGGTCCAACTCTACATGTACGT | |
| | | NE0240266_R | CCAATGGATAGTGAGATCGTATGGTAATT | |
| | | NE0240266_V | AGGGCGACACCATTGT | A |
| | | NE0240266_M | AGGGCGACACCCTTGT | C |
| NE0238769 | 95.0 | NE0238769_F | CAATCAATCAACAAGGACAAACCAATGA | |
| | | NE0238769_R | CTAGAGTATTACATTCTTTTGCCAAGGGA | |
| | | NE0238769_V | ATCTTGGATAGTACAGCTGTAT | C |
| | | NE0238769_M | ATCTTGGATAGTACAACTGTAT | T |
| NE0239621 | 103.6 | NE0239621_F | GTACTTTTTGTCTTGTTGGACCAATCC | |
| | | NE0239621_R | ACCATGTTGCAGTCAATACGTACA | |
| | | NE0239621_V | CCCCCTCCAATGTAAA | T |
| | | NE0239621_M | CCCCCTCCAGTGTAAA | C |

TABLE 7-continued

Primers and probes used for TaqMan ™ assays with markers of Table 6 (SEQ ID NOs: 63-86).

| Marker | Position | Primer or probe name | Sequence | Allele |
|---|---|---|---|---|
| NE0240354 | 111.7 | NE0240354_F | TCAGTTATATTAAAGAAAATGTATGATAAATAGCA | |
| | | NE0240354_R | GCAGTAAATGGATATATTATACGCAAAAGCA | |
| | | NE0240354_V | ATGTGTTGGTGTTGTATAA | A |
| | | NE0240354_M | ATGTGTTGGTGATGTATAA | T |
| NE0241248 | 113.6 | NE0241248_F | GTTGTTCCCTGCTCTTGCTGTA | |
| | | NE0241248_R | CACCGGCCAAGATTCCTCAA | |
| | | NE0241248_V | CCTGTGTTGTGTTGTTGT | T |
| | | NE0241248_M | CTGTGTTGTGCTGTTGT | C |

Association mapping provided additional evidence that the position on chromosome 2 is common across the relevant pepper germplasm. Data obtained from assaying 2,836 mapped SNPs from a total of 122 yellow and 17 orange lines of the sweet blocky, sweet mini, and sweet long fruit types was used in a case-control association analysis implemented in PLINK. The strongest association between yellow- vs. orange color and a mapped SNP was detected for NE0238769 at position 95.04 cM on chromosome 2.

Figure 4:
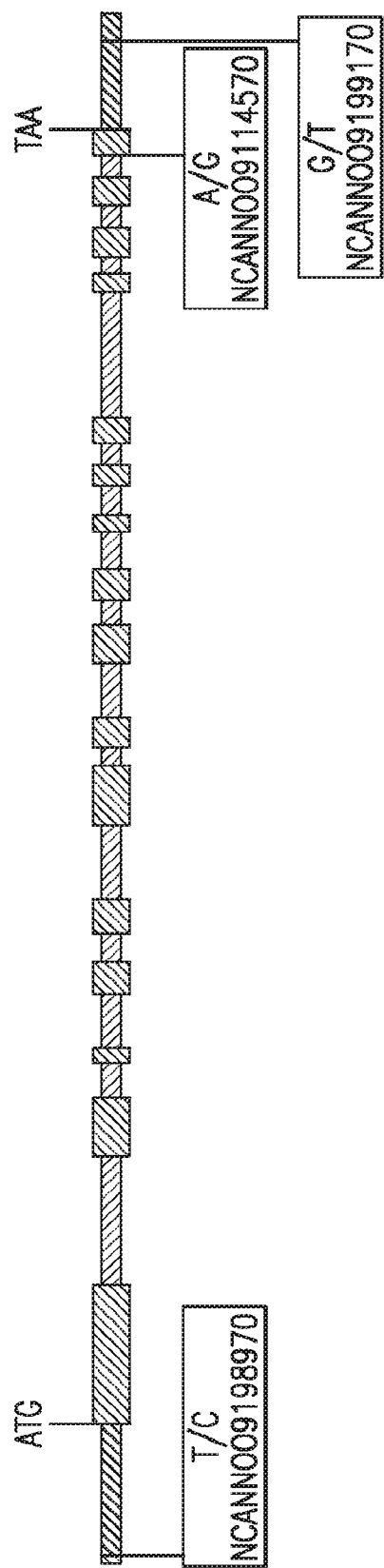
FIG. 4: The genomic structure of the Ze gene. Boxes set into top line represent coding regions (exons); other portions of the top line represent introns, and regions upstream of the ATG and downstream of the TAA represent the UTR. The start codon (ATG indicated on top line) and stop codon (TAA on top line) are also indicated, while the three identified SNPs are indicated on the bottom of the figure.

Only cDNA sequence was available for the *C. annuum* Ze gene in the public domain (Genbank X91491), and no SNPs were known to have been described in the coding sequence of the gene. Analysis of initial efforts to sequence the genomic gene sequence led to the conclusion that it was rich in introns (now known to be 15 introns in total) and extensive re-sequencing of genomic DNA was required to obtain the full sequence (introns and exons). In total 4803 bp were sequenced. The coding sequence (SEQ ID NO:56) comprises 1971 bp, corresponding to a 656 AA protein. This differs from Genbank X91491, which is 1983 bp in length, corresponding to a 660 AA protein. The coding sequence of SEQ ID NO:56 is divided over 16 exons. The 15 introns comprise 2831 bp while in total 950 bp are obtained from the UTR (Table 8). In total 3 SNPs were identified between yellow and orange lines (Table 8). The complete genomic organization of the Ze gene is represented in FIG. 4.

TABLE 8

Sizes in bp of coding and non-coding sequences in the pepper Ze gene.

| Coding sequence | | Non-Coding sequence | |
|---|---|---|---|
| | | 5' UTR | 526 |
| exon 1 | 497 | intron 1 | 505 |
| exon 2 | 196 | intron 2 | 150 |
| exon 3 | 42 | intron 3 | 213 |
| exon 4 | 101 | intron 4 | 117 |
| exon 5 | 116 | intron 5 | 285 |
| exon 6 | 212 | intron 6 | 86 |
| exon 7 | 90 | intron 7 | 226 |
| exon 8 | 123 | intron 8 | 104 |
| exon 9 | 99 | intron 9 | 163 |
| exon 10 | 31 | intron 10 | 130 |
| exon 11 | 65 | intron 11 | 96 |
| exon 12 | 86 | intron 12 | 480 |
| exon 13 | 55 | intron 13 | 81 |
| exon 14 | 89 | intron 14 | 96 |
| exon 15 | 85 | intron 15 | 99 |
| exon 16 | 84 | | |
| | | 3' UTR | 424 |
| Total | 1971 | | 3781 |

TABLE 9

SNPs identified in the Ze gene between orange and yellow lines (SEQ ID NOs: 87-89).

| Marker | Yellow allele | Orange allele | Location |
|---|---|---|---|
| NCANN009198970 | T | C | 5' UTR |
| NCANN009114570 | A | G | Intron 15 |
| NCANN009199170 | G | T | 3' UTR |

The [A/G] SNP in intron 15 (Table 9) is close to the intron-exon acceptor splice site and the allele found in orange lines (carrying the G allele) has a disrupted intron-exon acceptor site. In the Ze sequence of yellow fruited pepper lines, a typical acceptor splice site for an intron-exon barrier can be found on the borders of intron 15 and exon 16: CAG^GC (SEQ ID NO:90) (the ^ represents the actual splice site). The SNP in the allele found in orange lines has a sequence of CGGGC (SEQ ID NO:91), which is not a functional splice site. This SNP thus likely affects the plant's ability to produce a fully functional Zeaxanthin Epoxidase transcript and, as a result, significantly less yellow pigments are formed in plants carrying this allele in a homozygous state. As a result, these plants have orange fruits. The alignment in FIG. 5 shows the 3' region of the Ze gene and compares sequences of a yellow line to an orange line (SEQ ID NOs:96-97), the predicted coding sequence (SEQ ID NO:98), and a sequence from CM334 ("contig36343"; SEQ ID NO:99). All SNPs are indicated with an asterisk (*) and the marker names (MRNs) are indicated.

To carry out accuracy tests of marker NCANN009114570, a TaqMan™ assay was designed on the SNP NCANN009114570 (Table 10; SEQ ID NOs:92-95). For accuracy tests, marker NCANN009114570 was validated on a panel of 321 leaf samples. The panel was derived from variety trials and was dominated by lines bred for the Dutch greenhouse market. In all tested plants only one plant, out of 321 tested, gave an unexpected genotype, i.e. wherein the identified fruit color did not agree with the genotype at marker NCANN009114570 (yellow fruit expected for TT genotype; orange fruit expected for CC genotype), which was thought to be caused by an error in assignment of fruit color, as this is the same line used in CCS marker testing in which the phenotype and marker genotype did not agree. Thus, in this trial the marker was >99.6% accurate.

TABLE 10

Design details of TaqMan ™ assay NCANN009114570 (SEQ ID NOs: 92-95).

| Name | description | Sequence | Allele* |
|---|---|---|---|
| NCANN009114570_F | forward primer | CAGCAGTTTTTGAAGGAAATTTCATTGTC | |
| NCANN009114570_R | reverse primer | GGCATTGGCAGTAGCTTATTACTCA | |
| NCANN009114570_V | VIC probe | ATGTTATGCGGGCAGCA | C |
| NCANN009114570_M | FAM probe | ATGTTATGCAGGCAGCA | T |

*probes are designed on the reverse complement sequence

Marker NCANN009114570 was designed on the reverse complement sequence of the Ze gene. The [A/G] SNP in the gene is therefore registered as a [C/T] SNP.

In conclusion, marker NCANN009114570 is based on a SNP that disrupts the production of a fully functional Zeaxanthin Epoxidase ("ZEP") transcript. The presence of this mutation appears almost perfectly correlated with the absence of yellow pigments in orange pepper fruits. The marker is highly predictive for mature fruit color in pepper and is a suitable marker for MAS and MABC applications.

This mutation yields a plant that can survive without a functional ZEP protein. It follows that other mutations in the gene also may result in the absence of yellow pigments in orange pepper fruits. An altered ZEP genotype may therefore be provided by any suitable means; for example, EMS, MMS, other mutagen-derived, in situ-derived, or naturally-occurring mutations can provide an altered ZEP genotype suitable for the development of the fruit color phenotypes described here. Color modulation of the fruit color phenotypes described here may also be achieved by transient disruption of ZEP function at the time of fruit set and/or fruit color maturation.

Example 3

Carotenoid Profiles of Red, Orange, and Yellow Pepper Fruits

The carotenoid profiles of various colored pepper fruits were measured, and those data used and to test the predictiveness of markers NCANN009113770 (CCS) and NCANN009114570 (ZEP) for determining the genotypes and phenotypes of the genes responsible for mature pepper fruit color. Carotenoid contents and profiles were analyzed in a panel of 133 pepper varieties representing red (n=55), orange (n=23), and yellow (n=55) mature fruit colors. The panel was selected from variety trials and contained lines predominantly for the Dutch greenhouse market. Carotenoid values were obtained using an Ultra high performance liquid chromatography (UHPLC) UV detection assay. Marker assay test results were obtained from DNA samples isolated from collected leaf samples.

Reversed Phase Ultra High Pressure Liquid Chromatography and UV DAD detection of Carotenoid Pigments: The pigment carotenoid content of the pepper samples was analyzed by reverse phase ultra high pressure liquid chromatography (UHPLC) UV DAD. All procedures were performed on ice, using amber glassware and/or reduced light where possible. Pepper samples were cut into pieces, removing and discarding the peduncle, seeds, and placental tissue, leaving only the pericarp. The pepper sample was weighed and an equal amount of nanopure water (1:1, weight/weight) was added. Samples were blended in a Vitamix blender (Vitamix Corporation, Cleveland, Ohio, USA) for approximately 30 seconds on high. The puree was transferred to a 50 mL centrifuge tube, and sample extraction and analysis was either performed immediately or stored at −80° C. Pureed pepper pericarp (0.5 g) was extracted with acetone: methanol:hexane (2:1:1, v/v/v, 0.5% BHT) containing 0.5 ppm β-apo-8'-carotenal (Sigma-Aldrich, St. Louis, USA). The extraction mixture was sonicated for 20 minutes on ice. After sonication, 1 M sodium chloride in water was added to the extraction mixture. Extraction vials were centrifuged and 1 ml aliquots of upper hexane phase were syringe filtered and placed in amber vials and either analyzed immediately or stored at −20° C. until analysis. Extracts were separated and analyzed using an Agilent 1260 UHPLC with quaternary pump and Waters BEH C18 column. The injection volume was 2 µl and the eluent flow was 0.375 µl/min. Detection and quantitation was by UV DAD by monitoring at 450±20 nm with no reference wavelength.

Data processing: Chromatograms were processed using Agilent Chemstation® software to integrate and identify peaks. Carotenoids were identified based upon relative retention time and UV absorption spectra in comparison to authentic standards. Carotenoids were quantified based upon generated relative response factors (RRF) using β-apo-8'-carotenal as an internal standard. Carotenoid esters were tentatively identified based upon absorption spectra, retention time and literature reference values. Retention characteristics of carotenoid esters were used to tentatively identify as either monoester or diester carotenoid pigments. Relative quantification was performed for monoester and diester carotenoid pigments using the calculated RRF values of the free carotenoid authentic standards.

Spectrophotometric Determination of Carotenoid Pigments. UV absorption spectra (375-550 nm) were collected with a UV-Vis spectrophotometer. Briefly, 1.0 grams of pepper puree used was placed in a 50 ml conical tube. To the sample, 40 ml of 100% acetone was added. The tubes were shaken and placed in the dark at room temperature overnight. Prior to analysis, sample tubes were centrifuged for 15 minutes at 3000 rpm at room temperature (RT). A 1.0 ml aliquot was placed in a cuvette and spectra were recorded. Spectra were normalized to the spectra of pure acetone.

TABLE 11

Total carotenoid concentrations (μg/gFW) according to mature pepper fruit phenotype and genotype.

| Fruit Color | NCANN-00911-3770 (INS/DEL) | NCANN-00911-4570 (T/C) | Sample Number (n) | Capsanthin | Capsorubin | Zeaxanthin | β-carotene | β-crypto-xanthin | Violaxanthin | Anther-axanthin | Lutein | α-Caro-tene |
|---|---|---|---|---|---|---|---|---|---|---|---|---|
| Red | INS | T | 36 | 60.80 ± 17.31 | 6.75 ± 2.05 | 1.57 ± 0.38 | 9.67 ± 3.46 | 0.94 ± 0.35 | 2.58 ± 0.72 | 3.43 ± 0.99 | ND | ND |
| Red | INS | H | 5 | 60.89 ± 21.54 | 5.67 ± 2.10 | 2.83 ± 1.15 | 9.48 ± 4.16 | 1.27 ± 0.56 | 2.53 ± 0.74 | 4.43 ± 1.65 | ND | ND |
| Red | INS | C | 2 | 25.38 ± 9.97 | 0.78 ± 0.14 | 23.92 ± 5.35 | 17.27 ± 7.11 | 1.91 ± 0.85 | 9.88 ± 3.95 | 0.14 ± 0.02 | ND | ND |
| Red | H | H | 6 | 64.28 ± 18.19 | 5.58 ± 2.05 | 3.21 ± 1.38 | 15.07 ± 6.16 | 1.79 ± 0.69 | 3.47 ± 1.02 | 4.28 ± 1.42 | ND | ND |
| Red | H | T | 6 | 49.85 ± 7.25 | 5.058 ± 0.92 | 2.08 ± 0.55 | 15.11 ± 5.15 | 1.23 ± 0.36 | 2.82 ± 0.41 | 3.32 ± 0.62 | ND | ND |
| Orange | DEL | C | 23 | ND | ND | 38.03 ± 9.98 | 14.07 ± 5.41 | 1.27 ± 0.44 | 1.73 ± 0.50 | 6.66 ± 2.42 | 7.32 ± 1.21 | 0 ± 0 |
| Yellow | DEL | T | 55 | ND | ND | 0.29 ± 0.12 | 0.94 ±1 0.40 | 0.17 ± 0.13 | 10.32 ± 3.45 | 1.08 ± 0.41 | 3.47 ± 0.67 | 0.81 ± 0.38 |

*Mean ± SD;
ND - Not Detected;
H - Heterozygous

In red vs. non-red varieties, 55 phenotypic red varieties were analyzed for carotenoid content. As shown in Table 11, all lines phenotypically scored as red contained the red carotenoids capsanthin and capsorubin. Of the 78 non-red varieties (orange and yellow), no capsanthin or capsorubin pigments were detected in any samples tested. Marker NCANN009113770 was applied to the sample set to understand the predictability of red vs. non-red classification. As shown in Table 12, samples containing the CCS insertion (n=43) or heterozygotic (H) for the insertion (n=12), contained the red carotenoids capsanthin and capsorubin. Of the samples positive for the deletion (n=78), no capsanthin or capsorubin pigments were detected. These data indicate that the carotenoids capsanthin and capsorubin are indicative of red pepper fruits and that marker NCANN009113770 predicts the presence or absence of the red carotenoids capsanthin and capsorubin in this subset of red peppers.

Within the non-red varieties, varieties were scored as orange (n=23) or yellow (n=55) based upon visual appearance. As indicated in Table 11, all non-red varieties were positive for the CCS deletion according to the NCANN009113770 marker and were devoid of the red carotenoids capsanthin and capsorubin in their fruits. Among orange varieties, the highest concentration of carotenoids was evidenced from the orange carotenoid fraction, namely zeaxanthin and β-carotene. Zeaxanthin concentrations were highest in the orange varieties compared to both red and yellow varieties. Among yellow varieties, the highest concentration of carotenoids was evidenced in the yellow carotenoids, namely violaxanthin and lutein. The yellow carotenoid concentrations were significantly higher than orange carotenoids in the yellow pepper varieties.

The NCANN009114570 marker is predicted to specify the presence of a fully functional or impaired-function ZEP enzyme. Accordingly, perturbation in this enzyme (e.g. in translation or catalytic function) is expected to produce changes in the carotenoid profile namely through accumulation of zeaxanthin or production of the carotenoids antheraxanthin and violaxanthin. All yellow varieties (n=55) were positive for the T-allele, indicating presence of a fully functional ZEP enzyme. Yellow varieties accumulated the yellow carotenoid violaxanthin at the highest concentration. In comparison, all orange varieties were positive for the C-allele (Table 11), indicating the presence of a ZEP enzyme with reduced function. Accordingly, the orange varieties accumulated significant concentrations of zeaxanthin, implicating a non-functional ZEP protein. Further evidence of a impaired function ZEP is provided within the red varieties. Two red varieties that contained the CCS insertion also contained the C-allele of ZEP. These varieties, while still producing significantly lower concentrations of capsanthin and capsorubin, produced significantly higher concentration of zeaxanthin compared to other red varieties (Table 10). The zeaxanthin concentrations were similar to levels seen in orange varieties. These data indicate that the C-allele of the ZEP protein encodes a ZEP enzyme with significantly decreased function resulting in the accumulation of the orange carotenoid zeaxanthin.

To further understand the contribution of colored carotenoid fractions, color ratios were constructed based upon the

TABLE 12

Carotenoid color ratios according to mature pepper fruit phenotype and genotype.

| Fruit Color | NCANN009113770 (INS/DEL) | NCANN009114570 (T/C) | Sample Number (n) | Red Ratio $R_{Total}/(Y_{Total} + O_{Total})$ | Orange Ratio $O_{Total}/(R_{Total} + Y_{Total})$ | Yellow Ratio $Y_{Total}/(R_{Total} + O_{Total})$ |
|---|---|---|---|---|---|---|
| Red | INS | T | 36 | 3.76 ± 0.52 | 0.17 ± 0.03 | 0.08 ± 0.01 |
| Red | INS | H | 5 | 3.27 ± 0.54 | 0.19 ± 0.04 | 0.09 ± 0.01 |
| Red | INS | C | 2 | 0.49 ± 0.03 | 1.21 ± 0.10 | 0.14 ± 0.01 |
| Red | H | H | 6 | 2.60 ± 0.57 | 0.26 ± 0.06 | 0.09 ± 0.01 |
| Red | H | T | 6 | 2.33 ± 0.49 | 0.30 ± 0.06 | 0.08 ± 0.01 |
| Orange | DEL | C | 23 | NA | 3.37 ± 0.39 | 0.30 ± 0.03 |
| Yellow | DEL | T | 55 | NA | 0.09 ± 0.02 | 11.75 ± 2.92 |

*Mean ± SD total carotenoid concentration of the red, orange, or yellow carotenoid fractions. As shown in Table 12, for red varieties the red carotenoid fraction constitutes the largest pool of carotenoids when compared with the contribution of the orange or yellow carotenoids to the total carotenoid pool. In orange varieties, the orange carotenoid fraction constitutes the major carotenoid fraction compared to the yellow carotenoids. In yellow varieties, the yellow carotenoid fraction constitutes the largest carotenoid pool compared to the orange fraction. These data further indicate that mature pepper fruit color is driven by the underlying carotenoid profiles, which constitutes the red, orange, and yellow phenotypic appearance of pepper fruit colors.

Based upon the analytical data, red pepper fruits contain the red carotenoids capsanthin and capsorubin while they are not detected in non-red (orange or yellow) fruits. The presence of red carotenoids was associated with the presence of the CCS insertion (NCANN009113770) while the absence of red carotenoids is associated with the CCS deletion. In orange and yellow fruits, increased concentration of zeaxanthin is associated with orange mature pepper fruit color. Moreover, the increase in zeaxanthin is correlated with the C-allele of marker NCANN009114570. The presence of the ZEP T-allele results in shift in carotenoid fractions towards the yellow carotenoids, resulting in yellow fruit color. Further evidence of the ZEP function and prediction accuracy of marker NCANN009114570 is found in two varieties phenotypically described as red but predicted by this marker to be orange. The major carotenoid accumulated by these two varieties is the orange carotenoid zeaxanthin and the carotenoid distribution, as evidenced by the carotenoid ratios, is aligned with the observed orange carotenoid profiles. The analytical data combined with the marker information, indicate that the CCS and ZEP enzymes predict mature pepper fruit color.

Example 4

Linkage Disequilibrium Decay Surrounding Ccs and Ze

Markers based on causal genes are especially valuable for breeding and trait integration purposes when linkage disequilibrium (LD) around a trait locus is low. On the other hand, when LD around the causal mutation is relatively higher, then a linked marker in strong LD with the causal gene may suffice for most breeding applications. To better understand the value of the discovered mutations, for breeding, an LD analysis using marker data was performed for chromosomes 2 and 6 harboring the color loci Ze and Ccs, respectively. In total, 5191 SNP markers were used in this analysis. The analysis was performed on several pepper subpopulations (based on fruit type) and monomorphic markers within these populations were excluded in the analysis. In total, 882 pepper lines were used for the analysis.

LD was estimated using the $r^2$ metric (Hill and Robertson, TAG 38:226-231, 1968) and was calculated for all pairs of markers on LG6 and LG2 for each subpopulation. LD decay was examined using the equation: $LD_{ij}=1/(1+4b_j d_i)+e_{ij}$, where LD is the observed $r^2$ between the i-th marker pair in subpopulation j, $d_i$ is the genetic distance between the i-th marker pair in Morgans, $b_j$ is the coefficient of LD decay in subpopulation j, and $e_{ij}$ is the random residual. The extent of LD decay was taken to be the genetic distance required for LD to decay to $r^2=0.1$ or to 50% of the maximum estimated value, predicted using the aforementioned model.

LD appears to decay relatively rapidly in pepper: $r^2$ was estimated to reduce to 0.1 within 0.55 cM on LG6 and 1.65 cM on LG2 when elite hot and sweet pepper lines were considered together (e.g. see Table 13). Much of this diversity is attributable to hot pepper varieties: LD decays over 0.41 cM and 0.47 cM in LG6 and LG2, respectively. Conversely, for sweet pepper varieties, LD decays over 0.96 cM on LG6 and 2.47 cM on LG2. That is, for sweet peppers, LD appears to decay ~2.6 times slower on LH2 than LG6. Within sweet pepper varieties, the difference in LD decay is more substantial between bell (blocky; "SB") and mini ("SM") peppers, although LD and LD decay estimates are affected by sample size. For bell peppers, LD decays almost three times slower on LG2 than LG6, which is comparable to estimates of the total population studied.

Excluding all subpopulations with fewer than 20 lines, it takes up to 4.1 cM for LD to decay to $r^2=0.1$ on LG6 and up to 10 cM for LD to decay to $r^2=0.1$ on LG2. In consideration of immediate regions of the trait loci, LD decays to $r^2=0.1$ within 2 cM at the CCS locus and 4 cM at the Ze locus. Moreover, LD decay estimates surrounding the traits were very different to those observed for entire linkage groups. When only six relevant pepper types (where mature color varies and where color markers are thus most likely to be useful) were examined, LD decay surrounding Ccs was estimated as unchanged compared to the rest of the linkage group but was 1.5-times faster surrounding Ze than the rest of LG2. Thus, the presumptive causal mutation in Ze described here is of particular value when compared to a physically linked SNP since LD decays relatively rapidly around this locus.

TABLE 13

Summary of LD decay estimates on LG6 and LG2 for each subpopulation. S[BM]RY0 indicates the combined population of six pepper types: SBR (i.e. sweet, bell, red subpopulation), SBY (i.e. sweet, bell, yellow subpopulation), SBO (i.e. sweet, bell,orange subpopulation), SMR (i.e. sweet, mini, red subpopulation), SMY (i.e. sweet, mini, yellow subpopulation), and SMO. "cM to ½ $r^2_{max}$ " is the genetic distance in cM for $r^2$ to decay to 50% of its predicted maximum; "cM to $r^2$ = 0.1" is the genetic distance in cM for $r^2$ to decay to 0.1; L2:L6 is the ratio of LD decay estimates between LG2 and LG6.

| Sub-population | N | LG6 | | LG2 | | LG 2:LG6 | |
| --- | --- | --- | --- | --- | --- | --- | --- |
| | | cM to ½ $r^2_{max}$ | cM to $r^2$ = 0.1 | cM to ½ $r^2_{max}$ | c M to $r^2$ = 0.1 | cM to ½ $r^2_{max}$ | cM to $r^2$ = 0.1 |
| All | 882 | 0.06 | 0.55 | 0.18 | 1.65 | 2.99 | 2.99 |
| sweet | 537 | 0.11 | 0.96 | 0.27 | 2.47 | 2.57 | 2.57 |
| hot | 345 | 0.05 | 0.41. | 0.05 | 0.47 | 1.15 | 1.15 |
| bell | 319 | 021 | 1.87 | 0.60 | 5.43 | 2.90 | 2.90 |

TABLE 13-continued

Summary of LD decay estimates on LG6 and LG2 for each subpopulation. S[BM]RY0 indicates the combined population of six pepper types: SBR (i.e. sweet, bell, red subpopulation), SBY (i.e. sweet, bell, yellow subpopulation), SBO (i.e. sweet, bell,orange subpopulation), SMR (i.e. sweet, mini, red subpopulation), SMY (i.e. sweet, mini, yellow subpopulation), and SMO. "cM to ½ $r^2_{max}$" is the genetic distance in cM for $r^2$ to decay to 50% of its predicted maximum; "cM to $r^2 = 0.1$" is the genetic distance in cM for $r^2$ to decay to 0.1; L2:L6 is the ratio of LD decay estimates between LG2 and LG6.

| | | LG6 | | LG2 | | LG 2:LG6 | |
|---|---|---|---|---|---|---|---|
| Sub-population | N | cM to ½ $r^2_{max}$ | cM to $r^2 = 0.1$ | cM to ½ $r^2_{max}$ | c M to $r^2 = 0.1$ | cM to ½ $r^2_{max}$ | cM to $r^2 = 0.1$ |
| mini | 17 | 1.90 | 17.10 | 3.14 | 28.22 | 1.65 | 1.65 |
| red | 224 | 0.19 | 1.75 | 0.62 | 5.54 | 3.17 | 3.17 |
| yellow | 95 | 0.45 | 4.06 | 1.10 | 9.94 | 2.45 | 2.45 |
| orange | 17 | 1.07 | 9.67 | 5.78 | 52.06 | 5.39 | 5.39 |
| S[BM][RYO] | 339 | 0.40 | 1.78 | 0.62 | 5.56 | 1.55 | 3.12 |
| SBR | 221 | 0.40 | 1.80 | 0.71 | 6.36 | 1.77 | 3.53 |
| SBY | 89 | 0.66 | 4.11 | 0.68 | 6.09 | 1.03 | 1.48 |
| SBO | 12 | 1.64 | 12.99 | 4.99 | 44.87 | 3.03 | 3.45 |
| SMR | 5 | 13.05 | 115.66 | 12.06 | 108.54 | 0.92 | 0.94 |
| SMY | 6 | 52.51 | 470.75 | 9.60 | 86.39 | 0.18 | 0.18 |
| SMO | 6 | 14.26 | 126.53 | 47.19 | 424.75 | 3.31 | 3.36 |
| All (subregion) | 882 | 0.12 | 1.05 | 0.07 | 0.67 | 0.64 | 0.64 |
| S[BM][RYO] (subregion) | 339 | 0.61 | 1.93 | 0.42 | 3.82 | 0.69 | 1.97 |

Example 5

Breeding for Fruit Color Using Markers for Ccs and Ze

The identification of the presumptive causal SNPs in the two major color genes in pepper allows inference as to mature fruit color in pepper based on marker data. Table 14 shows the predicted fruit colors based on the markers NCANN009113770 (red vs. yellow; based on the Ccs gene) and NCANN009114570 (yellow vs. orange based on the Ze gene). The Ccs red allele is dominant to the yellow allele, and the yellow Ze allele is dominant to the orange allele. Therefore, a plant heterozygous for both genes has red fruits.

TABLE 14

Expected fruit colors based on Ccs and Ze genotypes.

| | | | NCANN009113770 | | |
|---|---|---|---|---|---|
| | | | INSINS CCSCCS | INSDEL CCsccs | DELDEL ccsccs |
| NCANN009114570 | AA | ZEZE | Red | Red | Yellow |
| | AG | ZEze | Red | Red | Yellow |
| | GG | Zeze | Red* | Red* | Orange |

*Plants with a CCSCCSzeze genotype (red-orange fruits) are visually scored to have red fruits, however the carotenoid profile is more consistent with orange fruits. It is expected that the same is true of plants with the CCSccszeze genotype.

Figure 6:
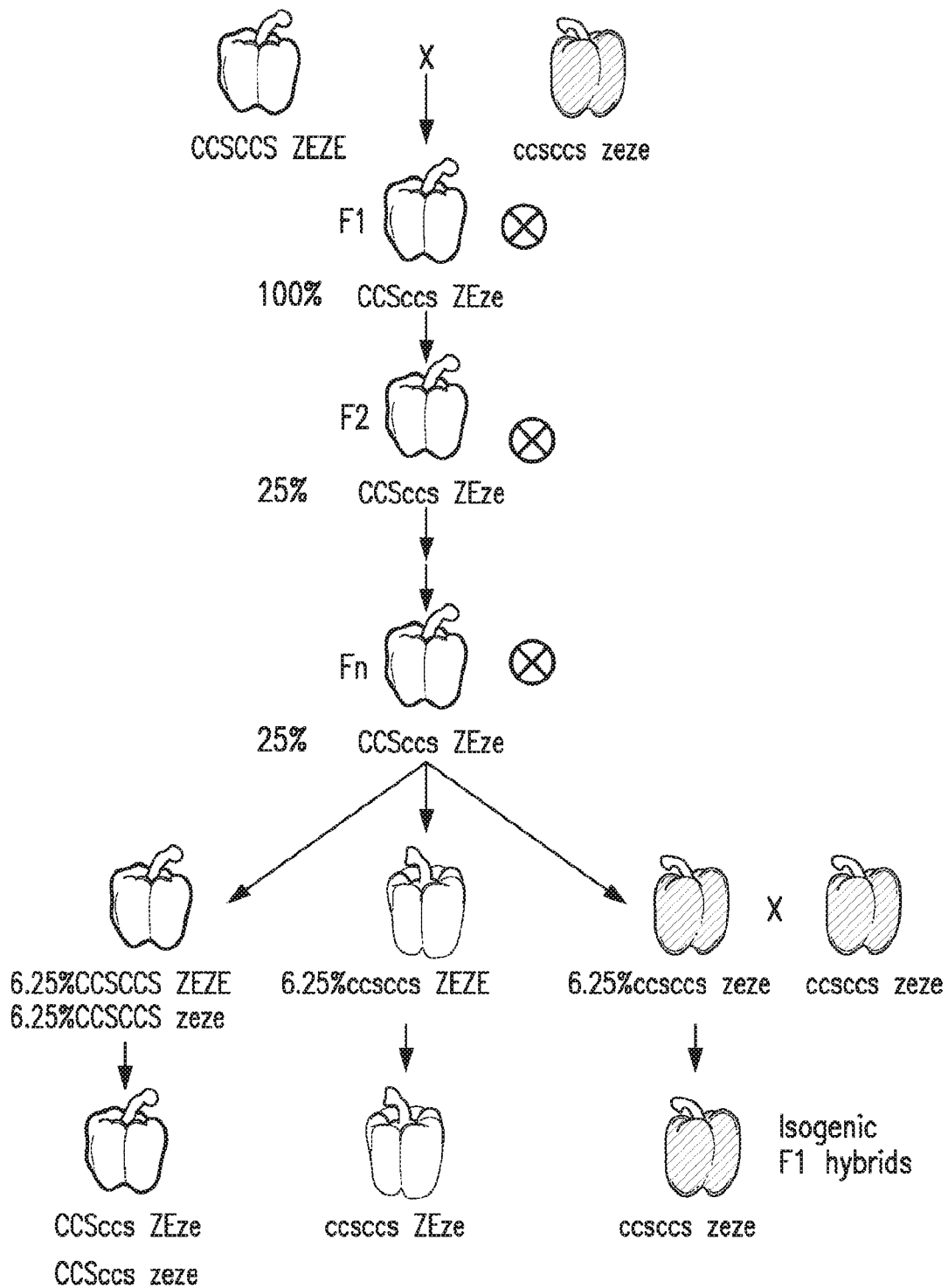
FIG. 6: An exemplary breeding scheme to create nearly isogenic orange, yellow, and red fruited pepper lines.

These two markers allow for marker assisted breeding in pepper for mature fruit color as described below. Sources of the genetic diversity described here exist in publically available germplasm. For example, diversity in the described color markers exists in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE). For instance, as discussed above, breeding for fruit color in peppers can be performed, wherein these color markers (or analogous linked markers) allow for simplification of multiple breeding programs based on color into one multi-color breeding program (FIG. 6). This can be achieved by crossing a red line that has both the intact Ccs and Ze alleles (CCSCCS ZEZE) with an orange line (ccsccs zeze) and maintaining both loci in a heterozygous state throughout the breeding process. In each generation, the subset of plants heterozygous for both color loci are selected with markers, and breeders may perform additional phenotypic selection on these plants. When the line is sufficiently genetically and phenotypically fixed after n generations the line can be selfed one final time and the progeny of the desired color genotype and phenotype can be selected using the markers for Ccs and Ze. This results in homozygous nearly isogenic lines that only differ in the mature fruit colors red, yellow and orange and loci tightly linked to the color loci. These nearly isogenic lines can be used to produce nearly isogenic hybrids, which are of interest because each of the differently colored nearly isogenic hybrids will have similar horticultural properties, allowing growers to manage each variety in the same way. Currently, red, yellow and orange commercial pepper varieties are each distinct and may each have different pruning, nutritional, or pest control needs, adding complexity and expense to operations producing more than one color type.

Figure 7:
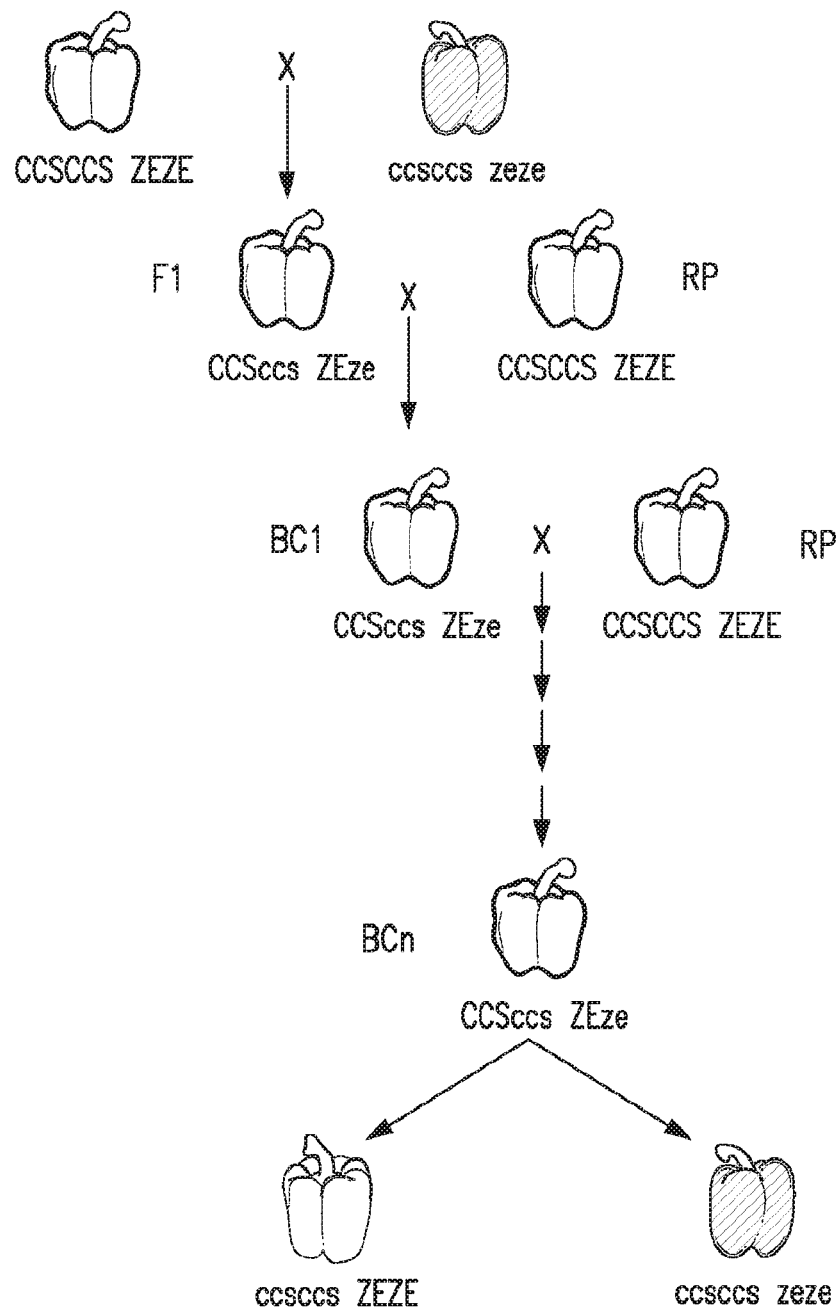
FIG. 7: Exemplary breeding scheme to create nearly isogenic orange, yellow, and red fruited pepper lines through marker assisted backcrossing ("MABC").

Isogenic inbred lines may also be created through marker assisted back crossing (MABC) using the new markers. Because red lines are typically the most advanced with respect to agronomic and disease traits, an improved orange or yellow line could be created by crossing an orange line with good color (color donor) to an elite red line with good agronomic and disease traits (recurrent parent). (FIG. 7).

Finally conventional marker-assisted breeding (MAS) can benefit greatly from the use of these color markers. Again, because red is the most economically important color and typically the most focused on for breeding efforts, MAS can be used to improve the orange and yellow germplasm. In a red by orange cross the red colored parent can be used to introduce more advanced agronomic traits while the orange parent is used to introduce the preferred color alleles. The color markers can be used to fix the color loci in the F2 generation and in subsequent generations, the lines with the best agronomic traits can be selected on a family basis. These methodologies may be used within and among any pepper species that are crossable in the genus Capsicum. For example these markers may be used to move these color mutations, and thus a desired fruit color phenotype, into any desired pepper genetic background.

SEQUENCE LISTING

<160> NUMBER OF SEQ ID NOS: 99

<210> SEQ ID NO 1
<211> LENGTH: 1497
<212> TYPE: DNA
<213> ORGANISM: Capsicum annuum

<400> SEQUENCE: 1

| | | | | | |
|---|---|---|---|---|---|
| atggaaaccc | ttctaaagcc | ttttccatct | cctttacttt | ccattcctac | tcctaacatg | 60 |
| tatagtttca | aacacaactc | cacttttcca | aatccaacca | aacaaaaaga | ttcaagaaag | 120 |
| ttccattata | gaaacaaaag | cagtacacat | ttttgtagct | ttcttgattt | agcacccaca | 180 |
| tcaaagccag | agtctttaga | tgttaacatc | tcatggggttg | atactgatct | ggacggggct | 240 |
| gaattcgacg | tgatcatcat | tggaactggc | cctgccgggc | ttcggctagc | tgaacaagtt | 300 |
| tctaaatatg | gtattaaggt | atgttgcgtt | gacccttcac | cactttccat | gtggccaaat | 360 |
| aattatggtg | tttgggttga | tgagtttgaa | aagttgggat | tagaagattg | tctagatcat | 420 |
| aagtggcctg | tgagttgtgt | tcatataagt | gatcacaaga | ctaagtattt | ggacagacca | 480 |
| tatggtagag | taagtagaaa | gaagttgaag | ttgaaattgt | tgaatagttg | tgttgaaaat | 540 |
| agagtgaagt | tttataaagc | caaggttttg | aaagtgaagc | atgaagaatt | tgagtcttcg | 600 |
| attgtttgtg | atgatggtag | gaagataagc | ggtagcttga | ttgttgatgc | aagtggctat | 660 |
| gctagtgatt | ttatagagta | tgacaagcca | agaaaccatg | gttatcaagt | tgctcatggg | 720 |
| attttagcag | aagttgataa | tcatccattt | gatttggata | aaatgatgct | tatggattgg | 780 |
| agggattctc | atttaggtaa | tgagccatat | ctgagggtga | agaatactaa | agaaccaaca | 840 |
| ttcttgtatg | caatgccatt | tgataggaat | ttggtattct | tggaagagac | ttctttagtg | 900 |
| agtcggccta | tgttatcgta | tatggaagtg | aaaagaagga | tggtagcaag | attaagacat | 960 |
| ttggggatca | aagtgagaag | tgtccttgag | gaagagaagt | gtgtgatcac | tatgggagga | 1020 |
| ccacttccgc | ggattcctca | aaatgttatg | gctattggtg | ggacttcagg | gatagttcat | 1080 |
| ccatcgtctg | ggtacatggt | ggctcgtagc | atggcattgg | caccagtact | ggctgaggcc | 1140 |
| atcgtcgaaa | gccttggctc | aacaagaatg | ataagagggt | ctcaacttta | ccatagagtt | 1200 |
| tggaatggtt | tgtggccttc | ggatagaaga | cgtgttagag | aatgttattg | tttcggaatg | 1260 |
| gagactttgt | tgaagcttga | tttggaaggt | actaggagat | tgtttgatgc | tttctttgat | 1320 |
| gttgatccca | agtactggca | cgggttcctt | tcttcaagat | tgtctgtcaa | agaacttgct | 1380 |
| gtactcagtt | tgtacctttt | tggacatgcc | tctaatttgg | ctaggttgga | tattgttaca | 1440 |
| aagtgcactg | tccccttggt | taaactgctg | ggcaatctag | caatagagag | cctttga | 1497 |

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
caactccact tttccaaatc                                              20

<210> SEQ ID NO 3
<211> LENGTH: 20
<212> TYPE: DNA
<213> ORGANISM: Artificial sequence
<220> FEATURE:
<223> OTHER INFORMATION: Primer

```
<400> SEQUENCE: 3
ggttgatact gatctggacg                                              20

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
gtgagtcggc ctatgttatc g                                            21

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
gtgagtcggc ctatgttatc g                                            21

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tgttgatccc aagtactggc                                              20

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
agacttggta tcagattgtg gc                                           22

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
agccacaatc cgataccaag                                              20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gagggacaag agtggagcag                                              20

<210> SEQ ID NO 10
```

-continued

```
<211> LENGTH: 20
<212> TYPE: DNA
<213> ORGANISM: Artificial sequence
<220> FEATURE:
<223> OTHER INFORMATION: Primer

<400> SEQUENCE: 10
tcgaaagcct tggctcaaca                                              20

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
ttttgtatct ccctttccca gaa                                          23

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
tctctaacac gtcttctatc cgaagg                                       26

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
agaatgataa gagggtct                                                18

<210> SEQ ID NO 14
<211> LENGTH: 18
<212> TYPE: DNA
<213> ORGANISM: Artificial sequence
<220> FEATURE:
<223> OTHER INFORMATION: Probe

<400> SEQUENCE: 14
cttttagagt ttggaatg                                                18

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
ccaaacactt tgaattggct ggata                                        25

<210> SEQ ID NO 16
<211> LENGTH: 36
<212> TYPE: DNA
<213> ORGANISM: Artificial sequence
<220> FEATURE:
<223> OTHER INFORMATION: Primer

<400> SEQUENCE: 16
```

```
actatattaa ctttcctaat aattcttgct ttccca                              36
```

<210> SEQ ID NO 17
<211> LENGTH: 22
<212> TYPE: DNA
<213> ORGANISM: Artificial sequence
<220> FEATURE:
<223> OTHER INFORMATION: Probe

<400> SEQUENCE: 17

```
tgctgttaat gattaataac at                                             22
```

<210> SEQ ID NO 18
<211> LENGTH: 20
<212> TYPE: DNA
<213> ORGANISM: Artificial sequence
<220> FEATURE:
<223> OTHER INFORMATION: Probe

<400> SEQUENCE: 18

```
ctgttaatga ttaaaaacat                                                20
```

<210> SEQ ID NO 19
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t

<400> SEQUENCE: 19

```
agccacaatc cgataccaag tctgtatttg gaagcacngn ctaattgtta tggttaccaa    60
acactttgaa ttggctggat aataacannn nggaaattta tgttwttaat cattaacagc  120
aaattgggaa agcaagaatt attaggaaag ttaatatagt gtcttggtta ttctaatgga  180
gtgggttatg caaattaagt tccctt                                       206
```

<210> SEQ ID NO 20
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t

<400> SEQUENCE: 20

```
agccacaatc cgataccaag tctgtatttg gaagcacngn ctaattgtta tggttaccaa    60
acactttgaa ttggctggat aataacannn nggaaattta tgttwttaat cattaacagc  120
```

| | |
|---|---:|
| aaattgggaa agcaagaatt attaggaaag ttaatatagt gtcttggtta ttctaatgga | 180 |
| gtgggttatg caaattaagt tccctt | 206 |

<210> SEQ ID NO 21
<211> LENGTH: 5105
<212> TYPE: DNA
<213> ORGANISM: Capsicum annuum
<220> FEATURE:
<221> NAME/KEY: misc_feature
<222> LOCATION: (4775)..(4775)
<223> OTHER INFORMATION: A may be either A or a deletion

<400> SEQUENCE: 21

| | |
|---|---:|
| tgttgaatgg aaatattgg aagaatttca tttcatttta caaaaataaa gagtgtagag | 60 |
| ggtattttg taaatcaata ttttttctat aaaaaatata aagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagtttttgta tctcccttc ccagaaatta agataattct ggtgctttta gcattagaaa | 360 |
| agtatttatt gggtagggaa atgtcatgac ttcacagcat taagcatcaa gggtataact | 420 |
| taatgaaata gtggtcaatg aatttatattg agaatgacga ggtctctgtt ccaactttgg | 480 |
| tagactttgg aaatgctcgt ctggacgccg cccattcttt ctagtcttgg tgccattcta | 540 |
| tttggtctga gactggcatg atgccaaatt ctaaccttt cacaatgagc attcgaccta | 600 |
| ctcttctttt ttacgactct atttgaccta ctaggcattg gccaacttgg ctaaccactt | 660 |
| gaggaactag agttcggatt caatagaatc taataatttt aatcaaaaga cttcatgtat | 720 |
| attgaaaat ctatttataa ctaactttaa atcggccttt acgtatcgac gtaatcaaaa | 780 |
| ttgtgtcagc ttgccacgtg gggtctagta tgagtttgaa attggtcata ggggccccaa | 840 |
| ttccactaat acagctgccg tcatgcact acaagacaaa tacaccacta tgttgttag | 900 |
| tgcttggtaa atgtaaaaca aacttttgat gagaatctat tcgtggcatc gaagtgctgc | 960 |
| aaattggctt ttacctctgc tacttcaagc ctcactgatt tcaccccaa ctttctcatt | 1020 |
| tcccttcaa ggatttgatt ttccagttgg gcatgttaaa acaacaatt ttcctcaaaa | 1080 |
| ctgtagaaat gatttytcat attttaatca gtcaaattat ttaaacaaga agttgatttt | 1140 |
| tttttaattt ttttttttac aaaaaaattt caaatgtcaa gtaagatttt tcaaattgaa | 1200 |
| actgaataag ctgcgacttt agaaacaaaa aactaagata agtaaaaata ccaaaaagag | 1260 |
| tgaatcacat caattgaatt cttccaacag ttcgtttttt agtttctgtt ttgggaagag | 1320 |
| gagtactaca aggtaggacc tccaacaatc aacaatatct aagttgcaaa agttttgtg | 1380 |
| cgttttttag tttctgtttc gagaagagga atactacaag ttcgttttt agtttctgtt | 1440 |
| ttgggaagag gagtactgca aggtaggacc tccaacaatt atcaatatct aaattgcaaa | 1500 |
| aattttcagtt cgttttagt ttctgtttcg ggaagaggaa tactacaagt tcgttttta | 1560 |
| gttctatttt tgggaagagg agtactacaa ggtaggacct ccaataccta aattgcaaaa | 1620 |
| atttcagttc gttttttagt ttcagtttag ggaagaggaa tactacaagg taggacctcc | 1680 |
| aacaatcatc agtacctaaa ttgcaaaaat ttcagttcgt tttttagttt atgtttggaa | 1740 |
| agaagaatac tacaaggcag tggcggagct acctatgat tagggggttc atccgaacct | 1800 |
| ccttcgacgg aaaattatac tatttttata agtgaaaatt atttttatg tatatataat | 1860 |
| tgatgttgaa cccccttcgg ttagttcatg tatctatatt tttttatttt gaaccccgat | 1920 |

```
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatatttttt    2700
tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttggg aagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttgggaagag aaatactaca agataggacc ttcaacaatc accaatacct    3300
aaattgcaaa aacttcagtt cattttttag tttctgtttt gggaagaaga atacttcaag    3360
gtaacaatca ccaataccta aawwaaattt cagttagttt tttagtttct gttttgggaa    3420
agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600 cctttttccat ctcctttact ttccattcct actcctaaca tgtatagttt caaacacaac    3660
tccacttttc caaatccaac caaacaaaaa gattcaagaa agttccatta tagaaacaaa    3720
agcagtacac attttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgaccctc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
```

```
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980 tttgacatg cctctaattt ggctaggttg gatattgtta caaagtgcac tgtccccttg    5040
gttaaactgc tgggcaatct agcaatagag agcctttgaa ttaatatgat agttttgaag    5100
cactg                                                                5105

<210> SEQ ID NO 22
<211> LENGTH: 678
<212> TYPE: DNA
<213> ORGANISM: Capsicum annuum

<400> SEQUENCE: 22
tgttgaatgg aaaatattgg aagaatttca tttcatttta caaaaataaa gagtgtagag      60
ggtatttttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctcccttt ccagaaatta agataattct ggtgctttta gagttttggaa     360 tggtttgtgg ccttcggata gaagacgtgt tagagaatgt tattgtttcg gaatggagac     420
tttgttgaag cttgatttgg aaggtactag gagattgttt gatgctttct ttgatgttga     480
tcccaagtac tggcacgggt tcctttcttc aagattgtct gtcaaagaac ttgctgtact     540
cagtttgtac cttttggac atgcctctaa tttggctagg ttggatattg ttacaaagtg     600
cactgtcccc ttggttaaac tgctgggcaa tctagcaata gagagccttt gaattaatat     660
gatagttttg aagcactg                                                   678

<210> SEQ ID NO 23
<211> LENGTH: 1000
<212> TYPE: DNA
<213> ORGANISM: Capsicum annuum
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
```

<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 23

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt accttttggg acatgcctct aatttggcta ggttggatat     240
tgttacaaag tgcactgtcc ccttggttaa actgctgggc aatctagcaa tagagagcct     300
ttgaattaat atgatagttt tgaagcactg ytttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca aacactttga attggctgga     600
taataacann nnggaatttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagttttttag                        1000
```

<210> SEQ ID NO 24
<211> LENGTH: 1000
<212> TYPE: DNA
<213> ORGANISM: Capsicum annuum
<220> FEATURE:

```
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 24
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttmtca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca acactttga attggctgga      600 taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
```

```
ttatctgtaa attgtcttcn ttgccattat tttaaaagtt taatnnnaag tgtaacatct      960
acaaagagtt gataattaca aagcagctac tagttttag                           1000
```

<210> SEQ ID NO 25
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (503)..(503)
<223> OTHER INFORMATION: G is either G or a deletion
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 25

```
tagagtttgg aatggtttgt ggccttcgga tagaagacgt gttagagaat gttattgttt       60
cggaatggag actttgttga agcttgattt ggaaggtact aggagattgt ttgatgcttt      120
ctttgatgtt gatcccaagt actggcacgg gttcctttct tcaagattgt ctgtcaaaga      180
acttgctgta ctcagtttgt accttttggg acatgcctct aatttggcta ggttggatat      240
tgttacaaag tgcactgtcc ccttggttaa actgctgggc aatctagcaa tagagagcct      300
ttgaattaat atgatagttt tgaagcactg ntttcatttt aatttcttag gttattttca      360
tcttttntca atgcaaaagt gaaacaaaag ctatacacat tgtcatcgtt gttcaaactc      420
```

```
agacaagttt gcctagctct atgtatttat ccttaacata tgtattcatc aaattcgaaa    480
tatacaatgt atggttgtcg atgcattgga caaaagtata gagccacaat cngataccaa    540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

<210> SEQ ID NO 26
<211> LENGTH: 986
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (595)..(598)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (931)..(933)
<223> OTHER INFORMATION: n is a, c, g, or t

<400> SEQUENCE: 26

```
tagagtttgg aatggtttgt ggccttcgga tagaagacgt gttagagaat gttattgttt     60
cggaatggag actttgttga agcttgattt ggaaggtact aggagattgt tgatgctttt    120
```

```
ctttgatgtt gatcccaagt actggcacgg gttcctttct tcaagattgt ctgtcaaaga      180
acttgctgta ctcagtttgt acctttttgg acatgcctct aatttggcta ggttggatat      240
tgttacaaag tgcactgtcc ccttggttaa actgctgggc aatctagcaa tagagagcct      300
ttgaattaat atgatagttt tgaagcactg ntttcatttt aatttcttag gttattttca      360
tcttttntca atgcaaaagt gaaacaaaag ctatacacat tgtcatcgtt gttcaaactc      420
agacaagttt gcctagctct atgtatttat ccttaacata tgtattcatc aaattcgaaa      480
tatacaatgc attggacaaa agtatagagc cacaatcnga taccaagtct gtatttggaa      540
gcacngncta attgttatgg ttaccaaaca ctttgaattg ctggataat aacannnngg       600 aantttatgt tattaatcat taacagcaaa ttgggaaagc aagaattatt aggaaagtta      660
atatagtgtc ttggttattc taatggagtg ggttatgcaa attaagttcc cttntcaaag      720
tttggtttat gaactgctcc actcntgtcc ctcttaaaag ccttaatccc aacatgtacc      780
accaaagaan tgagctgctc catcagatcc tttgagaatg ttaatatgtt atttaaatga      840
aggactgaat gattatgagg atgcaatgca taggtttaat taccagttat ctgtaaattg      900
tcttcnttgc cattatttta aaagtttaat nnnaagtgta acatctacaa agagttgata      960
attacaaagc agctactagt ttttag                                          986
```

```
<210> SEQ ID NO 27
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
```

<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 27

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt accttttgg acatgcctct aatttggcta ggttggatat     240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnn nnncattgga caaaagtata gagccacaat cygataccaa     540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

<210> SEQ ID NO 28
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 28

```
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacwg nctaattgtt atggttacca aacactttga attggctgga    600
taataacann nnggaantttt atgttattaa tcattaacag caaattggga aagcaagaat    660
tattaggaaa gttaatatag tgtcttggtt attctaatgg agtgggttat gcaaattaag    720
ttccctttntc aaagttttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

<210> SEQ ID NO 29
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:

<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 29

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttatttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnn nnncattgga caaaagtata gagccacaat cngataccaa    540
gtctgtattt ggaagcacng kctaattgtt atggttacca acactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                        1000
```

<210> SEQ ID NO 30
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature

```
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (612)..(612)
<223> OTHER INFORMATION: A may be either A or a deletion
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 30
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt accttttttgg acatgcctct aatttggcta ggttggatat     240
tgttacaaag tgcactgtcc ccttggtaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540 gtctgtatt ggaagcacng nctaattgtt atggttacca aacactttga attggctgga     600
taataacaaa caggaantt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagttttag                         1000
```

<210> SEQ ID NO 31
<211> LENGTH: 996
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (941)..(943)
<223> OTHER INFORMATION: n is a, c, g, or t

<400> SEQUENCE: 31

| | | | | | |
|---|---|---|---|---|---|
| tagagtttgg | aatggtttgt | ggccttcgga | tagaagacgt | gttagagaat | gttattgttt | 60 |
| cggaatggag | actttgttga | agcttgattt | ggaaggtact | aggagattgt | ttgatgcttt | 120 |
| ctttgatgtt | gatcccaagt | actggcacgg | gttcctttct | tcaagattgt | ctgtcaaaga | 180 |
| acttgctgta | ctcagtttgt | accttttggg | acatgcctct | aatttggcta | ggttggatat | 240 |
| tgttacaaag | tgcactgtcc | ccttggttaa | actgctgggc | aatctagcaa | tagagagcct | 300 |
| ttgaattaat | atgatagttt | tgaagcactg | ntttcatttt | aatttcttag | gttattttca | 360 |
| tcttttntca | atgcaaaagt | gaaacaaaag | ctatacacat | tgtcatcgtt | gttcaaactc | 420 |
| agacaagttt | gcctagctct | atgtatttat | ccttaacata | tgtattcatc | aaattcgaaa | 480 |
| tatacaatgn | nnnnnnnnnn | nnncattgga | caaaagtata | gagccacaat | cngataccaa | 540 |
| gtctgtattt | ggaagcacng | nctaattgtt | atggttacca | aacactttga | attggctgga | 600 |
| taataacagg | aantttatgt | tattaatcat | taacagcaaa | ttgggaaagc | aagaattatt | 660 |
| aggaaagtta | atatagtgtc | ttggttattc | taatggagtg | ggttatgcaa | attaagttcc | 720 |

```
cttntcaaag tttggtttat gaactgctcc actcntgtcc ctcttaaaag ccttaatccc      780
aacatgtacc accaaagaan tgagctgctc catcagatcc tttgagaatg ttaatatgtt      840
atttaaatga aggactgaat gattatgagg atgcaatgca taggtttaat taccagttat      900
ctgtaaattg tcttcnttgc cattatttta aaagtttaat nnnaagtgta acatctacaa      960
agagttgata attacaaagc agctactagt ttttag                                996
```

```
<210> SEQ ID NO 32
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 32
tagagtttgg aatggtttgt ggccttcgga tagaagacgt gttagagaat gttattgttt       60
cggaatggag actttgttga agcttgattt ggaaggtact aggagattgt ttgatgcttt      120
ctttgatgtt gatcccaagt actggcacgg gttcctttct tcaagattgt ctgtcaaaga      180
acttgctgta ctcagtttgt acctttttgg acatgcctct aatttggcta ggttggatat      240
tgttacaaag tgcactgtcc ccttggttaa actgctgggc aatctagcaa tagagagcct      300
ttgaattaat atgatagttt tgaagcactg ntttcatttt aatttcttag gttattttca      360
```

```
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca acactttga attggctgga    600 taataacann nnggaamttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

```
<210> SEQ ID NO 33
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 33
tagagtttgg aatggtttgt ggccttcgga tagaagacgt gttagagaat gttattgttt    60
```

```
cggaatggag actttgttga agcttgattt ggaaggtact aggagattgt ttgatgcttt    120
ctttgatgtt gatcccaagt actggcacgg gttcctttct tcaagattgt ctgtcaaaga    180
acttgctgta ctcagtttgt accttttggg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcattt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaantt atgttattaa tcattaacag caaattggga aagcaagaat    660
tattaggaaa gttaatatag tgtcttggtt attctaatgg agtgggttat gcaaattaag    720
ttcccttrtc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000

<210> SEQ ID NO 34
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
```

<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 34

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg nttcattt aatttcttag gttattttca       360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnn nnncattgga caaaagtata gagccacaat cngataccaa      540
gtctgtattt ggaagcacng nctaattgtt atggttacca acactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactckt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct      960
acaaagagtt gataattaca aagcagctac tagtttttag                           1000
```

<210> SEQ ID NO 35
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 35

| | | | | | |
|---|---|---|---|---|---|
| tagagtttgg | aatggtttgt | ggccttcgga | tagaagacgt | gttagagaat | gttattgttt | 60 |
| cggaatggag | actttgttga | agcttgattt | ggaaggtact | aggagattgt | ttgatgcttt | 120 |
| ctttgatgtt | gatcccaagt | actggcacgg | gttcctttct | tcaagattgt | ctgtcaaaga | 180 |
| acttgctgta | ctcagtttgt | acctttttgg | acatgcctct | aatttggcta | ggttggatat | 240 |
| tgttacaaag | tgcactgtcc | ccttggttaa | actgctgggc | aatctagcaa | tagagagcct | 300 |
| ttgaattaat | atgatagttt | tgaagcactg | ntttcatttt | aatttcttag | gttattttca | 360 |
| tcttttntca | atgcaaaagt | gaaacaaaag | ctatacacat | tgtcatcgtt | gttcaaactc | 420 |
| agacaagttt | gcctagctct | atgtatttat | ccttaacata | tgtattcatc | aaattcgaaa | 480 |
| tatacaatgn | nnnnnnnnnn | nnncattgga | caaaagtata | gagccacaat | cngataccaa | 540 |
| gtctgtattt | ggaagcacng | nctaattgtt | atggttacca | aacactttga | attggctgga | 600 |
| taataacann | nnggaanttt | atgttattaa | tcattaacag | caaattggga | aagcaagaat | 660 |
| tattaggaaa | gttaatatag | tgtcttggtt | attctaatgg | agtgggttat | gcaaattaag | 720 |
| ttcccttntc | aaagtttggt | ttatgaactg | ctccactcnt | gtccctctta | aaagccttaa | 780 |
| tcccaacatg | taccaccaaa | gaaytgagct | gctccatcag | atcctttgag | aatgttaata | 840 |
| tgttatttaa | atgaaggact | gaatgattat | gaggatgcaa | tgcataggtt | taattaccag | 900 |
| ttatctgtaa | attgtcttcn | ttgccattat | tttaaaagtt | taatnnnaag | tgtaacatct | 960 |
| acaaagagtt | gataattaca | aagcagctac | tagttttag | | | 1000 |

<210> SEQ ID NO 36
<211> LENGTH: 1000
<212> TYPE: DNA
<213> ORGANISM: Capsicum annum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)

<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 36

```
tagagtttgg aatggtttgt ggccttcgga tagaagacgt gttagagaat gttattgttt    60
cggaatggag actttgttga agcttgattt ggaaggtact aggagattgt ttgatgcttt   120
ctttgatgtt gatcccaagt actggcacgg gttcctttct tcaagattgt ctgtcaaaga   180
acttgctgta ctcagtttgt accttttgg acatgcctct aatttggcta ggttggatat   240
tgttacaaag tgcactgtcc ccttggttaa actgctgggc aatctagcaa tagagagcct   300
ttgaattaat atgatagttt tgaagcactg ntttcatttt aatttcttag gttattttca   360
tcttttntca atgcaaaagt gaaacaaaag ctatacacat tgtcatcgtt gttcaaactc   420
agacaagttt gcctagctct atgtatttat ccttaacata tgtattcatc aaattcgaaa   480
tatacaatgn nnnnnnnnnn nnncattgga caaaagtata gagccacaat cngataccaa   540
gtctgtattt ggaagcacng nctaattgtt atggttacca aacactttga attggctgga   600
taataacann nnggaanttt atgttattaa tcattaacag caaattggga aagcaagaat   660
tattaggaaa gttaatatag tgtcttggtt attctaatgg agtgggttat gcaaattaag   720
ttcccttntc aaagtttggt ttatgaactg ctccactcnt gtccctctta aaagccttaa   780
tcccaacatg taccaccaaa gaantgagct gctccatcag atcctttgag aatgttaata   840
tgttatttaa atgaaggact gaatgattat gaggatgcaa tgcataggtt taattaccag   900
ttatctgtaa attgtcttck ttgccattat tttaaaagtt taatnnnaag tgtaacatct   960
acaaagagtt gataattaca aagcagctac tagttttag                        1000
```

<210> SEQ ID NO 37
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

```
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (947)..(947)
<223> OTHER INFORMATION: C may be either C or a deletion

<400> SEQUENCE: 37
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taataacaag tgtaacatct     960
```
acaaagagtt gataattaca aagcagctac tagttttag       1000

<210> SEQ ID NO 38
<211> LENGTH: 997
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t

<400> SEQUENCE: 38
tagagtttgg aatggtttgt ggccttcgga tagaagacgt gttagagaat gttattgttt        60
cggaatggag actttgttga agcttgattt ggaaggtact aggagattgt ttgatgcttt       120
ctttgatgtt gatcccaagt actggcacgg gttcctttct tcaagattgt ctgtcaaaga       180
acttgctgta ctcagtttgt acctttttgg acatgcctct aatttggcta ggttggatat       240
tgttacaaag tgcactgtcc ccttggttaa actgctgggc aatctagcaa tagagagcct       300
ttgaattaat atgatagttt tgaagcactg ntttcatttt aatttcttag gttattttca       360
tcttttntca atgcaaaagt gaaacaaaag ctatacacat tgtcatcgtt gttcaaactc       420
agacaagttt gcctagctct atgtatttat ccttaacata tgtattcatc aaattcgaaa       480
tatacaatgn nnnnnnnnnn nnncattgga caaaagtata gagccacaat cngataccaa       540
gtctgtattt ggaagcacng nctaattgtt atggttacca aacactttga attggctgga       600
taataacann nnggaantttt atgttattaa tcattaacag caaattggga aagcaagaat      660

```
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taataagtgt aacatctaca    960
aagagttgat aattacaaag cagctactag tttttag                             997

<210> SEQ ID NO 39
<211> LENGTH: 14
<212> TYPE: DNA
<213> ORGANISM: Capsicum annuum

<400> SEQUENCE: 39
tatggttgtc gatg                                                       14

<210> SEQ ID NO 40
<211> LENGTH: 5736
<212> TYPE: DNA
<213> ORGANISM: Capsicum annuum

<400> SEQUENCE: 40
tgttgaatgg aaatattgg aagaatttca tttcattta caaaaataaa gagtgtagag        60 ggtattttg taaatcaata ttttttctat aaaaaatata taagaaatat tattttaata      120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300 aagtttgta tctcccttc ccagaaatta agataattct ggtgctttta gcattagaaa      360
agtatttatt gggtagggaa atgtcatgac ttcacagcat taagcatcaa gggtataact     420
taatgaaata gtggtcaatg aattatattg agaatgacga ggtctctgtt ccaactttgg     480
tagactttgg aaatgctcgt ctggacgccg cccattcttt ctagtcttgg tgccattcta     540
tttggtctga gactggcatg atgccaaatt ctaacctttt cacaatgagc attcgaccta     600
ctcttctttt ttacgactct atttgaccta ctaggcattg gccaacttgg ctaaccactt     660
gaggaactag agttcggatt caatagaatc taataatttt aatcaaaaga cttcatgtat     720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag     900
tgcttggtaa atgtaaaaca aactttgat gagaatctat tcgtggcatc gaagtgctgc     960
aaattggctt ttacctctgc tacttcaagc ctcactgatt ttcaccccaa ctttctcatt    1020
tccctttcaa ggatttgatt ttccagttgg gcatgttaaa acaacaatt ttcctcaaaa    1080 ctgtagaaat gatttctcat attttaatca gtcaaattat ttaaacaaga agttgatttt    1140
tttttaattt ttttttttac aaaaaaattt caaatgtcaa gtaagatttt tcaaattgaa    1200
actgaataag ctgcgacttt agaaacaaaa actaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa gttttttgtg    1380
cgttttttag tttctgtttc gagaagagga atactacaag ttcgtttttt agtttctgtt   1440
```

```
ttgggaagag gagtactgca aggtaggacc tccaacaatt atcaatatct aaattgcaaa    1500
aatttcagtt cgttttttagt ttctgtttcg ggaagaggaa tactacaagt tcgttttta    1560 gtttctattt tgggaagagg agtactacaa ggtaggacct ccaatacctc aattgcaaaa    1620
atttcagttc gttttttagt ttcagtttag ggaagaggaa tactacaagg taggacctcc    1680
aacaatcatc agtacctaaa ttgcaaaaat ttcagttcgt ttttagtttt atgtttggga    1740
agaagaatac tacaaggcag tggcggagct accttatgat taggggttc atccgaacct     1800 ccttcgacgg aaaattatac tatttttata agtgaaaatt attttttatg tatatataat    1860
tgatgttgaa cccccttcgg ttagttcatg tatctatatt ttttattttt gaaccccgat    1920 gaaattttg gctccgccac tgctacaagg taggacctcc aacaatcacc aatacctaaa     1980
ttgcaaaaat ttcagtttgt ttttagtttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt tgggaagag gaatactaca aggcagtggc ggagctacct tatgattagg    2580
ggttcatccg aacctccttc gacggaaaat tatactattt ttatatagta aaaattattt    2640
tttatgtata taattgat gttgaacccc cttcggttag tttgtgtatc tattttttt      2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctattttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt tagtttcta ttttgggaag tggaatagta    3180
taaggtagga cctccaacaa tcaccaatac ctaaattgca aaagttccga ttctttttt    3240 agtttctgtt ttggaaagag aaatactaca agataggacc ttcaacaatc accaatacct    3300
aaattgcaaa aacttcagtt cattttttag tttctgtttt gggaagaaga atacttcaag    3360
gtaacaatca ccaatacta aattaaattt cagttagttt tttagtttct gttttggga     3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaaatagccat tataaatctt gcattttctc taatgaaaac ccttctaaag    3600 cctttttccat ctcctttact ttccattcct actcctaaca tgtatagttt caaacacaac    3660
tccacttttc caaatccaac caaacaaaaa gattcaagaa agttccatta tagaaacaaa    3720
agcagtacac atttttgtag ctttcttgat ttagcaccca catcaaagcc agagtcttta    3780
gatgttaaca tctcatgggt tgatactgat ctggacgggg ctgaattcga cgtgatcatc    3840
```

```
attggaactg ccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg atattgtta caaagtgcac tgtccccttg     5040
gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga aatgttaat atgttattta aatgaaggac tgaatgatta tgaggatgca    5640
atgcataggt ttaattacca gttatctgta aattgtcttc tttgccatta ttttaaaagt    5700
ttaataacaa gtgtaacatc tacaaagagt tgataa                              5736
```

<210> SEQ ID NO 41
<211> LENGTH: 5736
<212> TYPE: DNA
<213> ORGANISM: Capsicum annuum

<400> SEQUENCE: 41

```
tgttgaatgg aaaatattgg aagaatttca tttcatttta caaaaataaa gagtgtagag      60
ggtattttg taaatcaata ttttttctat aaaaaatata taagaaatat tattttaata     120
catcaaatca aatactgtat aagaaataat gttaacataa ttaatgcaag tatagctaat     180
```

```
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttt cacaatgagc attcgaccta    600
ctcttctttt ttacgactct atttgaccta ctaggcattg ccaacttgg ctaaccactt    660 gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt tcaccccaa ctttctcatt   1020 tccctttcaa ggatttgatt ttccagttgg gcatgttaaa acaacaatt ttcctcaaaa   1080 ctgtagaaat gatttctcat atttaatca gtcaaattat ttaaacaaga agttgatttt   1140
tttttaattt ttttttttac aaaaaaattt caaatgtcaa gtaagatttt tcaaattgaa   1200
actgaataag ctgcgacttt agaaacaaaa aactaagata agtaaaaata ccaaaaagag   1260
tgaatcacat caattgaatt cttccaacag ttcgtttttt agtttctgtt ttgggaagag   1320
gagtactaca aggtaggacc tccaacaatc aacaatatct aagttgcaaa gttttttgtg   1380
cgttttttag tttctgtttc gagaagagga atactacaag ttcgtttttt agtttctgtt   1440
ttgggaagag gagtactgca aggtaggacc tccaacaatt atcaatatct aaattgcaaa   1500
aatttcagtt cgtttttagt ttctgtttcg gaagaggaa tactacaagt tcgttttta    1560 gtttctatt tgggaagagg agtactacaa ggtaggacct ccaataccta aattgcaaaa   1620
atttcagttc gttttttagt ttcagtttag ggaagaggaa tactacaagg taggacctcc   1680
aacaatcatc agtacctaaa ttgcaaaaat ttcagttcgt ttttagttt atgtttggga   1740 agaagaatac tacaaggcag tggcggagct accttatgat tagggggttc atccgaacct   1800
ccttcgacgg aaaattatac tattttata agtgaaaatt attttttatg tatatataat   1860
tgatgttgaa ccccccttcgg ttagttcatg tatctatatt ttttattttt gaaccccgat   1920
gaaaattttg gctccgccac tgctacaagg taggacctcc aacaatcacc aatacctaaa   1980
ttgcaaaaat ttcagtttgt ttttagttt ctgttttggg aagaggaata ctacaaggta   2040
ggacctccaa caatcaccaa tacctaaatt gcaacgtttt tttagtttct gttttgggaa   2100
gaggaatact acatggtagg gcctccaaca atcaccaata cctaaattgc aaaaatttca   2160
gttcgtattt tcgtttctat tttgggaagt ggaatagtat aaggtaggac ctccaacaat   2220
caccaatacc taaattaaag ttccgattca ttttttagtt tctgtttttgg aaagagaaat   2280 actcaaggt agggcctaca acaatcacca gtacctaaat tgtaaaaatt tcagttcgtt   2340
ttttagtttc tattttgaga agaggaatgc tacaaggtag gcctacaac aatcaccagt   2400 acctaaattg taaaaatttc agttcgtttt tagttctg ttttgggaag aggaatacta   2460
caaggtaggc ccttcaacaa tcagcaatac ctaaattaca aaaatttcaa ttcgtttttt   2520
agtttctgtt ttgggaagag gaatactaca aggcagtggc ggagctacct tatgattagg   2580
```

-continued

```
ggttcatccg aacctccttc gacggaaaat tatactattt ttatatagta aaaattattt    2640
tttatgtata taaattgat gttgaacccc cttcggttag tttgtgtatc tatattttt     2700 tattttgaac ctccttgata aaaattttg actccgccat tgctacaagg tagaacctcc    2760
aacaatcacc aatacctaaa ttgcaaaaat ttcagttcgt tttttaattt ctgttttggg   2820
aagaggaata ctacaaggcc tccaacaatc accaatacct aaattgcaaa aatttcagtt   2880
tgttttttag tttctgtttt gggaagagga atactacaag gtaaggcctc caacaatcac   2940
caatacctaa attgcaaaaa tttcagttcg tattttcgtt tctattttgg gaagtggaat   3000
agtataaggt aggacctcca acaatcacca atacctaaat tgcaaaagtt ccgattcatt   3060
ttttagtttc tgttttggaa agagaaatac tacaaggtag gtctccaac aatcaccagt    3120 acctaaattg taaaaatttc agttcgtttt ttagtttcta ttttgggaag tggaatagta   3180
taaggtagga cctccaacaa tcaccaatac ctaaattgca aaagttccga ttcttttttt   3240
agtttctgtt ttggaaagag aaatactaca agataggacc ttcaacaatc accaatacct   3300
aaattgcaaa aacttcagtt catttttag tttctgtttt gggaagaaga atacttcaag    3360
gtaacaatca ccaatacctt aattaaattt cagttagttt tttagtttct gttttggga    3420 agaggaatac tttcttttgc tatataaagc caaagtaggt acctataagc atcaatattt   3480
tgtattgctt agtgattccc ctagttcggt atttcatttt ttttcactat actatatcac   3540
ctcctctcat aaatagccat tataaatctt gcattttctc taatgaaaac ccttctaaag   3600
ccttttccat ctcctttact ttccattcct actcctaaca tgtatagttt caaacacaac   3660 tccactttc caaatccaac caaacaaaaa gattcaagaa agttccatta tagaaacaaa    3720
agcagtacac attttgtag ctttcttgat ttagcaccca catcaaagcc agagtcttta    3780
gatgttaaca tctcatgggt tgatactgat ctggacgggg ctgaattcga cgtgatcatc   3840
attggaactg gccctgccgg gcttcggcta gctgaacaag tttctaaata tggtattaag   3900
gtatgttgcg ttgacccttc accactttcc atgtggccaa ataattatgg tgtttgggtt   3960
gatgagtttg aaaagttggg attagaagat tgtctagatc ataagtggcc tgtgagttgt   4020
gttcatataa gtgatcacaa gactaagtat ttggacagac catatggtag agtaagtaga   4080
aagaagttga agttgaaatt gttgaatagt tgtgttgaaa atagagtgaa gttttataaa   4140
gccaaggttt tgaaagtgaa gcatgaagaa tttgagtctt cgattgtttg tgatgatggt   4200
aggaagataa gcggtagctt gattgttgat gcaagtggct atgctagtga ttttatagag   4260
tatgacaagc caagaaacca tggttatcaa gttgctcatg ggattttagc agaagttgat   4320
aatcatccat ttgatttgga taaaatgatg cttatggatt ggagggattc tcatttaggt   4380
aatgagccat atctgagggt gaagaatact aaagaaccaa cattcttgta tgcaatgcca   4440
tttgatagga attttggtat cttggaagag acttctttag tgagtcggcc tatgttatcg   4500
tatatggaag tgaaagaag gatggtagca agattaagac atttggggat caaagtgaga   4560
agtgtccttg aggaagagaa gtgtgtgatc actatgggag gaccacttcc gcggattcct   4620
caaaatgtta tggctattgg tgggacttca gggatagttc atccatcgtc tgggtacatg   4680
gtggctcgta gcatggcatt ggcaccagta ctggctgagg ccatcgtcga aagccttggc   4740
tcaacaagaa tgataagagg gtctcaactt taccatagag tttggaatgg tttgtggcct   4800
tcggatagaa gacgtgttag agaatgttat tgtttcggaa tggagacttt gttgaagctt   4860
gatttggaag gtactaggag attgtttgat gctttctttg atgttgatcc caagtactgg   4920
```

```
cacgggttcc tttcttcaag attgtctgtc aaagaacttg ctgtactcag tttgtacctt    4980
tttggacatg cctctaattt ggctaggttg gatattgtta caaagtgcac tgtcccttg     5040 gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga aatgttaat  atgttattta aatgaaggac tgaatgatta tgaggatgca    5640
atgcataggt ttaattacca gttatctgta aattgtcttc tttgccatta tttttaaagt    5700
ttaataacaa gtgtaacatc tacaaagagt tgataa                             5736
```

<210> SEQ ID NO 42
<211> LENGTH: 5736
<212> TYPE: DNA
<213> ORGANISM: Capsicum annuum

<400> SEQUENCE: 42

```
tgttgaatgg aaatattgg  aagaatttca tttcatttta caaaaataaa gagtgtagag     60 ggtattttg  taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttt  cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgttgttag    900 tgcttggtaa atgtaaaaca aacttttgat gagaatctat tcgtggcatc gaagtgctgc    960
aaattggctt ttacctctgc tacttcaagc ctcactgatt ttcaccccaa ctttctcatt   1020
tccctttcaa ggatttgatt ttccagttgg gcatgttaaa acaacaatt  ttcctcaaaa   1080 ctgtagaaat gatttctcat attttaatca gtcaaattat ttaaacaaga agttgatttt   1140
tttttaattt ttttttttac aaaaaaattt caaatgtcaa gtaagatttt tcaaattgaa   1200
actgaataag ctgcgacttt agaaacaaaa aactaagata agtaaaaata ccaaaaagag   1260
tgaatcacat caattgaatt cttccaacag ttcgtttttt agtttctgtt ttgggaagag   1320
```

```
gagtactaca aggtaggacc tccaacaatc aacaatatct aagttgcaaa agttttttgtg    1380 cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg ggaagaggaa tactacaagt tcgtttttta    1560 gtttctatttt tgggaagagg agtactacaa ggtaggacct ccaataccta aattgcaaaa    1620
atttcagttc gttttttagt ttcagtttag gaagaggaa tactacaagg taggacctcc    1680
aacaatcatc agtacctaaa ttgcaaaaat ttcagttcgt ttttagttt atgtttggga    1740 agaagaatac tacaaggcag tggcggagct accttatgat tagggggttc atccgaacct    1800
ccttcgacgg aaaattatac tattttata agtgaaaatt attttttatg tatatataat    1860
tgatgttgaa cccccttcgg ttagttcatg tatctatatt tttttatttt gaaccccgat    1920
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160 gttcgtatttt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatatttttt    2700 tatttttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc aacaatcac    2940 caatacctaa attgcaaaaa tttcagttcg tattttcgtt tctatttgg gaagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt    3240 agtttctgtt ttggaaagag aaatactaca agataggacc ttcaacaatc accaatacct    3300
aaattgcaaa aacttcagtt catttttttag tttctgtttt gggaagaaga atacttcaag    3360
gtaacaatca ccaataccta aattaaattt cagttagttt tttagtttct gttttgggga    3420
agaggaatac tttcttttgc tatataaagc caaagtaggg acctataagc atcaatattt    3480
tgtattgctt agtgattccc ctagttcggt atttcatttt ttttcactat actatatcac    3540
ctcctctcat aaatagccat tataaatctt gcattttctc taatgaaaac ccttctaaag    3600 cctttttccat ctcctttact ttccattcct actcctaaca tgtatagttt caaacacaac    3660
```

-continued

```
tccacttttc caaatccaac caaacaaaaa gattcaagaa agttccatta tagaaacaaa      3720
agcagtacac atttttgtag cttcttgat ttagcaccca catcaaagcc agagtctta        3780 gatgttaaca tctcatgggt tgatactgat ctggacgggg ctgaattcga cgtgatcatc      3840
attggaactg gccctgccgg gcttcggcta gctgaacaag tttctaaata tggtattaag      3900
gtatgttgcg ttgacccttc accactttcc atgtggccaa ataattatgg tgtttgggtt     3960
gatgagtttg aaaagttggg attagaagat tgtctagatc ataagtggcc tgtgagttgt     4020
gttcatataa gtgatcacaa gactaagtat ttggacagac catatggtag agtaagtaga     4080
aagaagttga agttgaaatt gttgaatagt tgtgttgaaa atagagtgaa gttttataaa     4140
gccaaggttt tgaaagtgaa gcatgaagaa tttgagtctt cgattgtttg tgatgatggt     4200
aggaagataa gcggtagctt gattgttgat gcaagtggct atgctagtga ttttatagag     4260
tatgacaagc caagaaacca tggttatcaa gttgctcatg ggattttagc agaagttgat     4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gcttctttg atgttgatcc caagtactgg     4920
cacgggttcc tttcttcaag attgtctgtc aaagaacttg ctgtactcag tttgtacctt   4980
tttggacatg cctctaattt ggctaggttg gatattgtta caaagtgcac tgtcccttg     5040 gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga aatgttaat atgttattta aatgaaggac tgaatgatta tgaggatgca     5640
atgcataggt ttaattacca gttatctgta aattgtcttc tttgccatta ttttaaaagt    5700
ttaataacaa gtgtaacatc tacaaagagt tgataa                              5736
```

<210> SEQ ID NO 43
<211> LENGTH: 5736
<212> TYPE: DNA
<213> ORGANISM: Capsicum annuum

<400> SEQUENCE: 43

```
tgttgaatgg aaaatattgg aagaatttca tttcatttta caaaaataaa gagtgtagag      60
```

```
ggtattttg taaatcaata ttttttctat aaaaaatata taagaaatat tattttaata        120
catcaaatca aatactgtat aagaaataat gttaacataa ttaatgcaag tatagctaat        180
accaacatta ctaatgcaag tattactaat acaccatatt ctatattaat cttatatact        240
ctaccaaacg accctaagtg tgtatctata tcctccgaga atttggaatt tgcaaattcc        300
aagttttgta tctcccttc ccagaaatta agataattct ggtgctttta gcattagaaa        360
agtatttatt gggtagggaa atgtcatgac ttcacagcat taagcatcaa gggtataact        420
taatgaaata gtggtcaatg aattatattg agaatgacga ggtctctgtt ccaactttgg        480
tagactttgg aaatgctcgt ctggacgccg cccattcttt ctagtcttgg tgccattcta        540
tttggtctga gactggcatg atgccaaatt ctaacctttt cacaatgagc attcgaccta        600
ctcttctttt ttacgactct atttgaccta ctaggcattg gccaacttgg ctaaccactt        660
gaggaactag agttcggatt caatagaatc taataatttt aatcaaaaga cttcatgtat        720
attgaaaaat ctatttataa ctaactttaa atcggccttt acgtatcgac gtaatcaaaa        780
ttgtgtcagc ttgccacgtg gggtctagta tgagtttgaa attggtcata ggggcccccaa        840 ttccactaat acagctgccg tccatgcact acaagacaaa tacaccacta tgtttgttag        900
tgcttggtaa atgtaaaaca aacttttgat gagaatctat tcgtggcatc gaagtgctgc        960
aaattggctt ttacctctgc tacttcaagc ctcactgatt ttcaccccaa ctttctcatt       1020 tcccttcaa ggatttgatt ttccagttgg gcatgttaaa aacaacaatt ttcctcaaaa       1080
ctgtagaaat gatttctcat attttaatca gtcaaattat ttaaacaaga agttgatttt       1140
tttttaattt ttttttttac aaaaaaattt caaatgtcaa gtaagatttt tcaaattgaa       1200
actgaataag ctgcgacttt agaaacaaaa aactaagata agtaaaaata ccaaaaagag       1260
tgaatcacat caattgaatt cttccaacag ttcgtttttt agtttctgtt ttgggaagag       1320
gagtactaca aggtaggacc tccaacaatc aacaatatct aagttgcaaa agttttgtg      1380 cgttttttag tttctgtttc gagaagagga atactacaag ttcgtttttt agtttctgtt       1440
ttgggaagag gagtactgca aggtaggacc tccaacaatt atcaatatct aaattgcaaa       1500
aatttcagtt cgtttttagt ttctgtttcg ggaagaggaa tactacaagt tcgtttttta       1560
gtttctattt tgggaagagg agtactacaa ggtaggacct ccaataccta aattgcaaaa       1620
atttcagttc gttttttagt ttcagtttag ggaagaggaa tactacaagg taggacctcc       1680
aacaatcatc agtacctaaa ttgcaaaaat ttcagttcgt ttttagttt atgtttggga       1740 agaagaatac tacaaggcag tggcggagct accttatgat taggggggttc atccgaacct       1800 ccttcgacgg aaaattatac tattttata agtgaaaatt ttttttatg tatatataat       1860 tgatgttgaa ccccccttcgg ttagttcatg tatctatatt ttttattt gaaccccgat       1920 gaaaattttg gctccgccac tgctacaagg taggacctcc aacaatcacc aatacctaaa       1980
ttgcaaaaat ttcagtttgt ttttagtttt ctgttttggg aagaggaata ctacaaggta       2040
ggacctccaa caatcaccaa tacctaaatt gcaacgtttt tttagtttct gttttgggaa       2100
gaggaatact acatggtagg gcctccaaca atcaccaata cctaaattgc aaaaatttca       2160
gttcgtattt tcgtttctat tttgggaagt ggaatagtat aaggtaggac ctccaacaat       2220
caccaatacc taaattaaag ttccgattca ttttttagtt tctgttttgg aaagagaaat       2280
actacaaggt agggcctaca acaatcacca gtacctaaat tgtaaaaatt tcagttcgtt       2340
ttttagtttc tattttgaga agaggaatgc tacaaggtag ggcctacaac aatcaccagt       2400
```

```
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttt    2700
tattttgaac ctccttgata aaaattttg actccgccat tgctacaagg tagaacctcc    2760
aacaatcacc aatacctaaa ttgcaaaaat ttcagttcgt tttttaattt ctgtttgggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttgggaagag aaatactaca agataggacc ttcaacaatc accaatacct    3300
aaattgcaaa aacttcagtt catttttag tttctgtttt gggaagaaga atacttcaag    3360
gtaacaatca ccaatacctaa attaaattt cagttagttt tttagtttct gttttggga    3420
agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600
cctttttccat ctcctttact ttccattcct actcctaaca tgtatagttt caaacacaac    3660
tccacttttc caaatccaac caaacaaaaa gattcaagaa agttccatta tagaaacaaa    3720
agcagtacac atttttgtag ctttcttgat ttagcaccca catcaaagcc agagtcttta    3780
gatgttaaca tctcatgggt tgatactgat ctggaccggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gtggtagctt gattgttgat gcaagtggct atgctagtga ttttatagag    4260
tatgacaagc caagaaacca tggttatcaa gttgctcatg ggatttttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttgggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
```

```
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caaagtgcac tgtccccttg    5040
gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tctgatacca agtctgtatt tggaagcaca ggctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttgt caaagtttgg tttatgaact gctccactct    5520
tgtccctctt aaaagcctta atcccaacat gtaccaccaa agaattgagc tgctccatca    5580
gatcctttga aatgttaat atgttattta aatgaaggac tgaatgatta tgaggatgca    5640
atgcataggt ttaattacca gttatctgta aattgtcttc tttgccatta ttttaaaagt    5700
ttaataacaa gtgtaacatc tacaaagagt tgataa                             5736

<210> SEQ ID NO 44
<211> LENGTH: 5743
<212> TYPE: DNA
<213> ORGANISM: Capsicum annuum

<400> SEQUENCE: 44
tgttgaatgg aaatattgg aagaatttca tttcatttta caaaataaa gagtgtagag      60 ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttt cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggcccaa     840 ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt ttcacccaa ctttctcatt    1020 tcccttttcaa ggatttgatt ttccagttgg gcatgttaaa aacaacaatt ttcctcaaaa   1080
ctgtagaaat gatttctcat attttaatca gtcaaattat ttaaacaaga agttgatttt    1140
```

```
tttttaattt ttttttttac aaaaaaattt caaatgtcaa gtaagattt tcaaattgaa    1200 actgaataag ctgcgacttt agaaacaaaa aactaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa agttttgtg    1380 cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg ggaagaggaa tactacaagt tcgttttta    1560 gtttctatt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt ttttttagttt atgtttggga    1740 agaagaatac tacaaggcag tggcggagct accttatgat taggggttc atccgaacct    1800 ccttcgacgg aaaattatac tatttttata agtgaaaatt attttttatg tatatataat    1860
tgatgttgaa cccccttcgg ttagttcatg tatctatatt tttttatttt gaaccccgat    1920
gaaaattttg gctccgccac tgctacaagg taggacctcc aacaatcacc aatacctaaa    1980
ttgcaaaaat ttcagtttgt ttttagtttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata taattgat gttgaacccc cttcggttag tttgtgtatc tatattttt    2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttgg gaagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaagag aaatactaca agataggacc ttcaacaatc accaatacct    3300
aaattgcaaa aacttcagtt catttttag tttctgtttt gggaagaaga atacttcaag    3360
gtaacaatca ccaataccta aattaaattt cagttagttt tttagtttct gttttgggaa    3420
agaggaatac tttcttttgc tatataaagc caaagtaggg acctaaaagc atcaatattt    3480
tgtattgctt agtgattccc ctagttcggt atttcatttt ttttcactat actatatcac    3540
```

```
ctcctctcat aaatagccat tataaatctt gcattttctc taatggaaac ccttctaaag    3600
cctttccat ctcctttact ttccattcct actcctaaca tgtatagttt caaacacaac     3660
```
*(correction)*
```
ctcctctcat aaatagccat tataaatctt gcattttctc taatggaaac ccttctaaag    3600
cctttccat ctcctttact ttccattcct actcctaaca tgtatagttt caaacacaac     3660
tccactttc caaatccaac caaacaaaaa gattcaagaa agttccatta tagaaacaaa     3720
agcagtacac attttgtag ctttcttgat ttagcaccca catcaaagcc agagtcttta     3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggatttttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtaccct    4980
tttggacatg cctctaattt ggctaggttg gatattgtta caaagtgcac tgtccccttg    5040
gttaaactgc tgggcaatct agcaatagag agcctttgaa ttaatatgat agttttgaag    5100
cactgctttc atttaatttt cttaggttat tttcatcttt tatcaatgca aaagtgaaac    5160
aaaagctata cacattgtca tcgttgttca aactcagaca agtttgccta gctctatgta    5220
tttatcctta acatatgtat tcatcaaatt cgaaatatac aatgtatggt tgtcgatgca    5280
ttggacaaaa gtatagagcc acaatctgat accaagtctg tatttggaag cactggctaa    5340
ttgttatggt taccaaacac tttgaattgg ctggataata acaggaaatt tatgttatta    5400
atcattaaca gcaaattggg aaagcaagaa ttattaggaa agttaatata gtgtcttggt    5460
tattctaatg gagtgggtta tgcaaattaa gttcccttat caaagtttgg tttatgaact    5520
gctccactcg tgtccctctt aaaagcctta atcccaacat gtaccaccaa agaactgagc    5580
tgctccatca gatcctttga gaatgttaat atgttattta aatgaaggac tgaatgatta    5640
tgaggatgca atgcataggt ttaattacca gttatctgta aattgtcttc gttgccatta    5700
ttttaaaagt ttaataagtg taacatctac aaagagttga taa                     5743
```

<210> SEQ ID NO 45
<211> LENGTH: 5743
<212> TYPE: DNA

<213> ORGANISM: Capsicum annuum

<400> SEQUENCE: 45

```
tgttgaatgg aaaatattgg aagaatttca tttcatttta caaaaataaa gagtgtagag    60
ggtattttg taaatcaata ttttttctat aaaaaatata taagaaatat tattttaata   120
catcaaatca aatactgtat aagaaataat gttaacataa ttaatgcaag tatagctaat   180
accaacatta ctaatgcaag tattactaat acaccatatt ctatattaat cttatatact   240
ctaccaaacg accctaagtg tgtatctata tcctccgaga atttggaatt tgcaaattcc   300
aagttttgta tctcccttc ccagaaatta agataattct ggtgctttta gcattagaaa    360
agtatttatt gggtagggaa atgtcatgac ttcacagcat taagcatcaa gggtataact   420
taatgaaata gtggtcaatg aattatattg agaatgacga ggtctctgtt ccaactttgg   480
tagactttgg aaatgctcgt ctggacgccg cccattcttt ctagtcttgg tgccattcta   540
tttggtctga gactggcatg atgccaaatt ctaccttttt cacaatgagc attcgaccta   600
ctcttctttt ttacgactct atttgaccta ctaggcattg ccaacttggg ctaaccactt   660
gaggaactag agttcggatt caatagaatc taataatttt aatcaaaaga cttcatgtat   720
attgaaaaat ctatttataa ctaactttaa atcggccttt acgtatcgac gtaatcaaaa   780
ttgtgtcagc ttgccacgtg gggtctagta tgagtttgaa attggtcata ggggccccaa   840
ttccactaat acagctgccg tccatgcact acaagacaaa tacaccacta tgtttgttag   900
tgcttggtaa atgtaaaaca aacttttgat gagaatctat tcgtggcatc gaagtgctgc   960
aaattggctt ttacctctgc tacttcaagc ctcactgatt ttcaccccaa ctttctcatt  1020
tccctttcaa ggatttgatt ttccagttgg gcatgttaaa acaacaattt ttcctcaaaa  1080
ctgtagaaat gatttctcat attttaatca gtcaaattat ttaaacaaga agttgatttt  1140
tttttaattt ttttttttac aaaaaaattt caaatgtcaa gtaagatttt tcaaattgaa  1200
actgaataag ctgcgacttt agaaacaaaa aactaagata agtaaaaata ccaaaaagag  1260
tgaatcacat caattgaatt cttccaacag ttcgtttttt agtttctgtt tgggaagag   1320
gagtactaca aggtaggacc tccaacaatc aacaatatct aagttgcaaa gttttttgtg  1380
cgttttttag tttctgtttc gagaagagga atactacaag ttcgtttttt agtttctgtt  1440
ttgggaagag gagtactgca aggtaggacc tccaacaatt atcaatatct aaattgcaaa  1500
aatttcagtt cgttttttagt ttctgtttcg ggaagaggaa tactacaagt tcgttttta   1560
gtttctattt tgggaagagg agtactacaa ggtaggacct ccaataccta aattgcaaaa  1620
atttcagttc gttttttagt ttcagtttag ggaagaggaa tactacaagg taggacctcc  1680
aacaatcatc agtacctaaa ttgcaaaaat ttcagttcgt tttttagttt atgtttggga  1740
agaagaatac tacaaggcag tggcggagct accttatgat taggggttc atccgaacct   1800
ccttcgacgg aaaattatac tattttttata agtgaaaatt attttttatg tatatataat  1860
tgatgttgaa ccccccttcgg ttagttcatg tatctatatt tttttatttt gaaccccgat  1920
gaaaattttg gctccgccac tgctacaagg taggacctcc aacaatcacc aatacctaaa  1980
ttgcaaaaat ttcagtttgt tttttagttt ctgtttggg aagaggaata ctacaaggta   2040
ggacctccaa caatcaccaa tacctaaatt gcaacgtttt tttagtttct gttttgggaa  2100
gaggaatact acatggtagg gcctccaaca atcaccaata cctaaattgc aaaaatttca  2160
gttcgtattt tcgtttctat tttgggaagt ggaatagtat aaggtaggac ctccaacaat  2220
caccaatacc taaattaaag ttccgattca ttttttagtt tctgttttgg aaagagaaat  2280
```

```
actacaaggt agggcctaca acaatcacca gtacctaaat tgtaaaaatt tcagttcgtt    2340
tttagttttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacgaaaat tatactattt ttatatagta aaaattattt     2640
tttatgtata tataattgat gttgaacccc cttcggttag tttgtgtatc tatatttttt    2700
tattttgaac ctccttgata aaaattttg actccgccat tgctacaagg tagaacctcc     2760
aacaatcacc aatacctaaa ttgcaaaaat ttcagttcgt ttttaattt ctgttttggg     2820 aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttgg gaagtggaat     3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt     3240 agtttctgtt ttgggaagag aaatactaca agataggacc ttcaacaatc accaatacct    3300
aaattgcaaa aacttcagtt catttttag tttctgtttt gggaagaaga atacttcaag     3360
gtaacaatca ccaatacctaa attaaatttt cagttagttt tttagtttct gttttggga    3420 agaggaatac tttctttgc tatataaagc caaagtaggt acctataagc atcaatattt     3480
tgtattgctt agtgattccc ctagttcggt atttcatttt ttttcactat actatatcac    3540
ctcctctcat aaatagccat tataaatctt gcatttctc taatgaaaac ccttctaaag    3600
ccttttccat ctccttact ttccattcct actcctaaca tgtatagttt caaacacaac    3660 tccactttc caaatccaac caaacaaaaa gattcaagaa agttccatta tagaaacaaa    3720
agcagtacac atttttgtag cttttcttgat ttagcaccca catcaaagcc agagtcttta   3780
gatgttaaca tctcatgggt tgatactgat ctggacgggg ctgaattcga cgtgatcatc    3840 attgaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat tgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
```

```
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caaagtgcac tgtccccttg    5040
gttaaactgc tgggcaatct agcaatagag agcctttgaa ttaatatgat agttttgaag    5100
cactgctttc attttaattt cttaggttat tttcatcttt tatcaatgca aaagtgaaac    5160
aaaagctata cacattgtca tcgttgttca aactcagaca agtttgccta gctctatgta    5220
tttatcctta acatatgtat tcatcaaatt cgaaatatac aatgtatggt tgtcgatgca    5280
ttggacaaaa gtatagagcc acaatctgat accaagtctg tatttggaag cactggctaa    5340
ttgttatggt taccaaacac tttgaattgg ctggataata acaggaaatt tatgttatta    5400
atcattaaca gcaaattggg aaagcaagaa ttattaggaa agttaatata gtgtcttggt    5460
tattctaatg gagtgggtta tgcaaattaa gttcccttat caaagtttgg tttatgaact    5520
gctccactcg tgtccctctt aaaagcctta atcccaacat gtaccaccaa agaactgagc    5580
tgctccatca gatcctttga gaatgttaat atgttattta aatgaaggac tgaatgatta    5640
tgaggatgca atgcataggt ttaattacca gttatctgta aattgtcttc gttgccatta    5700
ttttaaaagt ttaataagtg taacatctac aaagagttga taa                     5743

<210> SEQ ID NO 46
<211> LENGTH: 5743
<212> TYPE: DNA
<213> ORGANISM: Capsicum annuum

<400> SEQUENCE: 46
tgttgaatgg aaaatattgg aagaatttca tttcatttta caaaaataaa gagtgtagag      60 ggtattttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctccctttc ccagaaatta agataattct ggtgcttttta gcattagaaa     360 agtatttatt gggtagggaa atgtcatgac ttcacagcat taagcatcaa gggtataact     420
taatgaaata gtggtcaatg aattatattg agaatgacga ggtctctgtt ccaactttgg     480
tagactttgg aaatgctcgt ctggacgccg cccattcttt ctagtcttgg tgccattcta     540
tttggtctga gactggcatg atgccaaatt ctaaccttt cacaatgagc attcgaccta     600
ctcttctttt ttacgactct atttgaccta ctaggcattg gccaacttgg ctaaccactt     660
gaggaactag agttcggatt caatagaatc taataatttt aatcaaaaga cttcatgtat     720
attgaaaaat ctatttataa ctaactttaa atcggccttt acgtatcgac gtaatcaaaa     780
ttgtgtcagc ttgccacgtg gggtctagta tgagtttgaa attggtcata ggggcccccaa     840 ttccactaat acagctgccg tccatgcact acaagacaaa tacaccacta tgtttgttag     900
tgcttggtaa atgtaaaaca aactttttgat gagaatctat tcgtggcatc gaagtgctgc     960
aaattggctt ttacctctgc tacttcaagc ctcactgatt ttcaccccaa ctttctcatt    1020
```

```
tcccttttcaa ggatttgatt ttccagttgg gcatgttaaa aacaacaatt ttcctcaaaa      1080
ctgtagaaat gatttctcat attttaatca gtcaaattat ttaaacaaga agttgatttt      1140
tttttaattt tttttttttac aaaaaaattt caaatgtcaa gtaagatttt tcaaattgaa      1200
actgaataag ctgcgacttt agaaacaaaa aactaagata agtaaaaata ccaaaaagag      1260
tgaatcacat caattgaatt cttccaacag ttcgttttttt agtttctgtt ttgggaagag      1320
gagtactaca aggtaggacc tccaacaatc aacaatatct aagttgcaaa agttttttgtg     1380 cgttttttag tttctgtttc gagaagagga atactacaag ttcgttttttt agtttctgtt     1440 ttgggaagag gagtactgca aggtaggacc tccaacaatt atcaatatct aaattgcaaa      1500
aatttcagtt cgttttttagt ttctgtttcg ggaagaggaa tactacaagt tcgttttttta    1560 gtttctatttt tgggaagagg agtactacaa ggtaggacct ccaataccta aattgcaaaa    1620
atttcagttc gttttttagt ttcagtttag ggaagaggaa tactacaagg taggacctcc      1680
aacaatcatc agtacctaaa ttgcaaaaat ttcagttcgt ttttttagttt atgtttggga     1740 agaagaatac tacaaggcag tggcggagct accttatgat taggggggttc atccgaacct    1800 ccttcgacgg aaaattatac tatttttata agtgaaaatt attttttatg tatatataat     1860
tgatgttgaa ccccccttcgg ttagttcatg tatctatatt ttttttatttt gaaccccgat   1920 gaaaattttg gctccgccac tgctacaagg taggacctcc aacaatcacc aatacctaaa     1980
ttgcaaaaat ttcagtttgt tttttagttt ctgttttggg aagaggaata ctacaaggta     2040
ggacctccaa caatcaccaa tacctaaatt gcaacgtttt tttagtttct gttttgggaa     2100
gaggaatact acatggtagg gcctccaaca atcaccaata cctaaattgc aaaaatttca     2160 gttcgtatttt tcgtttctat tttgggaagt ggaatagtat aaggtaggac ctccaacaat    2220
caccaatacc taaattaaag ttccgattca ttttttttagtt tctgttttgg aaagagaaat   2280
actacaaggt agggcctaca acaatcacca gtacctaaat tgtaaaaatt tcagttcgtt    2340 ttttagttttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata taattgat gttgaaccccc cttcggttag tttgtgtatc tatattttttt    2700 tattttgaac ctccttgata aaaattttg actccgccat tgctacaagg tagaacctcc      2760
aacaatcacc aatacctaaa ttgcaaaaat ttcagttcgt ttttttaattt ctgttttggg    2820 aagaggaata ctacaaggcc tccaacaatc accaatacct aaattgcaaa aatttcagtt     2880 tgttttttttag tttctgtttt gggaagagga atactacaag gtaaggcctc caacaatcac   2940
caatacctaa attgcaaaaa tttcagttcg tattttttcgtt tctattttgg gaagtggaat   3000
agtataaggt aggacctcca acaatcacca atacctaaat tgcaaaagtt ccgattcatt     3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt     3240
agtttctgtt ttgaaagag aaatactaca agataggacc ttcaacaatc accaatacct      3300
aaattgcaaa aacttcagtt cattttttag tttctgtttt gggaagaaga atacttcaag    3360
```

-continued

```
gtaacaatca ccaataccta aattaaattt cagttagttt tttagtttct gttttggga      3420 agaggaatac tttcttttgc tatataaagc caaagtaggt acctataagc atcaatattt     3480
tgtattgctt agtgattccc ctagttcggt atttcatttt ttttcactat actatatcac    3540
ctcctctcat aaatagccat tataaatctt gcattttctc taatgaaaac ccttctaaag    3600
ccttttccat ctcctttact ttccattcct actcctaaca tgtatagttt caaacacaac    3660
tccacttttc caaatccaac caaacaaaaa gattcaagaa agttccatta tagaaacaaa    3720
agcagtacac attttttgtag cttctcttgat ttagcaccca catcaaagcc agagtcttta  3780
gatgttaaca tctcatgggt tgatactgat ctggacgggg ctgaattcga cgtgatcatc   3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga   4080
aagaagttga agttgaaatt gttgaatagt tgtgttgaaa atagagtgaa gttttataaa   4140
gccaaggttt tgaaagtgaa gcatgaagaa tttgagtctt cgattgtttg tgatgatggt   4200
aggaagataa gcggtagctt gattgttgat gcaagtggct atgctagtga ttttatagag   4260
tatgacaagc caagaaacca tggttatcaa gttgctcatg ggattttagc agaagttgat   4320
aatcatccat ttgatttgga taaaatgatg cttatggatt ggagggattc tcatttaggt   4380
aatgagccat atctgagggt gaagaatact aaagaaccaa cattcttgta tgcaatgcca  4440
tttgatagga atttggtatt cttggaagag acttctttag tgagtcggcc tatgttatcg   4500
tatatggaag tgaaaagaag gatggtagca agattaagac atttggggat caaagtgaga  4560
agtgtccttg aggaagagaa gtgtgtgatc actatgggag gaccacttcc gcggattcct   4620
caaaatgtta tggctattgg tgggacttca gggatagttc atccatcgtc tgggtacatg   4680
gtggctcgta gcatggcatt ggcaccagta ctggctgagg ccatcgtcga aagccttggc  4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg   4920
cacgggttcc tttcttcaag attgtctgtc aaagaacttg ctgtactcag tttgtacctt    4980
tttggacatg cctctaattt ggctaggttg gatattgtta caaagtgcac tgtcccctgg  5040
gttaaactgc tgggcaatct agcaatagag agcctttgaa ttaatatgat agttttgaag   5100
cactgctttc attttaatt cttaggttat tttcatcttt tatcaatgca aaagtgaaac    5160
aaaagctata cacattgtca tcgttgttca aactcagaca agtttgccta gctctatgta    5220
tttatcctta acatatgtat tcatcaaatt cgaaatatac aatgtatggt tgtcgatgca   5280
ttggacaaaa gtatagagcc acaatctgat accaagtctg tatttggaag cactggctaa   5340
ttgttatggt taccaaacac tttgaattgg ctggataata acaggaaatt tatgttatta   5400
atcattaaca gcaaatttggg aaagcaagaa ttattaggaa agttaatata gtgtcttggt   5460
tattctaatg gagtgggtta tgcaaattaa gttccttat caaagtttgg tttatgaact    5520
gctccactcg tgtccctctt aaaagcctta atcccaacat gtaccaccaa agaactgagc    5580
tgctccatca gatccttga gaatgttaat atgttattta aatgaaggac tgaatgatta    5640
tgaggatgca atgcataggt ttaattacca gttatctgta aattgtcttc gttgccatta    5700
ttttaaaagt ttaataagtg taacatctac aaagagttga taa                    5743
```

<210> SEQ ID NO 47
<211> LENGTH: 1316
<212> TYPE: DNA
<213> ORGANISM: Capsicum annuum

<400> SEQUENCE: 47

| | | | | | |
|---|---|---|---|---|---|
| tgttgaatgg | aaaatattgg | aagaatttca | tttcatttta | caaaaataaa | gagtgtagag | 60 |
| ggtattttg | taaatcaata | tttttctat | aaaaaatata | taagaaatat | tattttaata | 120 |
| catcaaatca | aatactgtat | aagaaataat | gttaacataa | ttaatgcaag | tatagctaat | 180 |
| accaacatta | ctaatgcaag | tattactaat | acaccatatt | ctatattaat | cttatatact | 240 |
| ctaccaaacg | accctaagtg | tgtatctata | tcctccgaga | atttggaatt | tgcaaattcc | 300 |
| aagttttgta | tctcccttc | ccagaaatta | agataattct | ggtgctttta | gagtttggaa | 360 |
| tggtttgtgg | ccttcggata | aagacgtgt | tagagaatgt | tattgtttcg | gaatggagac | 420 |
| tttgttgaag | cttgatttgg | aaggtactag | gagattgttt | gatgctttct | ttgatgttga | 480 |
| tcccaagtac | tggcacgggt | tccttttcttc | aagattgtct | gtcaaagaac | ttgctgtact | 540 |
| cagtttgtac | cttttggac | atgcctctaa | tttggctagg | ttggatattg | ttacaaagtg | 600 |
| cactgtcccc | ttggttaaac | tgctgggcaa | tctagcaata | gagagccttt | gaattaatat | 660 |
| gatagttttg | aagcactgct | ttcattttaa | tttcttaggt | tattttcatc | ttttatcaat | 720 |
| gcaaaagtga | aacaaaagct | atacacattg | tcatcgttgt | tcaaactcag | acaagtttgc | 780 |
| ctagctctat | gtatttatcc | ttaacatatg | tattcatcaa | attcgaaata | tacaatgtat | 840 |
| ggttgtcgat | gcattggaca | aaagtataga | gccacaatct | gataccaagt | ctgtatttgg | 900 |
| aagcactggc | taattgttat | ggttaccaaa | cactttgaat | tggctggata | ataacaggaa | 960 |
| atttatgtta | ttaatcatta | acagcaaatt | gggaaagcaa | gaattattag | gaaagttaat | 1020 |
| atagtgtctt | ggttattcta | atggagtggg | ttatgcaaat | taagttccct | tatcaaagtt | 1080 |
| tggtttatga | actgctccac | tcgtgtccct | cttaaaagcc | ttaatcccaa | catgtaccac | 1140 |
| caaagaactg | agctgctcca | tcagatcctt | tgagaatgtt | aatatgttat | ttaaatgaag | 1200 |
| gactgaatga | ttatgaggat | gcaatgcata | ggtttaatta | ccagttatct | gtaaattgtc | 1260 |
| ttcgttgcca | ttatttttaaa | agtttaataa | gtgtaacatc | tacaaagagt | tgataa | 1316 |

<210> SEQ ID NO 48
<211> LENGTH: 1316
<212> TYPE: DNA
<213> ORGANISM: Capsicum annuum

<400> SEQUENCE: 48

| | | | | | |
|---|---|---|---|---|---|
| tgttgaatgg | aaaatattgg | aagaatttca | tttcatttta | caaaaataaa | gagtgtagag | 60 |
| ggtattttg | taaatcaata | tttttctat | aaaaaatata | taagaaatat | tattttaata | 120 |
| catcaaatca | aatactgtat | aagaaataat | gttaacataa | ttaatgcaag | tatagctaat | 180 |
| accaacatta | ctaatgcaag | tattactaat | acaccatatt | ctatattaat | cttatatact | 240 |
| ctaccaaacg | accctaagtg | tgtatctata | tcctccgaga | atttggaatt | tgcaaattcc | 300 |
| aagttttgta | tctcccttc | ccagaaatta | agataattct | ggtgctttta | gagtttggaa | 360 |
| tggtttgtgg | ccttcggata | aagacgtgt | tagagaatgt | tattgtttcg | gaatggagac | 420 |
| tttgttgaag | cttgatttgg | aaggtactag | gagattgttt | gatgctttct | ttgatgttga | 480 |
| tcccaagtac | tggcacgggt | tccttttcttc | aagattgtct | gtcaaagaac | ttgctgtact | 540 |

-continued

```
cagtttgtac cttttggac atgcctctaa tttggctagg ttggatattg ttacaaagtg      600
cactgtcccc ttggttaaac tgctgggcaa tctagcaata gagagccttt gaattaatat      660
gatagttttg aagcactgct ttcattttaa tttcttaggt tattttcatc ttttatcaat      720
gcaaaagtga aacaaaagct atacacattg tcatcgttgt tcaaactcag acaagtttgc      780
ctagctctat gtatttatcc ttaacatatg tattcatcaa attcgaaata tacaatgtat      840
ggttgtcgat gcattggaca aaagtataga gccacaatct gataccaagt ctgtatttgg      900
aagcactggc taattgttat ggttaccaaa cactttgaat tggctggata ataacaggaa      960
atttatgtta ttaatcatta acagcaaatt gggaaagcaa gaattattag gaaagttaat     1020
atagtgtctt ggttattcta atggagtggg ttatgcaaat taagttccct tatcaaagtt     1080
tggtttatga actgctccac tcgtgtccct cttaaaagcc ttaatcccaa catgtaccac     1140
caaagaactg agctgctcca tcagatcctt tgagaatgtt aatatgttat ttaaatgaag     1200
gactgaatga ttatgaggat gcaatgcata ggtttaatta ccagttatct gtaaattgtc     1260
ttcgttgcca ttatttaaa agtttaataa gtgtaacatc tacaaagagt tgataa         1316
```

<210> SEQ ID NO 49
<211> LENGTH: 1316
<212> TYPE: DNA
<213> ORGANISM: Capsicum annuum

<400> SEQUENCE: 49

```
tgttgaatgg aaaatattgg aagaatttca tttcatttta caaaaataaa gagtgtagag       60 ggtattttg taaatcaata ttttttctat aaaaaatata taagaaatat tattttaata      120
catcaaatca aatactgtat aagaaataat gttaacataa ttaatgcaag tatagctaat      180
accaacatta ctaatgcaag tattactaat acaccatatt ctatattaat cttatatact      240
ctaccaaacg accctaagtg tgtatctata tcctccgaga atttggaatt gcaaattcc       300 aagttttgta tctcccttttc ccagaaatta agataattct ggtgcttta gagtttggaa      360 tggtttgtgg ccttcggata gaagacgtgt tagagaatgt tattgtttcg gaatggagac      420
tttgttgaag cttgatttgg aaggtactag gagattgttt gatgcttct ttgatgttga      480 tcccaagtac tggcacgggt tccttttcttc aagattgtct gtcaaagaac ttgctgtact      540
cagtttgtac cttttggac atgcctctaa tttggctagg ttggatattg ttacaaagtg      600
cactgtcccc ttggttaaac tgctgggcaa tctagcaata gagagccttt gaattaatat      660
gatagttttg aagcactgct ttcattttaa tttcttaggt tattttcatc ttttatcaat      720
gcaaaagtga aacaaaagct atacacattg tcatcgttgt tcaaactcag acaagtttgc      780
ctagctctat gtatttatcc ttaacatatg tattcatcaa attcgaaata tacaatgtat      840
ggttgtcgat gcattggaca aaagtataga gccacaatct gataccaagt ctgtatttgg      900
aagcactggc taattgttat ggttaccaaa cactttgaat tggctggata ataacaggaa      960
atttatgtta ttaatcatta acagcaaatt gggaaagcaa gaattattag gaaagttaat     1020
atagtgtctt ggttattcta atggagtggg ttatgcaaat taagttccct tatcaaagtt     1080
tggtttatga actgctccac tcgtgtccct cttaaaagcc ttaatcccaa catgtaccac     1140
caaagaactg agctgctcca tcagatcctt tgagaatgtt aatatgttat ttaaatgaag     1200
gactgaatga ttatgaggat gcaatgcata ggtttaatta ccagttatct gtaaattgtc     1260
ttcgttgcca ttatttaaa agtttaataa gtgtaacatc tacaaagagt tgataa         1316
```

-continued

```
<210> SEQ ID NO 50
<211> LENGTH: 1316
<212> TYPE: DNA
<213> ORGANISM: Capsicum annuum

<400> SEQUENCE: 50
tgttgaatgg aaatatattgg aagaatttca tttcatttta caaaaataaa gagtgtagag        60 ggtattttg taaatcaata ttttttctat aaaaaatata taagaaatat tattttaata        120
catcaaatca aatactgtat aagaaataat gttaacataa ttaatgcaag tatagctaat        180
accaacatta ctaatgcaag tattactaat acaccatatt ctatattaat cttatatact        240
ctaccaaacg accctaagtg tgtatctata tcctccgaga atttggaatt tgcaaattcc        300
aagttttgta tctccctttc ccagaaatta agataattct ggtgctttta gagtttggaa        360
tggtttgtgg ccttcggata gaagacgtgt tagagaatgt tattgtttcg gaatggagac        420
tttgttgaag cttgatttgg aaggtactag gagattgttt gatgctttct ttgatgttga        480
tcccaagtac tggcacgggt tcctttcttc aagattgtct gtcaaagaac ttgctgtact        540
cagtttgtac ctttttggac atgcctctaa tttggctagg ttggatattg ttacaaagtg        600
cactgtcccc ttggttaaac tgctgggcaa tctagcaata gagagccttt gaattaatat        660
gatagttttg aagcactgct ttcattttaa tttcttaggt tattttcatc ttttatcaat        720
gcaaaagtga acaaaagct atacacattg tcatcgttgt tcaaactcag acaagtttgc        780
ctagctctat gtatttatcc ttaacatatg tattcatcaa attcgaaata tacaatgtat        840
ggttgtcgat gcattggaca aaagtataga gccacaatct gataccaagt ctgtatttgg        900
aagcactggc taattgttat ggttaccaaa cactttgaat tggctggata ataacaggaa        960
ctttatgtta ttaatcatta acagcaaatt gggaaagcaa gaattattag gaaagttaat       1020
atagtgtctt ggttattcta atggagtggg ttatgcaaat taagttccct tatcaaagtt       1080
tggtttatga actgctccac tcgtgtccct cttaaaagcc ttaatcccaa catgtaccac       1140
caaagaactg agctgctcca tcagatcctt tgagaatgtt aatatgttat ttaaatgaag       1200
gactgaatga ttatgaggat gcaatgcata ggtttaatta ccagttatct gtaaattgtc       1260
ttcgttgcca ttatttaaaa agtttaataa gtgtaacatc tacaaagagt tgataa          1316

<210> SEQ ID NO 51
<211> LENGTH: 1316
<212> TYPE: DNA
<213> ORGANISM: Capsicum annuum

<400> SEQUENCE: 51
tgttgaatgg aaatatattgg aagaatttca tttcatttta caaaaataaa gagtgtagag        60 ggtattttg taaatcaata ttttttctat aaaaaatata taagaaatat tattttaata        120
catcaaatca aatactgtat aagaaataat gttaacataa ttaatgcaag tatagctaat        180
accaacatta ctaatgcaag tattactaat acaccatatt ctatattaat cttatatact        240
ctaccaaacg accctaagtg tgtatctata tcctccgaga atttggaatt tgcaaattcc        300
aagttttgta tctccctttc ccagaaatta agataattct ggtgctttta gagtttggaa        360
tggtttgtgg ccttcggata gaagacgtgt tagagaatgt tattgtttcg gaatggagac        420
tttgttgaag cttgatttgg aaggtactag gagattgttt gatgctttct ttgatgttga        480
tcccaagtac tggcacgggt tcctttcttc aagattgtct gtcaaagaac ttgctgtact        540
cagtttgtac ctttttggac atgcctctaa tttggctagg ttggatattg ttacaaagtg        600
```

| | |
|---|---|
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga aacaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 52
<211> LENGTH: 1316
<212> TYPE: DNA
<213> ORGANISM: Capsicum annuum

<400> SEQUENCE: 52

| | |
|---|---|
| tgttgaatgg aaatattgg aagaatttca tttcattttta caaaaataaa gagtgtagag | 60 |
| ggtattttttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttttc ccagaaatta agataattct ggtgcttttta gagtttggaa | 360 |
| tggtttgtgg ccttcggata gaagacgtgt tagagaatgt tattgtttcg gaatggagac | 420 |
| tttgttgaag cttgatttgg aaggtactag gagattgttt gatgcttttct ttgatgttga | 480 |
| tcccaagtac tggcacgggt tccttttcttc aagattgtct gtcaaagaac ttgctgtact | 540 |
| cagtttgtac cttttttggac atgcctctaa tttggctagg ttggatattg ttacaaagtg | 600 |
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga aacaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 53
<211> LENGTH: 1316

<212> TYPE: DNA
<213> ORGANISM: Capsicum annuum

<400> SEQUENCE: 53

```
tgttgaatgg aaatattgg aagaatttca tttcatttta caaaaataaa gagtgtagag      60
ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgcttta gagtttggaa    360
tggtttgtgg ccttcggata aagacgtgt tagagaatgt tattgtttcg gaatggagac    420
tttgttgaag cttgatttgg aaggtactag gagattgttt gatgctttct ttgatgttga    480
tcccaagtac tggcacgggt tccttcttc aagattgtct gtcaaagaac ttgctgtact    540
cagtttgtac cttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcattttaa tttcttaggt tattttcatc ttttatcaat    720
gcaaaagtga acaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata taacaggaa    960
atttatgtta ttaatcatta acagcaaatt gggaaagcaa gaattattag gaaagttaat   1020
atagtgtctt ggttattcta atggagtggg ttatgcaaat taagttccct tatcaaagtt   1080
tggtttatga actgctccac tcgtgtccct cttaaaagcc ttaatcccaa catgtaccac   1140
caaagaactg agctgctcca tcagatcctt tgagaatgtt aatatgttat ttaaatgaag   1200
gactgaatga ttatgaggat gcaatgcata ggtttaatta ccagttatct gtaaattgtc   1260
ttcgttgcca ttattttaaa agtttaataa gtgtaacatc tacaaagagt tgataa       1316
```

<210> SEQ ID NO 54
<211> LENGTH: 5760
<212> TYPE: DNA
<213> ORGANISM: Capsicum annuum

<400> SEQUENCE: 54

```
tgttgaatgg aaatattgg aagaatttca tttcatttta caaaaataaa gagtgtagag      60
ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgcttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga aatggcatg atgccaaatt ctaccttttc acaatgagca ttcgacctac    600
tcttcttttt tcgactcatt tgacctacta ggcattggcc aacttggcta accacttgag    660
```

```
gaactagagt tcggattcaa tagaatctaa taatttaat caaaagactt catgtatatt      720
gaaaaatcta tttataacta actttaaatc ggcctttacg tatcgacgta atcaaaattg      780
tgtcagcttg ccacgtgggg tctagtatga gtttgaaatt ggtcataggg gccccaattc      840
cactaataca gctgccgtcc atgcactaca agacaaatac accactatgt ttgttagtgc      900
ttggtaaatg taaaacaaac ttttgatgag aatctattcg tggcatcgaa gtgctgcaaa      960
ttggctttta cctctgctac ttcaagcctc actgattttc accccaactt tctcatttcc     1020
ctttcaagga tttgatttc cagttgggca tgttaaaaac aacaatttc ctcaaaactg      1080 tagaaatgat ttctcatatt ttaatcagtc aaattattta acaagaagt tgatttttt       1140 ttaatttttt tttttacaaa aaaatttcaa atgtcaagta agattttca aattgaaact      1200 gaataagctg cgactttaga aacaaaaaac taagataagt aaaaatacca aaagagtga       1260 atcacatcaa ttgaattctt ccaacagttc gttttttagt ttctgttttg ggaagaggag     1320
tactacaagg taggacctcc aacaatcaac aatatctaag ttgcaaaagt ttttgtgcgt     1380
tttttagttt ctgtttcgag aagaggaata ctacaagttc gttttttagt ttctgtttg      1440 ggaagaggag tactgcaagg taggacctcc aacaattatc aatatctaaa ttgcaaaaat     1500
ttcagttcgt ttttagtttc tgtttcggga agaggaatac tacaagttcg ttttttagtt     1560
tctattttgg gaagaggagt actacaaggt aggacctcca atacctaaat tgcaaaaatt     1620
tcagttcgtt ttttagtttc agtttaggga agaggaatac tacaaggtag gacctccaac     1680
aatcatcagt acctaaattg caaaaatttc agttcgtttt ttagtttatg ttttgggaag     1740
aagaatacta caaggcagtg gcggagctac cttatgatta gggggttcat ccgaacctcc     1800
ttcgacggaa aattatacta ttttataag tgaaaattat tttttatgta tatataattg      1860
atgttgaacc cccttcggtt agttcatgta tctatatttt tttattttga accccgatga     1920
aaattttggc tccgccactg ctacaaggta ggacctccaa caatcaccaa tacctaaatt     1980
gcaaaaattt cagtttgttt tttagtttct gttttgggaa gaggaatact acaaggtagg     2040
acctccaaca atcaccaata cctaaattgc aacgttttt agtttctgtt ttgggaagag      2100
gaatactaca tggtagggcc tccaacaatc accaatacct aaattgcaaa aatttcagtt     2160 cgtatttcg tttctatttt gggaagtgga atagtataag gtaggacctc caacaatcac      2220
caatacctaa attaaagttc cgattcattt tttagtttct gttttgggaa gagaaatact     2280
acaaggtagg gcctacaaca atcaccagta cctaaattgt aaaaatttca gttcgttttt     2340
tagtttctat tttgagaaga ggaatgctac aaggtagggc ctacaacaat caccagtacc     2400
taaattgtaa aaatttcagt tcgttttta gtttctgttt tgggaagagg aatactacaa      2460
ggtagggcct tcaacaatca gcaataccta aattacaaaa atttcaattc gttttttagt     2520
ttctgttttg ggaagaggaa tactacaagg cagtggcgga gctaccttat gattaggggt     2580
tcatccgaac ctccttcgac ggaaaattat actattttta tatagtaaaa attattttt      2640 atgtatatat aattgatgtt gaacccccctt cggttagttt gtgtatctat attttttta     2700 tttgaacctc cttgataaaa aattttgact ccgccattgc tacaaggtag aacctccaac     2760
aatcaccaat acctaaattg caaaaatttc agttcgtttt ttaatttctg ttttgggaag     2820
aggaatacta caaggcctcc aacaatcacc aatacctaaa ttgcaaaaat ttcagtttgt     2880 ttttagttt ctgttttggg aagaggaata ctacaaggta aggcctccaa caatcaccaa     2940
tacctaaatt gcaaaaattt cagttcgtat tttcgtttct atttgggaa gtggaatagt      3000 ataaggtagg acctccaaca atcaccaata cctaaattgc aaaagttccg attcatttt      3060
```

```
tagtttctgt tttggaaaga gaaatactac aaggtagggt ctccaacaat caccagtacc    3120
taaattgtaa aaatttcagt tcgttttta gtttctattt tgggaagtgg aatagtataa     3180
ggtaggacct ccaacaatca ccaataccta aattgcaaaa gttccgattc ttttttagt     3240
ttctgttttg gaaagagaaa tactacaagg taggaccttc aacaatcacc aatacctaaa    3300
ttgcaaaaac ttcagttcat tttttagttt ctgttttggg aagaagaata cttcaaggta    3360
acaatcacca atacctaaat taaaaatttc agttagtttt ttagtttctg tttttgggaa    3420
gaggaatact ttcttttgct atataaagcc aaagtaggta cctataagca tcaatatttt    3480
gtattgctta gtgattcccc tagttcggta tttcattttt tttcactata ctatatcacc    3540
tcctctcata aatagccatt ataaatcttg cattttctct aatggaaacc cttctaaagc    3600
cttttccatc tccttactt tccattccta ctcctaacat gtatagtttc aaacacaact     3660
ccacttttcc aaatccaacc aaacaaaaag attcaagaaa gttccattat agaaacaaaa    3720
gcagtacaca ttttgtagc tttcttgatt tagcacccac atcaaagcca gagtctttag     3780
atgttaacat ctcatggggt gatactgatc tggaccgggc tgaattcgac gtgatcatca    3840
ttggaactgg ccctgccggg cttcggctag ctgaacaagt ttctaaatat ggtattaagg    3900
tatgttgcgt tgacccttca ccactttcca tgtggccaaa taattatggt gtttgggttg    3960
atgagtttga aaagtggga ttagaagatt gtctagatca taagtggcct gtgagttgtg     4020
ttcatataag tgatcacaag actaagtatt tggacagacc atatggtaga gtaagtagaa    4080
agaagttgaa gttgaaattg ttgaatagtt gtgttgaaaa tagagtgaag ttttataaag    4140
ccaaggtttt gaaagtgaag catgaagaat ttgagtcttc gattgtttgt gatgatggta    4200
ggaagataag tggtagcttg attgttgatg caagtggcta tgctagtgat tttatagagt    4260
atgacaagcc aagaaaccat ggttatcaag ttgctcatgg gattttagca gaagttgata    4320
atcatccatt tgatttggat aaaatgatgc ttatggattg gagggattct catttaggta    4380
atgagccata tctgagggtg aagaatacta aagaaccaac attcttgtat gcaatgccat    4440
ttgataggaa tttggtattc ttggaagaga cttcttttagt gagtcggcct atgttatcgt    4500
atatggaagt gaaaagaagg atggtagcaa gattaagaca tttggggatc aaagtgagaa    4560
gtgtccttga ggaagagaag tgtgtgatca ctatgggagg accacttccg cggattcctc    4620
aaaatgttat ggctattggt gggacttcag ggatagttca tccatcgtct gggtacatgg    4680
tggctcgtag catggcattg gcaccagtac tggctgaggc catcgtcgaa agccttggct    4740
caacaagaat gataagaggg tctcaacttt accatagagt ttggaatggt ttgtggcctt    4800
cggatagaag acgtgttaga gaatgttatt gtttcggaat ggagactttg ttgaagcttg    4860
atttggaagg tactaggaga ttgtttgatg cttctcttga tgttgatccc aagtactggc    4920
acgggttcct ttcttcaaga ttgtctgtca agaacttgc tgtactcagt ttgtacctt      4980
ttggacatgc ctctaatttg gctaggttgg atattgttac aaagtgcact gtccccttgg    5040
ttaaactgct gggcaatcta gcaatagaga gcctttgaat aatatgata gttttgaagc     5100
actgttttca ttttaatttc ttaggttatt ttcatctttt ctcaatgcaa aagtgaaaca    5160
aaagctatac acattgtcat cgttgttcaa actcagacaa gtttgcctag ctctatgtat    5220
ttatccttaa catatgtatt catcaaattc gaaatataca atgcattgga caaaagtata    5280
gagccacaat ctgataccaa gtctgtattt ggaagcacag gctaattgtt atggttacca    5340
aacactttga attggctgga taataacaaa caggaaattt atgttattaa tcattaacag    5400
```

-continued

```
caaattggga aagcaagaat tattaggaaa gttaatatag tgtcttggtt attctaatgg    5460
agtgggttat gcaaattaag ttccttgtc aaagtttggt ttatgaactg ctccactctt     5520
gtccctctta aaagccttaa tcccaacatg taccaccaaa gaattgagct gctccatcag    5580
atcctttgag aatgttaata tgttatttaa atgaaggact gaatgattat gaggatgcaa    5640
tgcataggtt taattaccag ttatctgtaa attgtcttct ttgccattat tttaaaagtt    5700
taataacaag tgtaacatct acaaagagtt gataattaca aagcagctac tagttttagg    5760
```

<210> SEQ ID NO 55
<211> LENGTH: 498
<212> TYPE: PRT
<213> ORGANISM: Capsicum annuum

<400> SEQUENCE: 55

```
Met Glu Thr Leu Leu Lys Pro Phe Pro Ser Pro Leu Leu Ser Ile Pro
1               5                   10                  15

Thr Pro Asn Met Tyr Ser Phe Lys His Asn Ser Thr Phe Pro Asn Pro
            20                  25                  30

Thr Lys Gln Lys Asp Ser Arg Lys Phe His Tyr Arg Asn Lys Ser Ser
        35                  40                  45

Thr His Phe Cys Ser Phe Leu Asp Leu Ala Pro Thr Ser Lys Pro Glu
    50                  55                  60

Ser Leu Asp Val Asn Ile Ser Trp Val Asp Thr Asp Leu Asp Gly Ala
65                  70                  75                  80

Glu Phe Asp Val Ile Ile Ile Gly Thr Gly Pro Ala Gly Leu Arg Leu
                85                  90                  95

Ala Glu Gln Val Ser Lys Tyr Gly Ile Lys Val Cys Cys Val Asp Pro
            100                 105                 110

Ser Pro Leu Ser Met Trp Pro Asn Asn Tyr Gly Val Trp Val Asp Glu
        115                 120                 125

Phe Glu Lys Leu Gly Leu Glu Asp Cys Leu Asp His Lys Trp Pro Val
    130                 135                 140

Ser Cys Val His Ile Ser Asp His Lys Thr Lys Tyr Leu Asp Arg Pro
145                 150                 155                 160

Tyr Gly Arg Val Ser Arg Lys Lys Leu Lys Leu Lys Leu Leu Asn Ser
                165                 170                 175

Cys Val Glu Asn Arg Val Lys Phe Tyr Lys Ala Lys Val Leu Lys Val
            180                 185                 190

Lys His Glu Glu Phe Glu Ser Ser Ile Val Cys Asp Asp Gly Arg Lys
        195                 200                 205

Ile Ser Gly Ser Leu Ile Val Asp Ala Ser Gly Tyr Ala Ser Asp Phe
    210                 215                 220

Ile Glu Tyr Asp Lys Pro Arg Asn His Gly Tyr Gln Val Ala His Gly
225                 230                 235                 240

Ile Leu Ala Glu Val Asp Asn His Pro Phe Asp Leu Asp Lys Met Met
                245                 250                 255

Leu Met Asp Trp Arg Asp Ser His Leu Gly Asn Glu Pro Tyr Leu Arg
            260                 265                 270

Val Lys Asn Thr Lys Glu Pro Thr Phe Leu Tyr Ala Met Pro Phe Asp
        275                 280                 285

Arg Asn Leu Val Phe Leu Glu Glu Thr Ser Leu Val Ser Arg Pro Met
    290                 295                 300

Leu Ser Tyr Met Glu Val Lys Arg Arg Met Val Ala Arg Leu Arg His
305                 310                 315                 320
```

Leu Gly Ile Lys Val Arg Ser Val Leu Glu Glu Lys Cys Val Ile
                325                 330                 335

Thr Met Gly Gly Pro Leu Pro Arg Ile Pro Gln Asn Val Met Ala Ile
            340                 345                 350

Gly Gly Thr Ser Gly Ile Val His Pro Ser Ser Gly Tyr Met Val Ala
        355                 360                 365

Arg Ser Met Ala Leu Ala Pro Val Leu Ala Glu Ala Ile Val Glu Ser
    370                 375                 380

Leu Gly Ser Thr Arg Met Ile Arg Gly Ser Gln Leu Tyr His Arg Val
385                 390                 395                 400

Trp Asn Gly Leu Trp Pro Ser Asp Arg Arg Val Arg Glu Cys Tyr
                405                 410                 415

Cys Phe Gly Met Glu Thr Leu Leu Lys Leu Asp Leu Glu Gly Thr Arg
                420                 425                 430

Arg Leu Phe Asp Ala Phe Phe Asp Val Asp Pro Lys Tyr Trp His Gly
            435                 440                 445

Phe Leu Ser Ser Arg Leu Ser Val Lys Glu Leu Ala Val Leu Ser Leu
        450                 455                 460

Tyr Leu Phe Gly His Ala Ser Asn Leu Ala Arg Leu Asp Ile Val Thr
465                 470                 475                 480

Lys Cys Thr Val Pro Leu Val Lys Leu Leu Gly Asn Leu Ala Ile Glu
                485                 490                 495

Ser Leu

<210> SEQ ID NO 56
<211> LENGTH: 1983
<212> TYPE: DNA
<213> ORGANISM: Capsicum annuum

<400> SEQUENCE: 56

```
atgtatgcat cgtctgccag ggacggtatc ccggggaaat ggtgtaacgc tcgccgtaag      60
cagctacctt tattgatatc caaggacttt cctgcagagt tgtatcattc tttaccttgt     120
aagagtttgg aaaatgggca tatcaagaag gttaaggagt aaaagccac actagctgaa      180
gctccagcta ctcctacaga gaagagtaac tctgaggttc acagaagaa gttgaaagta     240
cttgtggcag gtggtgggat tggaggatta gttttgtctt ggcaggaaa gaagaggggg     300
tttgatgtgt tagtgtttga gagagatata agtgctataa gaggtgaggg gcaatataga     360
ggtccaattc agatacagag caatgcattg gctgctttgg aagcaattga tatggatgtt     420
gctgaagaga tcatgaatgc tggctgtatc actggtcaaa ggattaatgg cttggtcgat     480
ggtatttctg gcaactggta ttgcaagttt gatacgttca ctccagctgt ggaacgtgga     540
cttcctgtga caagagtcat cagccgcatg actttgcaac agattcttgc acgtctgcag     600
ggggaggatg taattatgaa tgaaagccat gtagtaaatt ttgcggatga tgggagacg      660
gttactgtga atcctgagtt atgccaacaa tacacaggtg atcttctggt tggtgctgat     720
ggcataaggt ctaaggtacg gactaatttg ttcggaccga gtgaactaac ttactctggt     780
tacacttgtt atactggaat tgcagatttc gtccctgctg atattgacac agctggctac     840
cgagtctttt tgggccacaa acagtacttt gtttcttcag atgtgggtgg aggcaagatg     900
cagtggtatg catttcacaa tgaaccagct ggtggtgtgg atgctccaaa cggtaaaaag     960
gaaagattgc ttaaaatatt tgggggatgg tgtgacaacg ttatagacct ttcagtcgcc    1020
acagatgaag atgcaattct tcgtcgtgac atctatgata gacccccaac atttagttgg    1080
```

```
ggaaaaggtc gtgttacatt gcttggggac tctgtccatg ctatgcagcc taatttgggt    1140
caaggaggat gcatggccat agaggatagc tatcaactag cactggaact tgagaaagca    1200
tggagccgaa gtgctgagtc cggaagccct atggatgtca tctcatcttt acggagctat    1260
gaaagtgcta gaaaactccg agttggagtt atccatggac tggctagaat ggctgcaatc    1320
atggcatcag cttacaaggc ctatcttggt gtcggactgg gtccattatc attcattacc    1380
aagtttagga taccacatcc tggaagagtt ggtggaagat ttttattga cttgggaatg    1440 ccgcttatgt aagctgggt tctaggaggc aacggggaaa agcttgaagg cagaatacaa     1500
cattgcagac tatctgagaa agcaaatgac caattgagaa attggtttga agatgatgat    1560
gctttagagc gtgctactga tgcagagtgg ctattgcttc ctgccgggaa tagcaatgct    1620
gctttagaaa ctctcgtttt aagcagagat gagaacatgc cttgcactat cgggtctgtc    1680
tcacatgcaa acattcctgg aaaatcagtt gttattcctt tgtctcaggt gtccgatatg    1740
cacgcccgga tatcctacaa tggtggcgca tttctcggca ctgctttccg aagtgaccat    1800
ggcacttggt ttatagataa cgaaggcaga agatatcggg tgtctccaaa cttcccaatg    1860
cggtttcatt catcagatgt aatcgtatt  ggttctgata aggcagcatt tcgtataaag    1920
gctatgaaat ttgccccaaa aactgctgca aagaagatc gtcaagcagt gggggcagct     1980
tag                                                                   1983
```

<210> SEQ ID NO 57
<211> LENGTH: 613
<212> TYPE: DNA
<213> ORGANISM: Capsicum annuum
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 57

```
ctgtagctcc acattgcttc ctacatagga cttgctcaga atagaactcg aaaagagna     60 ccaattgaat gtaaatactt caacaactta ggtagggaca tcttatattg ctaaatacag    120
tgcccactct gcacagacta ggcatacaaa gcattccggc ccatcttagt gaagaaacat    180
gatatttgtt cacgtccatt agtttgtttg tacccgtctt tagttgttat ctattcgtga    240
tatcaagaat ataagactg gtggcttat tcacgtaaat tgtagtcctt gcctcagtag      300
taaaattttg tttcytgtca atagaggtac agtctttaga ttcaacttcc tcccttgtcc    360
atgcagtttg tgcttcttct gatgttgcgt acaatgctgc caataatcgt cggtgttgct    420
ggagataact cggtaatatt ggtcatggtt agtgtcacag ttatatttcc tttgnaaatg    480
aaaattctgc ttttcctcg gttcatttat atgttcatct ttatagttat tagtgttgaa     540
agctattgga atcctactgg cagtctatgt tgtggtgaaa acttttattg ctgtacgaca    600
tcggaggcat cag                                                        613
```

<210> SEQ ID NO 58
<211> LENGTH: 2007
<212> TYPE: DNA
<213> ORGANISM: Capsicum annuum

<400> SEQUENCE: 58

```
gggatcgac attgatccaa ctgccaaaat tgtccttagg acagtaagga gtatgagaca      60
atccattaga tctagctcct ccttccctac atgcagatga ccctaaccag tggatcgata     120
aatttccttt aaccattggc taaaagtgag ttgagaaaaa ataaagaga aacctaattt     180 acttccctca gtgacccctt tgtcttccat gcttcaagta tgtgtaccct tgacatgttt     240
ctgctgctat ggttatcaga caatgcgacg atgcatttct gcatccgtgg tgtgttttct     300
tctgtgcctt tgacatcgt gtttcattt cctctttatg tttgctaaca gtttgatttt     360
aagaggcctt gctaaagaga tggatgtctt ctgtttctta cgagctatct ctgcttcttt     420
agcccttcaa gataccttaa cagtgcattt gttaatactc tcttgtagca ctagcagata     480
actactgcat ataccatttc tatttctctt cttcttgtta aagtaattgc cgtagttgta     540
ctactgatcg ttctagtctc ttgaaaatac tgctatcctg cctttcttg aatcattacc     600 ttttgaagaa ctcagcacat tttttcagtt tggtgtctct gaggcatgat taaccacttt     660
caataaaaat ttacatgcat atgacagaat gtgtatgcac tgactttgtt ggaacctaag     720
taaacagcaa ccatcttcat gcctttcttg accaaagaag ttgctgacac ggctttgaca     780
tctgcatgtt tgttatccac agttcagaag ttacagccta catcctctag acctcactca     840
ataatttagc aacttttcct tgcattatgt gtttacttcc atttgtttga tcatttactt     900
ggttaacatg tagaattgga gttgtatctg ggaaagctat atttgcacaa ccacttgatg     960
aatattggaa gaagaaactt caggagaaac cagccgcaaa agaaaatgat gtaagcacct    1020
catagcgttt ggtgatctga gcttaatatc gtagtatttt tctgttggcc gttactctat    1080
aaaaatgcct tgtgtatcca caccctcatc caaataacta attacatgat gctctagaaa    1140
tttcatcctt cagttgtttg tatgagactg cccatcaaaa ctatccacgt ttttaatctt    1200
gtcgcgaaat attacatatc aattgggata aaattgtgcc catgttactt tacgtttctt    1260
tgaagtattt ggatgaagta ttcatgtggt cagaaccaaa attgatcatt tagaaaggat    1320
gctgattact gaatgtaatg tcatcaagca taatttgttc cttttaattg gaattatctg    1380
tactcggcac tagtgtgtgt ccctttcctt ggttctgttg tgcactggct tggcgctaat    1440
ttagaacatc tgcattaaac gcctggacta aatgctgata tttaatgctg aaatgtgtgt    1500
aataatcaca attgacgctg ggtaatatag attttcatca gattataatc ttacagatga    1560
tctccatgag gtagggtcag tgggttaagg gttctctttt atagtgtaaa agttaattta    1620
ttcgtttagt tggttgcaga gcattacata gcttttaata ttctctttac ttaacagaac    1680
tatgatcact tcaactgagt gaagaaaagg aaaagaacca ctgacaggag acagagaaat    1740
tacgggcata attacattca ctcgacaaac atgaattgaa atacaatcaa tcaacaagga    1800
caaaccaatg atatacagyt gtactatcca agattcccctt ggcaaaagaa tgtaatactc    1860
taggaagttt aacaaataaa aagttgtctt cccaagattc taatcgaaac ttctaatttg    1920
gaaccaagat ccaaggacca ttaagtatgt gtaaacatag agagaggcat atactaacag    1980
tagtagaaga tttcccaccc acatacc                                          2007
```

<210> SEQ ID NO 59
<211> LENGTH: 336
<212> TYPE: DNA
<213> ORGANISM: Capsicum annuum

<400> SEQUENCE: 59

```
gtcaattctt tgtttcttgc agagctagta cttttttgtct tgttggacca atcccttac     60 aytggagggg gtccttgttt gctttctcct ctgaaaaatg tacgtattga ctgcaacatg    120
```

```
gtctacaagg aagaactttc ttttgcatat acaacaatag agacgttaat aaattctctt      180
tggaaaacta ctttattact gttctgatta ttcaatagct acttggatca ataatgatgt      240
aagagacaca atagcaatac taggtttagg gacttgtgtt atcttctctt tgttgcattc      300
agaatgaagg gacgattcta taactgctgt ctgtca                               336

<210> SEQ ID NO 60
<211> LENGTH: 963
<212> TYPE: DNA
<213> ORGANISM: Capsicum annuum

<400> SEQUENCE: 60
ggttttcttg tttgcatgcg ccattgctct tctagcttct tcatcaatgg tttctgctga       60
agttatcgag cattcttttc aagtatataa ctctcctctt tttatttcct atttatgcaa      120
attaggttct cctttttgc acccatctc gagaaaataa atatgaaatt acatatata        180 tatatataga ggtgtcaaaa aaaaagtttg tgttaataaa tgagtatgct attgactcac      240
ccaattgtta tttgagttga aatggattaa acgatgggtc ataacctaac tcttcttttt      300
ttgcaatttg tctaagtata gccctaagta atttttttt ctttgtcctg gttatacata       360
acatatcaaa tagaagttta tttctggaaa aaaagacatt ttaacaaggt aaatgttttg      420
tgaagacttt ccttttgatc caagggtcta gcggaagcaa cctttcaacc tcacaagagt      480
cggggtgaag tttgtataca tcccactccg tcagacctca ttgtggtatt acaatggata      540
agctattgtt gttgttgtaa atgttttgtg agtgataaga ttatgtattt ggttggtgta      600
ggtgcaaaac cttactataa acaggttatg ccgtagacaa gtaataaatg cagtaaatgg      660
aagtcttcct ggtccaactc tacatgtacg tgagggcgac accmttgttg ttcatgtctt      720 caataaaatta ccatacgatc tcactatcca ttggtatgtc attcacgtta atttaattaa     780
aggatttaac ttatatacat tgctagcgca tagaaatttt atactatcaa tgtttaatta     840
atcacaagag gttgttattt catttttaat atcaaaatta ataccatact aaagcgtaac     900
gtgtggttac cataagatct ccaatcaaat ctttctttct ttttcctatc aaatttcact     960
ttc                                                                    963

<210> SEQ ID NO 61
<211> LENGTH: 2014
<212> TYPE: DNA
<213> ORGANISM: Capsicum annuum

<400> SEQUENCE: 61
ggatgtaata aatcattttg ttttatctga ggaagtatga agaagagtaa tacttcaccc       60
aaaagcttca ttaataaaat tcagaaaggt aaacagtaac ttacagtatc aactggaatt      120
gaaaagccaa cacccgatga tgcaccggaa ggagaatata tagcagtatt tattccaata      180
aggtttccag aactatctag aagtggtcct ccactgttac cgggattgat tgctgcgtct      240
gtctgaataa catcttggat tggacggcca gtagctgcag aattgatttc tcttctaagg      300
ccactagaaa catataaatt aatcagttat attaaagaaa atgtatgata aatagcatat      360
actttataca wcaccaacac atcttgcttt tgcgtataat atatccattt actgcgagat      420
atggttattg catatgtaat acgtttgctt cttggatttt atggatgcaa ggctctagac      480
agtgacaacc aaccaatcta tcctataaca atctgctttc tgccatattt cagaaatgaa      540
aacaaaaggt ggaccttacg gaaagatgag gagtattgga cacacttgaa agatataatc      600
```

| | |
|---|---|
| tcccttttgtc gttcaaaaag caaagaaaag atagagatca agaaagccac caacattgaa | 660 |
| aaactcgtat ttcagttgaa atggatgaag aagattaatc aaaactctct acttcatctc | 720 |
| aattctaaac aaaggaaaga aggttacttc attttattt atttaatttc ctctcattta | 780 |
| cttccttcac tttgttagtc attaattcca caagccttct accaagattt tgagtgtccc | 840 |
| atattcattt tattttatct cctatcttca cacaacactg ttagcaccat ttcactggaa | 900 |
| tatctgaaca ttaggaactt gtgcacaata atatgaaata agtaaatacc tgataacacc | 960 |
| agtggtgagt gtatgatcaa gtccaaactg caacatattt acataaaaga ccagtcatca | 1020 |
| ggtgttttcca gatgaaaatt aaaagagaag taaaatatta atgtttcata gtaaattata | 1080 |
| cgaatacaga ggaaaaagag gcgtgaaggg gggaaggcta cccaaatata agaaacatgc | 1140 |
| acccatttca acaagagatc tagttccaat gtgtaagtca agtacgttga ttttaatgta | 1200 |
| agtcagtgcg aaattttggc agaagttgga gcactagatt aaaggaggga attgttatgc | 1260 |
| tctaaacttg ggggaaaaca agcagttaaa aatattagca ggctggtaaa ggttcagaag | 1320 |
| tagcagctaa ctttcagatg ggctaatggg caaagatttg aaacagaaga cagaaataag | 1380 |
| ttgtactctc tatcagttgt tttttttct tgcacaaatt ttcgtaataa gaaaaatgca | 1440 |
| ctagaaatct gtatgcaaag ttatactttc taactgttgt aatgctcatg aacgcctgca | 1500 |
| agccaaattg catagactct gcatttcgat gccgcacgcg tgtcggatgc tccaaaaata | 1560 |
| cacttctttt tatatttgga gaatccggca cgcacccact gacattttg aagagtccaa | 1620 |
| gcaacatagc ctgcaagaca attgttttct cgaaagcaag gactgaatat gaaatggacc | 1680 |
| aaactagttt agagaaggga caatagacca gactaaaagc gctatcatta aaaagggtag | 1740 |
| ctcggtgcac taaagctatt gctatgcgcg gtgtccggag aagggcccca ccacaagggt | 1800 |
| gtatcgtacg cagccttacc ttgcatttct gccagaggct gtttccaaga ctttaacccg | 1860 |
| tgacctcctg ataacatgac aacaacttta ccagttactc caaggctccc cttcaaaagt | 1920 |
| gctatcatta catgaataga attctctatc aggtttgtat ttcatcacat acaggatttc | 1980 |
| caatagcaaa tacttttga ccaacgagca agtc | 2014 |

<210> SEQ ID NO 62
<211> LENGTH: 1216
<212> TYPE: DNA
<213> ORGANISM: Capsicum annuum

<400> SEQUENCE: 62

| | |
|---|---|
| ccttagcttg cgtctctctt gatctcgatt cctctggtgc ttcttttgaa ttacattcca | 60 |
| attctttctc gttttttgtaa ttttcttgac ttttggcctc tgcacccagt tgcacatatg | 120 |
| gggtaatgct gtctttgggc gtaccattga cgccagtgct gcttgttgga acagtttcct | 180 |
| ccctctctaa tgtaagtaga ggatatgctg cttgatcttg tagctgctta gttgcattgc | 240 |
| tttcactgct caccatgtta tccattgcta tctccttttc cggaacctta acagatgtca | 300 |
| atgatgtcaa atgttctgtt atttcttctt gctcattcct tgttttttcc tcttgttcac | 360 |
| ctcctacttg ggtaattgga gcattttcag tctttaattc ttctttctgt gtttcttttg | 420 |
| tttcatcgca tgttatcatc tctccgaaac ctgctgctgt ttttctttct gatccaaaag | 480 |
| gttccaaact tcctctttca ggttcacttg ttgttgttcc ctgctcttgc tgtacctgtg | 540 |
| ttgtgytgtt gtttgaggaa tcttggccgg tgctctctct taagtcttct tcttgttcct | 600 |
| cctatgagtt catatcttac cgtcagaaat cttgattgaa ttgttgcgcg agtaaatagg | 660 |
| ggagacagag gggtgtatga aaagattgga ataatgtatt ttgcttctat ttttttagct | 720 |

| | | |
|---|---|---|
| tttttcctca ctgtttatag tctagatcca gttttataat tcagaattat gatttcttgt | 780 | |
| agcagattgc aaatcggcat ttatgttata ctctgcctgt gtatatgaaa tgtttcatgc | 840 | |
| agttgaccat gcataatgtt ttcacggcaa catcttttca atcccctctt tgcacgagaa | 900 | |
| tacaaaaact gaaataata tatagtcatc tagagatttg tgaccttaac taacttggag | 960 | |
| ttgtggctta gatgttgtca tcgttgttgt tctgaaatat tgtgcagcag gagaaccaaa | 1020 | |
| tttctaggtt cataaacatg caataaactc atagattctc agtagatgct aatcagctaa | 1080 | |
| cgttgtaagt tcttgttcat ttaccttgtt agtattgtcc tccaccctca tttcttctga | 1140 | |
| agaaagttca attgcgttct ccactccacg cacgtcttta acctcttctg tggttaggtt | 1200 | |
| ggcttttga aggttc | 1216 | |

```
<210> SEQ ID NO 63
<211> LENGTH: 25
<212> TYPE: DNA
<213> ORGANISM: Artificial sequence
<220> FEATURE:
<223> OTHER INFORMATION: primer

<400> SEQUENCE: 63
cgtaaattgt agtccttgcc tcagt                                           25

<210> SEQ ID NO 64
<211> LENGTH: 25
<212> TYPE: DNA
<213> ORGANISM: Artificial sequence
<220> FEATURE:
<223> OTHER INFORMATION: primer

<400> SEQUENCE: 64
ggacaaggga ggaagttgaa tctaa                                           25

<210> SEQ ID NO 65
<211> LENGTH: 19
<212> TYPE: DNA
<213> ORGANISM: Artificial sequence
<220> FEATURE:
<223> OTHER INFORMATION: Primer

<400> SEQUENCE: 65
ctctattgac aagaaacaa                                                  19

<210> SEQ ID NO 66
<211> LENGTH: 17
<212> TYPE: DNA
<213> ORGANISM: Artificial sequence
<220> FEATURE:
<223> OTHER INFORMATION: Primer

<400> SEQUENCE: 66
ctattgacag gaaacaa                                                    17

<210> SEQ ID NO 67
<211> LENGTH: 23
<212> TYPE: DNA
<213> ORGANISM: Artificial sequence
<220> FEATURE:
<223> OTHER INFORMATION: Primer

<400> SEQUENCE: 67
ctggtccaac tctacatgta cgt                                             23
```

<210> SEQ ID NO 68
<211> LENGTH: 29
<212> TYPE: DNA
<213> ORGANISM: Artificial sequence
<220> FEATURE:
<223> OTHER INFORMATION: Primer

<400> SEQUENCE: 68
ccaatggata gtgagatcgt atggtaatt                              29

<210> SEQ ID NO 69
<211> LENGTH: 16
<212> TYPE: DNA
<213> ORGANISM: Artificial sequence
<220> FEATURE:
<223> OTHER INFORMATION: Primer

<400> SEQUENCE: 69
agggcgacac cattgt                                            16

<210> SEQ ID NO 70
<211> LENGTH: 16
<212> TYPE: DNA
<213> ORGANISM: Artificial sequence
<220> FEATURE:
<223> OTHER INFORMATION: Primer

<400> SEQUENCE: 70
agggcgacac ccttgt                                            16

<210> SEQ ID NO 71
<211> LENGTH: 28
<212> TYPE: DNA
<213> ORGANISM: Artificial sequence
<220> FEATURE:
<223> OTHER INFORMATION: Primer

<400> SEQUENCE: 71
caatcaatca acaaggacaa accaatga                               28

<210> SEQ ID NO 72
<211> LENGTH: 29
<212> TYPE: DNA
<213> ORGANISM: Artificial sequence
<220> FEATURE:
<223> OTHER INFORMATION: Primer

<400> SEQUENCE: 72
ctagagtatt acattctttt gccaaggga                              29

<210> SEQ ID NO 73
<211> LENGTH: 22
<212> TYPE: DNA
<213> ORGANISM: Artificial sequence
<220> FEATURE:
<223> OTHER INFORMATION: Primer

<400> SEQUENCE: 73
atcttggata gtacagctgt at                                     22

<210> SEQ ID NO 74
<211> LENGTH: 22
<212> TYPE: DNA
<213> ORGANISM: Artificial sequence
<220> FEATURE:
<223> OTHER INFORMATION: Primer

```
<400> SEQUENCE: 74
atcttggata gtacaactgt at                                        22

<210> SEQ ID NO 75
<211> LENGTH: 27
<212> TYPE: DNA
<213> ORGANISM: Artificial sequence
<220> FEATURE:
<223> OTHER INFORMATION: Primer

<400> SEQUENCE: 75 gtacttttg tcttgttgga ccaatcc                                    27

<210> SEQ ID NO 76
<211> LENGTH: 24
<212> TYPE: DNA
<213> ORGANISM: Artificial sequence
<220> FEATURE:
<223> OTHER INFORMATION: Primer

<400> SEQUENCE: 76
accatgttgc agtcaatacg taca                                      24

<210> SEQ ID NO 77
<211> LENGTH: 16
<212> TYPE: DNA
<213> ORGANISM: Artificial sequence
<220> FEATURE:
<223> OTHER INFORMATION: Primer

<400> SEQUENCE: 77 cccctccaa tgtaaa                                                16

<210> SEQ ID NO 78
<211> LENGTH: 16
<212> TYPE: DNA
<213> ORGANISM: Artificial sequence
<220> FEATURE:
<223> OTHER INFORMATION: Primer

<400> SEQUENCE: 78 cccctccag tgtaaa                                                16

<210> SEQ ID NO 79
<211> LENGTH: 35
<212> TYPE: DNA
<213> ORGANISM: Artificial sequence
<220> FEATURE:
<223> OTHER INFORMATION: Primer

<400> SEQUENCE: 79
tcagttatat taaagaaaat gtatgataaa tagca                          35

<210> SEQ ID NO 80
<211> LENGTH: 31
<212> TYPE: DNA
<213> ORGANISM: Artificial sequence
<220> FEATURE:
<223> OTHER INFORMATION: Primer

<400> SEQUENCE: 80
gcagtaaatg gatatattat acgcaaaagc a                              31

<210> SEQ ID NO 81
```

```
<211> LENGTH: 19
<212> TYPE: DNA
<213> ORGANISM: Artificial sequence
<220> FEATURE:
<223> OTHER INFORMATION: Primer

<400> SEQUENCE: 81
atgtgttggt gttgtataa                                                       19

<210> SEQ ID NO 82
<211> LENGTH: 19
<212> TYPE: DNA
<213> ORGANISM: Artificial sequence
<220> FEATURE:
<223> OTHER INFORMATION: Primer

<400> SEQUENCE: 82
atgtgttggt gatgtataa                                                       19

<210> SEQ ID NO 83
<211> LENGTH: 22
<212> TYPE: DNA
<213> ORGANISM: Artificial sequence
<220> FEATURE:
<223> OTHER INFORMATION: Primer

<400> SEQUENCE: 83
gttgttccct gctcttgctg ta                                                   22

<210> SEQ ID NO 84
<211> LENGTH: 20
<212> TYPE: DNA
<213> ORGANISM: Artificial sequence
<220> FEATURE:
<223> OTHER INFORMATION: Primer

<400> SEQUENCE: 84
caccggccaa gattcctcaa                                                      20

<210> SEQ ID NO 85
<211> LENGTH: 18
<212> TYPE: DNA
<213> ORGANISM: Artificial sequence
<220> FEATURE:
<223> OTHER INFORMATION: Primer

<400> SEQUENCE: 85
cctgtgttgt gttgttgt                                                        18

<210> SEQ ID NO 86
<211> LENGTH: 17
<212> TYPE: DNA
<213> ORGANISM: Artificial sequence
<220> FEATURE:
<223> OTHER INFORMATION: Primer

<400> SEQUENCE: 86
ctgtgttgtg ctgttgt                                                         17

<210> SEQ ID NO 87
<211> LENGTH: 526
<212> TYPE: DNA
<213> ORGANISM: Capsicum annuum

<400> SEQUENCE: 87
cccaataayc caatactaat aacttaataa tattttatc ggttcgattt atcgatcggc           60
```

```
tcaactacca aaaggaacaa aaaaataaat agagtactac aacaaccata gatgagtgaa      120
caagcgtcaa acatcagcct cagtttagta acccaaacaa gctacaatga caagccacct      180
ggccataaaa tcttcaccat tgctgcttca tggaccattg attggttctc aatcttcttt      240
gccccaccac caccaccacc ctcactatca cccacaattt ccacttcctt ttttccctcc      300 tcaaagcct aactaacaca cattggccta actaaaattc cataaatca ccttcacttc        360 ttttttcat tagattatac attagttgtt tggtctcaat cttcctttca cttcctttgg       420
cctaattaac agtttatata aatcaacttc acttctttt ttcactaaaa catacagtga       480
aagagaaaca caagagtctt ttcttgaact ggagttctag tgaaag                     526

<210> SEQ ID NO 88
<211> LENGTH: 638
<212> TYPE: DNA
<213> ORGANISM: Capsicum annuum

<400> SEQUENCE: 88
taaaaaatag tagttaattt tgaatgaaga cttacaaata cgaaaatcta taaaagaaat      60
tcatgaagga aactggccta taattgtata tacatagaga attagtatat atttaggaaa     120
tggtagaata agaaacaatg accatcactt tctctataca tttaggaaat ggtagaataa     180
gaaacaatga ccatcacttt ttccacgttc tttagaagaa agccaaataa tctctgtatt     240
tgttgaatct gttttgttta tcaatcttct acaatgtctg atgtttctat aaaatgctgt     300
acaaatttcc cgtttatgct gtccccacga ctttgcgctc ttccttcgct tcagcagttt     360
ttgaaggaaa tttcattgtc tttacacgaa atgctgccyg cataacataa acaaatggat     420
ttgaatgagt aataagctac tgccaatgcc aacgtatctt ttaaagcata tcaagcaaga     480
atttcacgaa tcacaccctta tcagaaccaa atacgattac atctgatgaa tgaaaacgca    540
tagggaagtt tggagacacc cgatatcttc tgccttcatt actacataat gcagaacaat     600
gtaattcttt tgtcttcata gactaataaa tgtgatgc                             638

<210> SEQ ID NO 89
<211> LENGTH: 509
<212> TYPE: DNA
<213> ORGANISM: Capsicum annuum

<400> SEQUENCE: 89
ggcagcattt cgtgtaaaga caatgaaatt tccttcaaaa actgctgaag cgaaggaaga      60
gcgcaaagtc gtgggacag cataaacggg aaatttgtac agcattttat agaaacatca      120
gacattgtag aagattgata aacaaaacag attcaacaaa tacagagatt atttggcttt     180
cttctaaaga acgtggaaaa agtgatggtc attgttcttt attctaccat ttcctaaatg     240
tatagagaaa gtgatggtca ttgtttctta ttctaccatt tcctaaatat atactaattc     300
tctatgtata tacaattata ggccagtttc cttcatgaat ttctttata gattttcgta      360 tttgtaagtc ttcattcaaa attaactact atttttact tttatttcta acktgcatta      420 tttttactt ttatttctaa cttgcatttt atgttcattg ttgattttat acataataaa      480
atgaaacaaa tagaaaaaaa taataaatt                                       509

<210> SEQ ID NO 90
<211> LENGTH: 5
<212> TYPE: DNA
<213> ORGANISM: Capsicum annuum
```

```
<400> SEQUENCE: 90 caggc                                                                  5

<210> SEQ ID NO 91
<211> LENGTH: 5
<212> TYPE: DNA
<213> ORGANISM: Capsicum annuum

<400> SEQUENCE: 91 cgggc                                                                  5

<210> SEQ ID NO 92
<211> LENGTH: 29
<212> TYPE: DNA
<213> ORGANISM: Artificial sequence
<220> FEATURE:
<223> OTHER INFORMATION: Primer

<400> SEQUENCE: 92
cagcagtttt tgaaggaaat ttcattgtc                                       29

<210> SEQ ID NO 93
<211> LENGTH: 25
<212> TYPE: DNA
<213> ORGANISM: Artificial sequence
<220> FEATURE:
<223> OTHER INFORMATION: Primer

<400> SEQUENCE: 93
ggcattggca gtagcttatt actca                                           25

<210> SEQ ID NO 94
<211> LENGTH: 17
<212> TYPE: DNA
<213> ORGANISM: Artificial sequence
<220> FEATURE:
<223> OTHER INFORMATION: Probe

<400> SEQUENCE: 94
atgttatgcg ggcagca                                                    17

<210> SEQ ID NO 95
<211> LENGTH: 17
<212> TYPE: DNA
<213> ORGANISM: Artificial sequence
<220> FEATURE:
<223> OTHER INFORMATION: Probe

<400> SEQUENCE: 95
atgttatgca ggcagca                                                    17

<210> SEQ ID NO 96
<211> LENGTH: 5752
<212> TYPE: DNA
<213> ORGANISM: Capsicum annuum

<400> SEQUENCE: 96
cccaataacc caatactaat aacttaataa tattttttatc ggttcgattt atcgatcggc    60
tcaactacca aaaggaacaa aaaaataaat agagtactac aacaaccata gatgagtgaa    120
caagcgtcaa acatcagcct cagtttagta acccaaacaa gctacaatga caagccacct   180
ggccataaaa tcttcaccat tgctgcttca tggaccattg attggttctc aatcttcttt   240
gccccaccac caccaccacc ctcactatca cccacaattt ccacttcctt ttttcccctcc  300
```

```
tcaaaagcct aactaacaca cattggccta actaaaattc tcataaatca ccttcacttc      360 ttttttttcat tagattatac attagttgtt tggtctcaat cttcctttca cttcctttgg     420
cctaattaac agtttatata aatcaacttc acttctttttt ttcactaaaa catacagtga    480
aagagaaaca caagagtctt ttcttgaact ggagttctag tgaaagatgt attcaactgt     540
gttttacact tcagttcatc cctccacttc agttttttca agaaaacagc tacctttatt    600
gatatccaag gactttcctg cagagttgta tcattcttta ccttgtaaga gtttggaaaa    660
tgggcatatc aagaaggtta aaggagtaaa agccacacta gctgaagctc cagctactcc    720
tacagagaag agtaactctg aggttccaca gaagaagttg aaagtacttg tggcaggtgg    780
tgggattgga ggattagttt ttgctttggc agcaaagaaa aaggggtttg atgtattggt    840
gtttgagaga gatttaagtg ctataagagg tgaggggcaa tatagaggtc caattcagat    900
acagagcaat gcattggctg ctttggaagc aattgatatg gatgttgctg aagagatcat    960
gaatgctggc tgtatcactg gtcaaaggat taatggcttg gtcgatggta tttctggcaa    1020
ctggtaaatt cacatcactc tgatttgatt gtgctgatta agagcttgtg tgcctttttt    1080
gctactgtat ttactttcca aacttgttcg gttatgcttt acttaagccg agggtcttca    1140
ggaatagtct ctctaccttc acgagatatg attaaggtct gcgcacgcaa tacccttctc    1200
agaagggtaa tcacactggc tatgttgttg ttgtaattaa atgcttgtct gtcttttttt    1260
agttgagctt taactgagga tacccccagga aaataatgaa ttctttgaaa tatttagccc    1320
tttaaaaaag tatagggaaa ataattcatt tagtcacaag tttattgaat catggttgcc    1380
aagcttattc gggaaaagga tcctatcttt accttcaaat ggcttcaatc agattgataa    1440
gttagtctta ttgttgtatg agcagcttat tgtgagaaca gtcccttat ttcttgaact     1500 gcgaacagtg acaatagttg ggtatcaggt attgcaagtt tgatacgttc actccagctg    1560
tggaacgtgg acttcctgtg acaagagtca tcagccgcat gactttgcaa cagattcttg    1620
cacgtgctgt aggggaggat gtaattatga atgaaagtaa tgtagtaaat tttgaggatg    1680
atggggagaa ggtaatgcta ggtttgatct cttgtttttc tgctattctc aaaatatcaa    1740
gaaagattat aacttttctt aatttcattt gcatcattgt taattgttgt ttcttattca    1800
tcaattttcg ttaaagcttc tcatgtgctg tgtgaaatca ggttactgtg gttcttgaga    1860
atggacaacg gtttacaggt gatcttctgg ttggtgctga tggcataagg tctaaggtat    1920
tcaaaatcag tctcattata tttctttcta ttattactac ttcggttaac aaggatagag    1980
taacttgttt atattttact ttgagattgt ggttccacgt taaaaaattg tctgttgact    2040
gataggcctg agtccgtatt atgcagtgaa cctttttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt cttttcttacc ggattgtgtt tccactcatg cccttatccc    2280
tgctggtgcc gttacactca cacgaggttt tcatagtaga gattaaattg agatttcttt    2340
tctgaaggta ccgagtcttt ttgggccaca aacagtactt tgtttcttca gatgtgggtg    2400
gaggcaagat gcagtggtat gcatttcaca atgaaccagc tggtggtgtg gatgctccaa    2460
acggtaaaat ttttaggccg cttaaaacta tttactatag ttcaggatat agacatactt    2520
actagaagac gttttttgaat gcttaacttg taacgtttat ttaacccaag ggttttctta    2580
agaatttttc ctcattgagg cctggttata gtgttgcaat aaggtaaaga acaactcaag    2640
```

```
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggccatagag gtacaccact gtgtttatca tctttgtcaa atacacagta    3000
ttgtaaggtt gtgtatgaca ctgaactttt ccatgtacaa ctacaggata gctatcaact    3060
agcactggaa cttgagaaag catggagccg aagtgctgag tccggaagcc tatggatgt     3120 catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttct    3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatgaaaaac tatctatcac ttgaaaattgg aatggcatag ccaatttgcg tgattgcgca    3540
gagctcttct tataatagat gttttttct atttatttgtg cagttttga ccaagtatag     3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt attttgaaca tgattttggt ttctatgtga atccgtgatg agtttgctgg    3780
agatcttgga agttgatatc ctgtggtttg actcgtcttt tttcttttct tgcagcgaca    3840
agcttgaggg tagaatacaa cattgcaggc tatctgagaa agtatgtagc gtaaggaact    3900
atgcactcaa cacacgaaca cagaaaagat ttctggcttc cattgctact taattaaggt    3960
ccaactatgg attttacggg tgtgttaata tactgtactg tggtgatgaa ggcaaatgat    4020
caattgagaa gatggtttga agatgatgat gctttagagc gtgctactga tgcagagtga    4080
gttaatggaa cgtaatattt aaaaatttca tttttacatg tctcattttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260
tatgctttta ggttacggct tattggaaag attgttcata gctttgctgt tagatcctgg    4320
cagtttgcac aaagtaatct ttgttaacgt ttggttcata tgagtaagag gtacaacatt    4380
taaatgactt aattcccctt tgagaagatg gttgaagtca ttttattggc taaatgaaca    4440
tttaaagcaa gagtataaag gctacacagc atgacatctt tcttagatta tctgaattca    4500
tacttaaagc tcttaatgta tgcataacta tacaaaaaaa ttcatgcatc gtgatgcatc    4560
cattgcaaat atatccccat caatctccta gctctaatca acaaatccga tccatgcgca    4620
tcctatcaaa agtgcgtaga cattaatgga atgccacttt gcccaacttg gctgtaaggg    4680
aagaaacttg aatgaggtat tgtttcatta gaagagctac taacgtcttt aggtttcagg    4740
tctgtctcgc atacaaacat tcccggaaaa tcagtagttt taccttttgcc acaggtgatt    4800 gctatagctc agtatcctgg acattcttgt ggttaatgca tggcttagat tgtctatttt    4860
ctttgttaat cacaggtgtc tgaaatgcat gcccaaatat cctgcaaaaa caacgcattt    4920
tttgtaactg attttcagag tgaacatggt acttgggtta tagagtaagc tccatgagtt    4980
ctttatacaa ctgtactata agtgcatcac atttattagt ctatgaagac aaaagaatta    5040
```

| | | | | |
|---|---|---|---|---|
| cattgttctg | cattatgtag | taatgaaggc | agaagatatc | gggtgtctcc aaacttccct | 5100 |
| atgcgttttc | attcatcaga | tgtaatcgta | tttggttctg | ataaggtgtg attcgtgaaa | 5160 |
| ttcttgcttg | atatgcttta | aaagatacgt | tggcattggc | agtagcttat tactcattca | 5220 |
| aatccatttg | tttatgttat | gcgggcagca | tttcgtgtaa | agacaatgaa atttccttca | 5280 |
| aaaactgctg | aagcgaagga | agagcgcaaa | gtcgtgggga | cagcataaac gggaaatttg | 5340 |
| tacagcattt | tatagaaaca | tcagacattg | tagaagattg | ataaacaaaa cagattcaac | 5400 |
| aaatacagag | attatttggc | tttcttctaa | agaacgtgga | aaagtgatgg tcattgttt | 5460 |
| cttattctac | catttcctaa | atgtatagag | aaagtgatgg | tcattgtttc ttattctacc | 5520 |
| atttcctaaa | tatatactaa | ttctctatgt | atatacaatt | ataggccagt ttccttcatg | 5580 |
| aatttctttt | atagattttc | gtatttgtaa | gtcttcattc | aaaattaact actatttttt | 5640 |
| actttattt | ctaacttgca | ttatttttta | cttttatttc | taacttgcat tttatgttca | 5700 |
| ttgttgattt | tatacataat | aaaatgaaac | aaatagaaaa | aataataaa tt | 5752 |

<210> SEQ ID NO 97
<211> LENGTH: 5752
<212> TYPE: DNA
<213> ORGANISM: Capsicum annuum

<400> SEQUENCE: 97

| | | | | |
|---|---|---|---|---|
| cccaataatc | caatactaat | aacttaataa | tatttttatc | ggttcgattt atcgatcggc | 60 |
| tcaactacca | aaaggaacaa | aaaaataaat | agagtactac | aacaaccata gatgagtgaa | 120 |
| caagcgtcaa | acatcagcct | cagtttagta | acccaaacaa | gctacaatga caagccacct | 180 |
| ggccataaaa | tcttcaccat | tgctgcttca | tggaccattg | attggttctc aatcttcttt | 240 |
| gccccaccac | caccaccacc | ctcactatca | cccacaattt | ccacttcctt ttttccctcc | 300 |
| tcaaaagcct | aactaacaca | cattggccta | actaaaattc | tcataaatca ccttcacttc | 360 |
| ttttttcat | tagattatac | attagttgtt | tggtctcaat | cttcctttca cttcctttgg | 420 |
| cctaattaac | agtttatata | aatcaacttc | acttcttttt | ttcactaaaa catacagtga | 480 |
| aagagaaaca | caagagtctt | tcttgaact | ggagttctag | tgaaagatgt attcaactgt | 540 |
| gttttacact | tcagttcatc | cctccacttc | agttttttca | agaaaacagc tacctttatt | 600 |
| gatatccaag | gactttcctg | cagagttgta | tcattcttta | ccttgtaaga gtttggaaaa | 660 |
| tgggcatatc | aagaaggtta | aaggagtaaa | agccacacta | gctgaagctc cagctactcc | 720 |
| tacagagaag | agtaactctg | aggttccaca | gaagaagttg | aaagtacttg tggcaggtgg | 780 |
| tgggattgga | ggattagttt | ttgctttggc | agcaaagaaa | aaggggtttg atgtattggt | 840 |
| gtttgagaga | gatttaagtg | ctataagagg | tgagggcaa | tatagaggtc caattcagat | 900 |
| acagagcaat | gcattggctg | ctttggaagc | aattgatatg | gatgttgctg aagagatcat | 960 |
| gaatgctggc | tgtatcactg | gtcaaaggat | taatggcttg | gtcgatggta tttctggcaa | 1020 |
| ctggtaaatt | cacatcactc | tgatttgatt | gtgctgatta | agagcttgtg tgccttttt | 1080 |
| gctactgtat | ttactttcca | aacttgttcg | gttatgcttt | acttaagccg agggtcttca | 1140 |
| ggaatagtct | ctctaccttc | acgagatatg | attaaggtct | gcgcacgcaa tacccttctc | 1200 |
| agaagggtaa | tcacactggc | tatgttgttg | ttgtaattaa | atgcttgtct gtcttttttt | 1260 |
| agttgagctt | taactgagga | tacccccagga | aaataatgaa | ttctttgaaa tatttagccc | 1320 |
| tttaaaaaag | tatagggaaa | ataattcatt | tagtcacaag | tttattgaat catggttgcc | 1380 |

```
aagcttattc gggaaaagga tcctatcttt accttcaaat ggcttcaatc agattgataa    1440
gttagtctta ttgttgtatg agcagcttat tgtgagaaca gtccctttat ttcttgaact    1500
gcgaacagtg acaatagttg ggtatcaggt attgcaagtt tgatacgttc actccagctg    1560
tggaacgtgg acttcctgtg acaagagtca tcagccgcat gactttgcaa cagattcttg    1620
cacgtgctgt agggaggat gtaattatga atgaaagtaa tgtagtaaat tttgaggatg     1680
atggggagaa ggtaatgcta ggtttgatct ctttgttttc tgctattctc aaaatatcaa    1740
gaaagattat aactttctt aatttcattt gcatcattgt taattgttgt ttcttattca     1800
tcaattttcg ttaaagcttc tcatgtgctg tgtgaaatca ggttactgtg gttcttgaga    1860
atggacaacg gtttacaggt gatcttctgg ttggtgctga tggcataagg tctaaggtat    1920
tcaaaatcag tctcattata tttctttcta ttattactac ttcggttaac aaggatagag    1980
taacttgttt atattttact ttgagattgt ggttccacgt taaaaaattg tctgttgact    2040
gataggcctg agtccgtatt atgcagtgaa ccttttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt cttcttacc ggattgtgtt tccactcatg cccttatccc     2280
tgctggtgcc gttacactca cacgaggttt tcatagtaga gattaaattg agatttcttt    2340
tctgaaggta ccgagtcttt tgggccaca acagtactt tgtttcttca gatgtgggtg      2400
gaggcaagat gcagtggtat gcatttcaca atgaaccagc tggtggtgtg gatgctccaa    2460
acggtaaaat ttttaggccg cttaaaacta tttactatag ttcaggatat agacatactt    2520
actagaagac gttttgaat gcttaacttg taacgtttat ttaacccaag gggtttctta     2580
agaatttttc ctcattgagg cctggttata gtgttgcaat aaggtaaaga acaactcaag    2640
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggcctagag gtacaccact gtgtttatca tctttgtcaa atacacagta     3000
ttgtaaggtt gtgtatgaca ctgaactttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttct     3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatgaaaaac tatctatcac ttgaaattgg aatggcatag ccaatttgcg tgattgcgca    3540
gagctcttct tataatagat gttttttct attatttgtg cagtttttga ccaagtatag     3600
gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt atttttgaaca tgattttggt ttctatgtga atccgtgatg agtttgctgg   3780
```

```
agatcttgga agttgatatc ctgtggtttg actcgtcttt tttctttttct tgcagcgaca   3840 agcttgaggg tagaatacaa cattgcaggc tatctgagaa agtatgtagc gtaaggaact   3900
atgcactcaa cacacgaaca cagaaaagat ttctggcttc cattgctact taattaaggt   3960
ccaactatgg attttacggg tgtgttaata tactgtactg tggtgatgaa ggcaaatgat   4020
caattgagaa gatggtttga agatgatgat gctttagagc gtgctactga tgcagagtga   4080
gttaatggaa cgtaatattt aaaaatttca tttttacatg tctcattttc ctagtttgct   4140
ttctaatttg gtgcttacgt tttatctttc aggtggttac tgttacctgc agcgaatggc   4200
aattctgctt tagaaactat tgttttaagc agagatgagg atgtcccttg cactatcggg   4260
tatgctttta ggttacggct tattggaaag attgttcata gctttgctgt tagatcctgg   4320
cagtttgcac aaagtaatct ttgttaacgt ttggttcata tgagtaagag gtacaacatt   4380
taaatgactt aattccccctt tgagaagatg gttgaagtca ttttattggc taaatgaaca   4440
tttaaagcaa gagtataaag gctacacagc atgacatctt tcttagatta tctgaattca   4500
tacttaaagc tcttaatgta tgcataacta tacaaaaaaa ttcatgcatc gtgatgcatc   4560
cattgcaaat atatccccat caatctccta gctctaatca acaaatccga tccatgcgca   4620
tcctatcaaa agtgcgtaga cattaatgga atgccacttt gcccaacttg gctgtaaggg   4680
aagaaacttg aatgaggtat tgtttcatta gaagagctac taacgtcttt aggtttcagg   4740
tctgtctcgc atacaaacat tcccggaaaa tcagtagttt tacctttgcc acaggtgatt   4800
gctatagctc agtatcctgg acattcttgt ggttaatgca tggcttagat tgtctatttt   4860
ctttgttaat cacaggtgtc tgaaatgcat gcccaaatat cctgcaaaaa caacgcattt   4920
tttgtaactg atttttcagag tgaacatggt acttgggtta tagagtaagc tccatgagtt   4980
ctttatacaa ctgtactata agtgcatcac atttattagt ctatgaagac aaaagaatta   5040
cattgttctg cattatgtag taatgaaggc agaagatatc gggtgtctcc aaacttccct   5100
atgcgttttc attcatcaga tgtaatcgta tttggttctg ataaggtgtg attcgtgaaa   5160
ttcttgcttg atatgcttta aaagatacgt tggcattggc agtagcttat tactcattca   5220
aatccatttg tttatgttat gcgggcagca tttcgtgtaa agacaatgaa atttccttca   5280
aaaactgctg aagcgaagga agagcgcaaa gtcgtgggga cagcataaac gggaaatttg   5340
tacagcattt tatagaaaca tcagacattg tagaagattg ataaacaaaa cagattcaac   5400
aaatacagag attatttggc tttcttctaa agaacgtgga aaaagtgatg gtcattgttt   5460
cttattctac catttcctaa atgtatagag aaagtgatgg tcattgtttc ttattctacc   5520
atttcctaaa tatatactaa ttctctatgt atatacaatt ataggccagt ttccttcatg   5580
aatttctttt atagattttc gtatttgtaa gtcttcattc aaaattaact actattttt   5640 acttttattt ctaacgtgca ttatttttta ctttttattc taacttgcat tttatgttca   5700
ttgttgattt tatacataat aaaatgaaac aaatagaaaa aaataataaa tt           5752
```

<210> SEQ ID NO 98
<211> LENGTH: 1971
<212> TYPE: DNA
<213> ORGANISM: Capsicum annuum
<400> SEQUENCE: 98

```
atgtattcaa ctgtgtttta cacttcagtt catccctcca cttcagtttt ttcaagaaaa     60 cagctaccctt tattgatatc caaggacttt cctgcagagt tgtatcattc tttaccttgt   120
```

| | |
|---|---|
| aagagtttgg aaaatgggca tatcaagaag gttaaaggag taaaagccac actagctgaa | 180 |
| gctccagcta ctcctacaga gaagagtaac tctgaggttc cacagaagaa gttgaaagta | 240 |
| cttgtggcag gtggtgggat tggaggatta gttttgctt tggcagcaaa gaaaaagggg | 300 |
| tttgatgtat tggtgtttga gagagattta agtgctataa gaggtgaggg gcaatataga | 360 |
| ggtccaattc agatacagag caatgcattg gctgctttgg aagcaattga tatggatgtt | 420 |
| gctgaagaga tcatgaatgc tggctgtatc actggtcaaa ggattaatgg cttggtcgat | 480 |
| ggtatttctg gcaactggta ttgcaagttt gatacgttca ctccagctgt ggaacgtgga | 540 |
| cttcctgtga caagagtcat cagccgcatg actttgcaac agattcttgc acgtgctgta | 600 |
| ggggaggatg taattatgaa tgaaagtaat gtagtaaatt ttgaggatga tggggagaag | 660 |
| gtaatgctag gtttgatctc tttgttttct gctacaggtg atcttctggt tggtgctgat | 720 |
| ggcataaggt ctaaggtacg gactaatttg ttcggacaca gtgaagctac ttactctggt | 780 |
| tacacttgtt atactggaat tgcagatttc gttcctgctg atattgacac agttgggtac | 840 |
| cgagtctttt tgggccacaa acagtacttt gtttcttcag atgtgggtgg aggcaagatg | 900 |
| cagtggtatg catttcacaa tgaaccagct ggtggtgtgg atgctccaaa cggtaaaaag | 960 |
| gaaagattgc ttaaaatatt tggggatgg tgtgacaacg ttatagacct attagttgcc | 1020 |
| acagatgaag atgcaattct tcgtcgtgac atctatgata gaccgccaac atttaattgg | 1080 |
| ggaagaggtc gtgttacatt gcttggggac tcagtccatg ctatgcagcc taatttgggt | 1140 |
| caaggaggat gcatggccat agaggatagc tatcaactag cactggaact tgagaaagca | 1200 |
| tggagccgaa gtgctgagtc cggaagccct atggatgtca tctcatcttt aaggagctat | 1260 |
| gaaagtgcta gaaaacttcg agttggagtt atccatggac tggctagaat ggctgcaatc | 1320 |
| atggcatcaa cttacaaggc ctatcttggt gtcggacttg gtccattatc agtatggacc | 1380 |
| aagtatagga taccacatcc tggaagagtt ggtggaagag tatttgtgga cttgggaatg | 1440 |
| cctctaatgt taagttgggt tctaggaggc aacgggagaa tacaacattg caggctatct | 1500 |
| gagaaagcaa atgatcaatt gagaagatgg tttgaagatg atgatgcttt agagcgtgct | 1560 |
| actgatgcag agtggttact gttacctgca gcgaatggca attctgcttt agaaactatt | 1620 |
| gttttaagca gagatgagga tgtcccttgc actatcgggt ctgtctcgca tacaaacatt | 1680 |
| cccggaaaat cagtagtttt accttttgcca caggtgtctg aaatgcatgc ccaaatatcc | 1740 |
| tgcaaaaaca acgcattttt tgtaactgat tttcagagtg aacatggtac ttgggttata | 1800 |
| gataatgaag gcagaagata tcgggtgtct ccaaacttcc ctatgcgttt tcattcatca | 1860 |
| gatgtaatcg tatttggttc tgataaggca gcatttcgtg taaagacaat gaaatttcct | 1920 |
| tcaaaaactg ctgaagcgaa ggaagagcgc aaagtcgtgg ggacagcata a | 1971 |

<210> SEQ ID NO 99
<211> LENGTH: 5752
<212> TYPE: DNA
<213> ORGANISM: Capsicum annuum

<400> SEQUENCE: 99

| | |
|---|---|
| cccaataacc caatactaat aacttaataa tatttttatc ggttcgattt atcgatcggc | 60 |
| tcaactacca aaaggaacaa aaaaataaat agagtactac aacaaccata gatgagtgaa | 120 |
| caagcgtcaa acatcagcct cagtttagta acccaaacaa gctacaatga caagccacct | 180 |
| ggccataaaa tcttccaccat tgctgcttca tggaccattg attggttctc aatcttcttt | 240 |
| gccccaccac caccaccacc ctcactatca cccacaattt ccacttcctt ttttccctcc | 300 |

```
tcaaaagcct aactaacaca cattggccta actaaaattc tcataaatca ccttcacttc    360 ttttttttcat tagattatac attagttgtt tggtctcaat cttcctttca cttcctttgg    420
cctaattaac agtttatata aatcaacttc acttcttttt ttcactaaaa catacagtga    480
aagagaaaca caagagtctt ttcttgaact ggagttctag tgaaagatgt attcaactgt    540
gttttacact tcagttcatc cctccacttc agttttttca agaaaacagc tacctttatt    600
gatatccaag gactttcctg cagagttgta tcattcttta ccttgtaaga gtttggaaaa    660
tgggcatatc aagaaggtta aaggagtaaa agccacacta gctgaagctc cagctactcc    720
tacagagaag agtaactctg aggttccaca gaagaagttg aaagtacttg tggcaggtgg    780
tgggattgga ggattagttt ttgctttggc agcaaagaaa aaggggtttg atgtattggt    840
gtttgagaga gatttaagtg ctataagagg tgaggggcaa tatagaggtc caattcagat    900
acagagcaat gcattggctg ctttggaagc aattgatatg gatgttgctg aagagatcat    960
gaatgctggc tgtatcactg gtcaaaggat taatggcttg gtcgatggta tttctggcaa   1020
ctggtaaatt cacatcactc tgatttgatt gtgctgatta agagcttgtg tgcctttttt   1080
gctactgtat ttactttcca aacttgttcg gttatgcttt acttaagccg agggtcttca   1140
ggaatagtct ctctaccttc acgagatatg attaaggtct gcgcacgcaa tacccttctc   1200
agaagggtaa tcacactggc tatgttgttg ttgtaattaa atgcttgtct gtcttttttt   1260
agttgagctt taactgagga taccccagga aaataatgaa ttctttgaaa tatttagccc   1320
tttaaaaaag tatagggaaa ataattcatt tagtcacaag tttattgaat catggttgcc   1380
aagcttattc gggaaaagga tcctatcttt accttcaaat ggcttcaatc agattgataa   1440
gttagtctta ttgttgtatg agcagcttat tgtgagaaca gtcccttttat ttcttgaact   1500 gcgaacagtg acaatagttg ggtatcaggt attgcaagtt tgatacgttc actccagctg   1560
tggaacgtgg acttcctgtg acaagagtca tcagccgcat gactttgcaa cagattcttg   1620
cacgtgctgt aggggaggat gtaattatga atgaaagtaa tgtagtaaat tttgaggatg   1680
atggggagaa ggtaatgcta ggtttgatct ctttgttttc tgctattctc aaaatatcaa   1740
gaaagattat aacttttctt aatttcattt gcatcattgt taattgttgt ttcttattca   1800
tcaattttcg ttaaagcttc tcatgtgctg tgtgaaatca ggttactgtg gttcttgaga   1860
atggacaacg gtttacaggt gatcttctgg ttggtgctga tggcataagg tctaaggtat   1920
tcaaaatcag tctcattata tttctttcta ttattactac ttcggttaac aaggatagag   1980
taacttgttt atattttact ttgagattgt ggttccacgt taaaaaattg tctgttgact   2040
gataggcctg agtccgtatt atgcagtgaa ccttttattg attattctag ttgattcaga   2100
agatcacaaa catttccgtt gtgttgtagg tacggactaa tttgttcgga cacagtgaag   2160
ctacttactc tggttacact tgttatactg gaattgcaga tttcgttcct gctgatattg   2220
acacagttgg gtatgatatt cttttcttacc ggattgtgtt tccactcatg cccttatccc   2280
tgctggtgcc gttacactca cacgaggttt tcatagtaga gattaaattg agatttcttt   2340
tctgaaggta ccgagtcttt ttgggccaca aacagtactt tgtttcttca gatgtgggtg   2400
gaggcaagat gcagtggtat gcatttcaca atgaaccagc tggtggtgtg atgctccaa   2460 acggtaaaat ttttaggccg cttaaaacta tttactatag ttcaggatat agacatactt   2520
actagaagac gttttttgaat gcttaacttg taacgtttat ttaacccaag ggtttctta   2580 agaatttttc ctcattgagg cctggttata gtgttgcaat aaggtaaaga acaactcaag   2640
```

```
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggcctatagag gtacaccact gtgtttatca tctttgtcaa atacacagta    3000
ttgtaaggtt gtgtatgaca ctgaactttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt ccttttttct    3360
gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatgaaaaac tatctatcac ttgaaaattgg aatggcatag ccaatttgcg tgattgcgca    3540
gagctcttct tataatagat gttttttttct attatttgtg cagttttttga ccaagtatag    3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt attttgaaca tgattttggt ttctatgtga atccgtgatg agtttgctgg    3780
agatcttgga agttgatatc ctgtggtttg actcgtcttt tttcttttct tgcagcgaca    3840
agcttgaggg tagaatacaa cattgcaggc tatctgagaa agtatgtagc gtaaggaact    3900
atgcactcaa cacacgaaca cagaaaagat ttctggcttc cattgctact taattaaggt    3960
ccaactatgg attttacggg tgtgttaata tactgtactg tggtgatgaa ggcaaatgat    4020
caattgagaa gatggtttga agatgatgat gctttagagc gtgctactga tgcagagtga    4080
gttaatggaa cgtaatattt aaaaatttca tttttacatg tctcattttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260
tatgctttta ggttacggct tattggaaag attgttcata gctttgctgt tagatcctgg    4320
cagtttgcac aaagtaatct ttgttaacgt ttggttcata tgagtaagag gtacaacatt    4380
taaatgactt aattccccct tgagaagatg gttgaagtca ttttattggc taaatgaaca    4440
tttaaagcaa gagtataaag gctacacagc atgacatctt tcttagatta tctgaattca    4500
tacttaaagc tcttaatgta tgcataacta tacaaaaaaa ttcatgcatc gtgatgcatc    4560
cattgcaaat atatccccat caatctccta gctctaatca acaaatccga tccatgcgca    4620
tcctatcaaa agtgcgtaga cattaatgga atgccacttt gcccaacttg gctgtaaggg    4680
aagaaacttg aatgaggtat tgtttcatta gaagagctac taacgtcttt aggtttcagg    4740
tctgtctcgc atacaaacat tcccggaaaa tcagtagttt tacctttgcc acaggtgatt    4800
gctatagctc agtatcctgg acattcttgt ggttaatgca tggcttagat tgtctatttt    4860
ctttgttaat cacaggtgtc tgaaatgcat gcccaaatat cctgcaaaaa caacgcattt    4920
tttgtaactg attttcagag tgaacatggt acttgggtta tagagtaagc tccatgagtt    4980
ctttatacaa ctgtactata agtgcatcac atttattagt ctatgaagac aaaagaatta    5040
```

```
cattgttctg cattatgtag taatgaaggc agaagatatc gggtgtctcc aaacttccct      5100
atgcgttttc attcatcaga tgtaatcgta tttggttctg ataaggtgtg attcgtgaaa      5160
ttcttgcttg atatgcttta aaagatacgt tggcattggc agtagcttat tactcattca      5220
aatccatttg tttatgttat gcaggcagca tttcgtgtaa agacaatgaa atttccttca      5280
aaaactgctg aagcgaagga agagcgcaaa gtcgtgggga cagcataaac gggaaatttg      5340
tacagcattt tatagaaaca tcagacattg tagaagattg ataaacaaaa cagattcaac      5400
aaatacagag attatttggc tttcttctaa agaacgtgga aaaagtgatg gtcattgttt      5460
cttattctac catttcctaa atgtatagag aaagtgatgg tcattgtttc ttattctacc      5520
atttcctaaa tatatactaa ttctctatgt atatacaatt ataggccagt ttccttcatg      5580
aatttctttt atagattttc gtatttgtaa gtcttcattc aaaattaact actattttt       5640 acttttattt ctaacttgca ttattttta cttttatttc taacttgcat tttatgttca       5700
ttgttgattt tatacataat aaaatgaaac aaatagaaaa aaataataaa tt              5752
```

What is claimed is:

1. A method of producing *Capsicum* pepper seed, said method comprising:
   (a) obtaining a plurality of *Capsicum* pepper plants;
   (b) selecting at least a first *Capsicum* pepper plant comprising a Capsanthin-capsorubin synthase (Ccs) allele comprising a polymorphism associated with fruit color at marker locus NCANN009113770 or marker locus NCANN005134316;
   (c) crossing said at least a first *Capsicum* pepper plant comprising said polymorphism with itself or a second *Capsicum* pepper plant;
   (d) repeating steps (a)-(c) to produce a set of near isogenic inbred *Capsicum* pepper lines that collectively comprise functional and non-functional Capsanthin-capsorubin synthase (Ccs) alleles; and
   (e) crossing said *Capsicum* pepper lines to produce seed of near isogenic hybrid plants that comprise combinations of said alleles that result in red, yellow and orange fruit.

2. The method of claim 1, wherein producing a set of near isogenic lines comprises producing a plant that has been inbred but segregates for a Ccs allele.

3. The method of claim 2, wherein the plant that has been inbred has been selfed for three or more generations.

4. The method of claim 1, wherein said selecting comprises detecting a deletion in a Ccs gene or the absence of said deletion thereof.

5. The method of claim 1, wherein the near isogenic inbred *Capsicum* pepper lines are homozygous for said Ccs alleles.

6. The method of claim 1, wherein the *Capsicum* pepper lines are selected from the *Capsicum* pepper species consisting of *Capsicum annuum, C. baccatum, C. chinense, C. frutescens*, and *C. pubescens*.

7. The method of claim 1, wherein the *Capsicum* pepper lines are sweet peppers.

8. A method of selecting a *Capsicum* pepper plant for fruit color genotype, said method comprising:
   (a) obtaining a sample of nucleic acids from a *Capsicum* plant or a portion thereof;
   (b) detecting the presence or absence of a Capsanthin-capsorubin synthase (Ccs) allele comprising a polymorphism conferring said fruit color in marker locus NCANN009113770 or marker locus NCANN005134316;
   (c) selecting the plant based on the presence or absence of said allele; and
   (d) crossing the selected plant with a second *Capsicum* pepper plant to obtain at least a first progeny plant comprising or lacking said allele.

9. The method of claim 8, wherein said polymorphism in said Capsanthin-capsorubin synthase (Ccs) allele comprises a mutation in a Ccs gene.

10. The method of claim 9, wherein the mutation in the Capsanthin-capsorubin synthase (Ccs) gene comprises the presence of a deletion site in the Ccs gene that is causative for said fruit color.

11. The method of claim 8, wherein the plant is a *Capsicum annuum* plant.

12. The method of claim 11, wherein the plant is a sweet *Capsicum* pepper plant.

13. The method of claim 1, wherein said Capsanthin-capsorubin synthase (Ccs) allele comprises a polymorphism associated with fruit color at marker locus NCANN009113770.

14. The method of claim 1, wherein said Capsanthin-capsorubin synthase (Ccs) allele comprises a polymorphism associated with fruit color at marker locus NCANN005134316.

15. The method of claim 8, wherein said Capsanthin-capsorubin synthase (Ccs) allele comprises a polymorphism conferring said fruit color in marker locus NCANN009113770.

16. The method of claim 8, wherein said Capsanthin-capsorubin synthase (Ccs) allele comprises a polymorphism conferring said fruit color in marker locus NCANN005134316.

* * * * *